US010134994B2

(12) United States Patent
Mitchell et al.

(10) Patent No.: US 10,134,994 B2
(45) Date of Patent: Nov. 20, 2018

(54) POLYCYCLIC POLYMER COMPRISING THIOPHENE UNITS, A METHOD OF PRODUCING AND USES OF SUCH POLYMER

(71) Applicant: MERCK PATENT GMBH, Darmstadt (DE)

(72) Inventors: William Mitchell, Chandler's Ford (GB); Mansoor D'Lavari, Bude (GB); Changsheng Wang, Durham (GB); David Sparrowe, Bournemouth (GB)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/100,360

(22) PCT Filed: Oct. 29, 2014

(86) PCT No.: PCT/EP2014/002911
§ 371 (c)(1),
(2) Date: May 31, 2016

(87) PCT Pub. No.: WO2015/078551
PCT Pub. Date: Jun. 4, 2015

(65) Prior Publication Data
US 2016/0301008 A1 Oct. 13, 2016

(30) Foreign Application Priority Data

Nov. 28, 2013 (EP) ..................................... 13005555

(51) Int. Cl.
| | | |
|---|---|---|
| *H01B 1/00* | (2006.01) | |
| *H01L 51/00* | (2006.01) | |
| *C08K 3/04* | (2006.01) | |
| *C08G 61/12* | (2006.01) | |
| *C09K 11/06* | (2006.01) | |
| *H01B 1/12* | (2006.01) | |
| *C07D 495/22* | (2006.01) | |
| *H01L 51/05* | (2006.01) | |
| *H01L 51/42* | (2006.01) | |

(52) U.S. Cl.
CPC ........ *H01L 51/0036* (2013.01); *C07D 495/22* (2013.01); *C08G 61/123* (2013.01); *C08G 61/126* (2013.01); *C08K 3/04* (2013.01); *C09K 11/06* (2013.01); *H01B 1/127* (2013.01); *H01L 51/0043* (2013.01); *H01L 51/0094* (2013.01); *C08G 2261/124* (2013.01); *C08G 2261/148* (2013.01); *C08G 2261/1412* (2013.01); *C08G 2261/314* (2013.01); *C08G 2261/3142* (2013.01); *C08G 2261/3223* (2013.01); *C08G 2261/3243* (2013.01); *C08G 2261/3246* (2013.01); *C08G 2261/411* (2013.01); *C08G 2261/414* (2013.01); *C08G 2261/514* (2013.01); *C08G 2261/91* (2013.01); *C08G 2261/92* (2013.01); *C08G 2261/95* (2013.01); *C09K 2211/1011* (2013.01); *C09K 2211/1092* (2013.01); *C09K 2211/1458* (2013.01); *H01L 51/0074* (2013.01); *H01L 51/0541* (2013.01); *H01L 51/0558* (2013.01); *H01L 51/4253* (2013.01); *Y02E 10/549* (2013.01)

(58) Field of Classification Search
CPC . H01B 1/127; H01L 51/0036; H01L 51/0043; H01L 51/0094; C08K 3/04; C08G 61/123; C08G 61/126; C08L 65/00; C07D 495/22; C09K 11/06
USPC ........................................................ 252/500
See application file for complete search history.

(56) References Cited

U.S. PATENT DOCUMENTS

| | | | | |
|---|---|---|---|---|
| 6,645,401 B2* | 11/2003 | Giles | .................... | C07D 233/46 106/31.92 |
| 8,709,290 B2 | 4/2014 | Tierney et al. | | |
| 9,062,152 B2 | 6/2015 | Grenier et al. | | |
| 9,695,190 B2* | 7/2017 | Mitchell | ............. | H01L 51/0043 |
| 9,806,263 B2* | 10/2017 | Mitchell | ............. | H01L 51/0003 |
| 2003/0021912 A1* | 1/2003 | Farrand | ................ | C07D 495/14 428/1.1 |
| 2011/0168953 A1 | 7/2011 | Tierney et al. | | |
| 2012/0283377 A1 | 11/2012 | Grenier et al. | | |
| 2013/0237676 A1 | 9/2013 | Hsu et al. | | |
| 2014/0029453 A1* | 1/2014 | Trainin | ................. | H04W 24/10 370/252 |
| 2014/0131628 A1 | 5/2014 | D'Lavari et al. | | |
| 2014/0158949 A1 | 6/2014 | Wang et al. | | |
| 2015/0041727 A1 | 2/2015 | Wang et al. | | |
| 2015/0048279 A1 | 2/2015 | Mitchell et al. | | |
| 2015/0144847 A1 | 5/2015 | D'Lavari et al. | | |
| 2015/0322208 A1* | 11/2015 | Mitchell | ............. | H01L 51/0043 257/40 |
| 2018/0105637 A1* | 4/2018 | Mitchell | ............. | C08G 61/126 |

FOREIGN PATENT DOCUMENTS

| | | | |
|---|---|---|---|
| WO | 2012058209 A1 | 5/2012 | |
| WO | 2013007334 A2 | 1/2013 | |

(Continued)

OTHER PUBLICATIONS

International Search Report for PCT/EP2014/002911 dated May 13, 2015.

(Continued)

*Primary Examiner* — Douglas J McGinty
(74) *Attorney, Agent, or Firm* — Millen White Zelano and Branigan, PC; John Sopp

(57) ABSTRACT

The present invention relates to a novel polycyclic polymer comprising fused thiophene units. The present invention also relates to a method for producing such polymer as well as the use of such polymer, particularly in organoelectronic applications.

16 Claims, No Drawings

(56) References Cited

FOREIGN PATENT DOCUMENTS

| WO | 2013010614 A2 | 1/2013 | |
|---|---|---|---|
| WO | WO-2013007334 A2 * | 1/2013 | ........... C08G 61/126 |
| WO | 2013120575 A1 | 8/2013 | |
| WO | 2010031480 A1 | 10/2013 | |
| WO | 2013159862 A1 | 10/2013 | |
| WO | 2013159863 A1 | 10/2013 | |

OTHER PUBLICATIONS

Setayesh, S. et al., "Bridging the Gap between Polyfluorene and Ladder-Poly-p-phenylene: Synthesis and Characterization of Poly-2,8-indenofluorene," Macromolecules, 2000, vol. 33, pp. 2016-2020.

Zhang, W. et al., "Indacenodithiophene semiconducting Polymers for High-Performance, Air Stable Transistors," JACS Communications, vol. 132, pp. 11437-11439.

Cheng, Y. et al., "Dithienocyclopentathieno [3,2-b]thiophene Hexacyclic Arene for Solution-Processed Organic Field-Effect Transistors and Photovoltaic Applications," Chemistry—An Asian Journal, Apr. 2012, vol. 7, No. 4, pp. 318-825.

Cheng, Y. et al., "Diindenothieno[2,3-b]thiphene arene for efficient organic photovoltaics with an extra high open circuit voltage of 1.14ev," Chemical Communications, Jan. 1, 2012, vol. 48, No. 26, pp. 3203-3205.

Schroeder, B. C. et al., "Synthesis of novel thieno[3,2-b]thienobis(silolothiophene) based low bandgap polymers for organic photovoltaics," Chemical Communications, Jan. 1, 2012, vol. 48, No. 62, pp. 7699-7701.

Lee, T. W. et al., "Heteroarene-fused [pi]-conjugated main-chain polymers containing 4,7-bis(4-octylthiophene-2-yl)benzo[c][1,2,5]thiazole or 2,5-bis(4-octylthiphen-2-yl)thiazolo[5,4-d]thiazole and their application to photovoltaic devices," Journal of Polymer Science Part A: Polymer Chemistry, Dec. 15, 2010, vol. 48, No. 24, pp. 5921-5929.

Bronstein, H. et al., "Synthesis of a Novel Fused Thiophene-thieno [3,2-b]thiophene-thiophene Donor Monomer and Co-polymer for Use in OPV and OFETs," Marcomolecular Rapid Communications, Oct. 18, 2011, vol. 32, No. 20, pp. 1664-1668.

* cited by examiner

POLYCYCLIC POLYMER COMPRISING THIOPHENE UNITS, A METHOD OF PRODUCING AND USES OF SUCH POLYMER

TECHNICAL FIELD

The present invention relates to a novel polycyclic polymer comprising fused thiophene units. The present invention also relates to a method for producing such polymer as well as the use of such polymer, particularly in organoelectronic applications.

BACKGROUND AND DESCRIPTION OF THE PRIOR ART

In recent years, organic semiconducting (OSC) materials have been developed in order to produce more versatile, lower cost electronic devices. Such materials find application in a wide range of devices or apparatus, including organic field effect transistors (OFETs), organic light emitting diodes (OLEDs), photodetectors, photovoltaic (PV) cells, sensors, memory elements and logic circuits to name just a few. The organic semiconducting materials are typically present in the electronic device in the form of a thin layer, for example of between 50 and 300 nm thickness.

The performance of OFET devices is principally based upon the charge carrier mobility of the semiconducting material and the current on/off ratio, so the ideal semiconductor should have a low conductivity in the off state, combined with high charge carrier mobility ($>1\times10^{-3}$ cm$^2$ V$^{-1}$ s$^{-1}$). In addition, it is important that the semiconducting material is stable to oxidation, i.e. it has a high ionisation potential, as oxidation leads to reduced device performance. Further requirements for the semiconducting material are good processability, especially for large-scale production of thin layers and desired patterns, and high stability, film uniformity and integrity of the organic semiconductor layer.

Promising compounds have been disclosed in for example S. Setayesh et al., *Macromolecules*, 2000, 33, 2016; W. Zhang et al., *J. Am. Chem. Soc.*, 2010, 132(33), 11437; Y.-J. Cheng et al., *Chem. Asian J.*, 2012, 7, 818; H. Bronstein et al, *Macromol. Rapid Commun.*, 2011, 32, 1664; 2: Y.-J. Cheng et al, *Chem. Commun.*, 2012, 48, 3203; WO 2012/058209; US 2012/283377; and B. C. Schroeder, *Chem. Commun.*, 2012, 48, 7699.

In prior art, various materials have been proposed for use as OSCs in OFETs, including small molecules like for example pentacene, and polymers like for example polyhexylthiophene. However, the materials and devices investigated so far still have several drawbacks, and their properties, especially the processability, charge-carrier mobility, on/off ratio and stability do still leave room for further improvement.

One aim of the present invention is to provide new organic semiconducting materials for use in electronic devices, which have advantageous properties, in particular good processability, high charge-carrier mobility, high on/off ratio, high oxidative stability and long lifetime in electronic devices. Another aim is to extend the pool of semiconducting materials available to the expert. Other aims of the present invention are immediately evident to the expert from the following detailed description.

SUMMARY

The present inventors have now surprisingly found that the above objects may be attained either individually or in any combination by the compound of the present application.

The present application therefore provides for a compound comprising a divalent unit selected from the group consisting of the following formula (I)

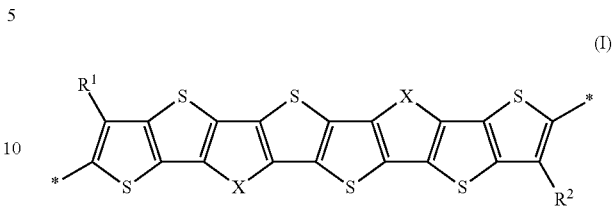

(I)

wherein $R^1$ and $R^2$ are independently of each other selected from the group consisting of H, halogen, carbyl and hydrocarbyl, and X is at each occurrence independently selected from the group consisting of $CR^3R^4$, $SiR^3R^4$, $GeR^3R^4$ and $C=CR^3R^4$, with $R^3$ and $R^4$ being independently of each other selected from the group consisting of hydrogen, carbyl and hydrocarbyl.

The present application also provides for a mixture or blend comprising one or more of said compound and one or more compounds or polymers having semiconducting, charge transport, hole transport, electron transport, hole blocking, electron blocking, electrically conducting, thermoelectric, photoconducting or light emitting properties.

Further, the present application provides for a formulation comprising said compound and an organic solvent.

Furthermore, the present application provides for the use of said compound as charge transport, semiconducting, electrically conducting, photoconducting or light emitting material in optical, electrooptical, electronic, thermoelectric, electroluminescent or photoluminescent components or devices.

The present application also provides for a method of using said compounds, wherein said method comprises the steps of
(a) providing said compound, and
(b) producing with said compound a charge transport, semiconducting, electrically conducting, photoconducting or light emitting material in optical, electrooptical, electronic, thermoelectric, electroluminescent or photoluminescent components or devices.

Additionally the present application provides for charge transport, semiconducting, electrically conducting, photoconducting or light emitting materials comprising said compound.

The present application also provides for a component or device comprising such compound, said component or device being selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (OSC), photodiodes, laser diodes, photoconductors, organic photodetectors (OPD), electrophotographic devices, electrophotographic recording devices, organic memory devices, sensor devices, charge injection layers, charge transport layers or interlayers in polymer light emitting diodes (PLEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

The present application further relates to conjugated polymers comprising one or more repeating units which comprise a unit of formula (I) and/or one or more groups selected from aryl and heteroaryl groups.

The invention further relates to monomers comprising a unit of formula (I) and further comprising one or more reactive groups which can be reacted to form a conjugated polymer as described herein.

The invention also relates to small molecules comprising a unit of formula (I) and one or more inert groups.

The invention further relates to the use of a polymer, formulation, mixture or polymer blend of the present invention as charge transport, semiconducting, electrically conducting, photoconducting or light emitting material, or in an optical, electrooptical, electronic, thermoelectric, electroluminescent or photoluminescent device, or in a component of such a device or in an assembly comprising such a device or component.

The optical, electrooptical, electronic, electroluminescent and photoluminescent devices include, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, laser diodes, Schottky diodes, photoconductors and photodetectors.

The components of the above devices include, without limitation, charge injection layers, charge transport layers, interlayers, planarizing layers, antistatic films, polymer electrolyte membranes (PEM), conducting substrates and conducting patterns.

The assemblies comprising such devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

DETAILED DESCRIPTION

For the purposes of the present application the terms "fused" and "annealed" are used synonymously.

For the purposes of the present application an asterisk ("*") denotes a linkage to an adjacent unit or group, and in case of an oligomer or a polymer it may denote a link to an adjacent repeating unit or to a terminal group of the polymer chain. The asterisk is further used to denote the ring atoms at which aromatic or heteroaromatic rings are fused to other aromatic or heteroaromatic rings.

The term "fusion atom" is used to indicate any atom of a fused ring system which is common to two or more rings (see Pure & Appl. Chem., Vol. 70, No. 1, pp. 143-216, 1988, particularly page 147).

For the purposes of the present application the term "substituted" is used to denote substitution, i.e. replacement of a hydrogen, by a substituent selected from the group consisting of halogen atoms, alkyl having from 1 to 10 carbon atoms, alkyl having from 1 to 10 carbon atoms wherein at least one of the hydrogen atoms is replaced by a halogen atom, aryl having from 5 to 20 ring atoms with the ring atoms being independently of each other selected from the group consisting of carbon and heteroatoms as defined below, and aryl having from 5 to 20 ring atoms with the ring atoms being independently of each other selected from the group consisting of carbon and heteroatoms as defined below and at least one hydrogen replaced by a halogen atom.

For the purposes of the present application the term "polymer" will be understood to mean a molecule of high relative molecular mass, the structure of which essentially comprises the multiple repetition of units derived, actually or conceptually, from molecules of low relative molecular mass (Pure Appl. Chem., 1996, 68, 2291). The term "oligomer" will be understood to mean a molecule of intermediate relative molecular mass, the structure of which essentially comprises a small plurality of units derived, actually or conceptually, from molecules of lower relative molecular mass (Pure Appl. Chem., 1996, 68, 2291). In a preferred meaning as used herein a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (Pure Appl. Chem., 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups or reactive groups that are attached to a monomer forming the polymer backbone which did not participate in the polymerisation reaction, like for example a group having the meaning of $R^e$ or $R^f$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and alkyl having from 1 to 10 carbon atoms.

As used herein, the terms "donor" or "donating" and "acceptor" or "accepting" will be understood to mean an electron donor and electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. Aug. 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, Concise Dictionary of Physics, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also Pure Appl. Chem., 1994, 66, 1134).

As used herein, the term "conjugated" will be understood to mean a compound (for example a polymer) that contains mainly C atoms with $sp^2$-hybridisation (or optionally also sp-hybridization), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound. See also International Union of Pure and Applied Chemistry, Compendium of Chemical Technology, Gold Book, Version 2.3.2, 19. Aug. 2012, pages 322-323.

As used herein, unless stated otherwise the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, chlorobenzene is used as solvent. The molecular weight distribution ("MWD"), which may also be referred to as polydispersity index ("PDI"), of a polymer is defined as the ratio $M_w/M_n$. The degree of polymerization, also referred to as total number of repeat units, m, will be understood to mean the number average degree of polymerization given as $m=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic radical moiety which comprises at least one carbon atom either without any non-carbon atoms (like for example —C≡C—), or optionally comprising one or more heteroatoms (for example carbonyl etc.).

The term "hydrocarbyl group" will be understood to mean a carbyl group that does additionally contain one or more H atoms and optionally contains one or more hetero atoms.

As used herein, the term "hetero atom" will be understood to mean an atom in an organic compound that is not a H- or C-atom, and preferably will be understood to mean N, O, S, P, Si, Se, As, Te or Ge.

A carbyl or hydrocarbyl group comprising a chain of 3 or more C atoms may be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 20 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

The term "aryl" as used herein preferably means a mono-, bi- or tricyclic aromatic group with 6 to 60 aromatic carbon ring atoms. The term "heteroaryl" as used herein preferably means a mono-, bi- or tricyclic aromatic group with 5 to 60 aromatic ring atoms, at least one of which is a heteroatom. Both, aryl and heteroaryl, may also comprise condensed rings and may optionally be substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, P-Sp-, optionally substituted silyl, or carbyl or hydrocarbyl with 1 to 40 C atoms that is optionally substituted and optionally comprises one or more hetero atoms, and is preferably alkyl, alkoxy, thiaalkyl, alkylcarbonyl, alkoxycarbonyl or alkoxycarbonyloxy with 1 to 20 C atoms that is optionally fluorinated, and R$^0$, R$^{00}$, X$^0$, P and Sp have the meanings given above and below.

Very preferred substituents L are selected from halogen, most preferably F, or alkyl, alkoxy, oxaalkyl, thioalkyl, fluoroalkyl and fluoroalkoxy with 1 to 12 C atoms or alkenyl, and alkynyl with 2 to 12 C atoms.

Especially preferred aryl and heteroaryl groups are phenyl, phenyl wherein one or more CH groups are replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above. Further examples of aryl and heteroaryl groups are those selected from the groups shown hereinafter.

An alkyl or alkoxy radical, i.e. where the terminal $CH_2$ group is replaced by —O—, can be straight-chain or branched. It is preferably straight-chain (or linear). Suitable examples of such alkyl and alkoxy radical are methyl, ethyl, propyl, butyl, pentyl, hexyl, heptyl, octyl, nonyl, decyl, undecyl, dodecyl, tridecyl, tetradecyl, pentadecyl, methoxy, ethoxy, propoxy, butoxy, pentoxy, hexoxy, heptoxy, octoxy, nonoxy, decoxy, undecoxy, dodecoxy, tridecoxy or tetradecoxy. Preferred alkyl and alkoxy radicals have 1, 2, 3, 4, 5, 6, 7, 8, 9, 10, 12, 14, 16 or 18 carbon atoms. Suitable examples of such preferred alkyl and alkoxy radicals may be selected from the group consisting of methyl, ethyl, propyl, butyl, pentyl, hexyl, heptyl, octyl, nonyl, decyl, dodecyl, tetradecyl, hexadecyl, octadecyl, methoxy, ethoxy, propoxy, butoxy, pentoxy, hexoxy, heptoxy, octoxy, nonoxy, decoxy dodecoxy, tetradecoxy, hexadecoxy and octadecoxy.

An alkenyl group, wherein one or more $CH_2$ groups are replaced by —CH=CH— can be straight-chain or branched. It is preferably straight-chain, has 2 to 18 C atoms and accordingly is preferably vinyl, prop-1-enyl, or prop-2-enyl, but-1-enyl, but-2-enyl or but-3-enyl, pent-1-enyl, pent-2-enyl, pent-3-enyl or pent-4-enyl, hex-1-enyl, hex-2-enyl, hex-3-enyl, hex-4-enyl or hex-5-enyl, hept-1-enyl, hept-2-enyl, hept-3-enyl, hept-4-enyl, hept-5-enyl or hept-6-enyl, oct-1-enyl, oct-2-enyl, oct-3-enyl, oct-4-enyl, oct-5-enyl, oct-6-enyl or oct-7-enyl, non-1-enyl, non-2-enyl, non-3-enyl, non-4-enyl, non-5-enyl, non-6-enyl, non-7-enyl or non-8-enyl, dec-1-enyl, dec-2-enyl, dec-3-enyl, dec-4-enyl, dec-5-enyl, dec-6-enyl, dec-7-enyl, dec-8-enyl or dec-9-enyl, dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl or dodec-11-enyl, tetradec-1-enyl, tetradec-2-enyl, tetradec-3-enyl, tetradec-4-enyl, tetradec-5-enyl, tetradec-6-enyl, tetradec-7-enyl, tetradec-8-enyl, tetradec-9-enyl, tetradec-10-enyl, tetradec-11-enyl, tetradec-12-enyl or tetradec-13-enyl, hexadec-1-enyl, hexadec-2-enyl, hexadec-3-enyl, hexadec-4-enyl, hexadec-5-enyl, hexadec-6-enyl, hexadec-7-enyl, hexadec-8-enyl, hexadec-9-enyl, hexadec-10-enyl, hexadec-11-enyl, hexadec-12-enyl, hexadec-13-enyl, hexadec-14-enyl or hexadec-15-enyl, octadec-1-enyl, octadec-2-enyl, octadec-3-enyl, octadec-4-enyl, octadec-5-enyl, octadec-6-enyl, octadec-7-enyl, octadec-8-enyl, octadec-9-enyl, octadec-10-enyl, octadec-11-enyl, octadec-12-enyl, octadec-13-enyl, octadec-14-enyl, octadec-15-enyl, octadec-16-enyl or octadec-17-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Alkenyl groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably selected from the group consisting of acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, and 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably selected from the group consisting of bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, and 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the CH$_2$ group adjacent to the sp$^2$ hybridised vinyl carbon atom is replaced.

A fluoroalkyl group is preferably perfluoroalkyl C$_i$F$_{2i+1}$, wherein i is an integer from 1 to 15, in particular CF$_3$, C$_2$F$_5$, C$_3$F$_7$, C$_4$F$_9$, C$_5$F$_{11}$, C$_6$F$_{13}$, C$_7$F$_{15}$ or C$_8$F$_{17}$, very preferably C$_6$F$_{13}$, or partially fluorinated alkyl, in particular 1,1-difluoroalkyl, all of which are straight-chain or branched.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-decyltetradecyl, 7-decylnonadecyl, 2-propylpentyl, in particular 2-methylbutyl, 2-methylbutoxy, 2-methylpentoxy, 3-methylpentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the hydrocarbyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

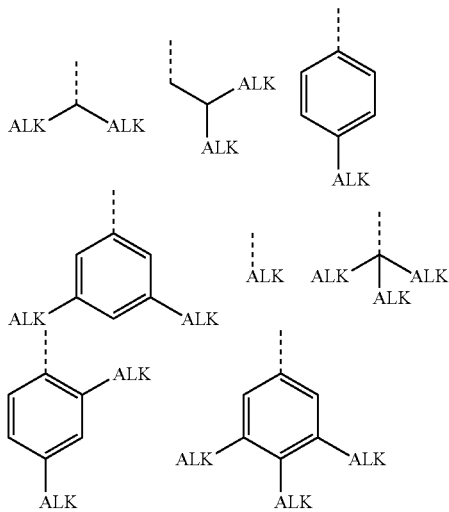

wherein "ALK" denotes optionally fluorinated, preferably linear, alkyl or alkoxy with 1 to 30, preferably 1 to 20 C-atoms, in case of tertiary groups very preferably 1 to 9 C atoms, and the dashed line denotes the link to the ring to which these groups are attached. Especially preferred among these groups are those wherein all ALK subgroups are identical.

—CY$^1$=CY$^2$— is preferably —CH=CH—, —CF=CF— or —CH=C(CN)—.

As used herein, "halogen" includes F, Cl, Br or I, preferably F, Cl or Br.

As used herein, —CO—, —C(=O)— and —C(O)— will be understood to mean a carbonyl group, i.e. a group having the structure

For the purposes of the present application R$^S$ is at each occurrence independently of each other chosen from the group consisting of F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms.

R$^0$ and R$^{00}$ are at each occurrence independently of each other H or optionally substituted C$_{1-40}$ carbyl or hydrocarbyl, and preferably denote H, alkyl with 1 to 12 C-atoms or phenyl.

X$^0$ is used to denote halogen, preferably F, Cl or Br.

The compounds, units and polymers according to the present invention may also be substituted with a polymerisable or crosslinkable reactive group P, which is optionally protected during the process of forming the polymer. Particular preferred groups P may be selected from the group consisting of CH$_2$=CW$^1$—C(O)—O—, CH$_2$=CW$^1$—C(O)—,

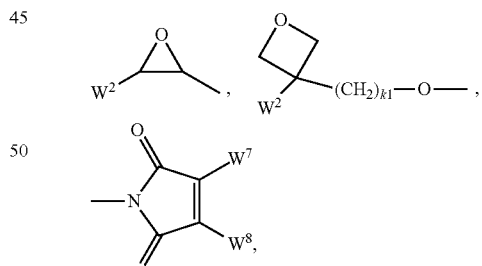

CH$_2$=CW$^2$—(O)$_{k1}$—, CW$^1$=CH—C(O)—(O)$_{k3}$—, CW$^1$=CH—C(O)—NH—, CH$_2$=CW$^1$—C(O)—NH—, CH$_3$—CH=CH—O—, (CH$_2$=CH)$_2$CH—OC(O)—, (CH$_2$=CH—CH$_2$)$_2$CH—O—C(O)—, (CH$_2$=CH)$_2$CH—O—, (CH$_2$=CH—CH$_2$)$_2$N—, (CH$_2$=CH—CH$_2$)$_2$N—C(O)—, HO—CW$^2$W$^3$—, HS—CW$^2$W$^3$—, HW$^2$N—, HO—CW$^2$W$^3$—NH—, CH$_2$=CH—(C(O)—O)$_{k1}$-Phe-(O)$_{k2}$—, CH$_2$=CH—(C(O))$_{k1}$-Phe-(O)$_{k2}$—, Phe-CH=CH—, HOOC—, OCN—, and W$^4$W$^5$W$^6$Si—, with W$^1$ being H, F, Cl, CN, CF$_3$, phenyl or alkyl with 1 to 5 C-atoms, in particular H, Cl or CH$_3$, W$^2$ and W$^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, k1, k2 and k3 being independently of each other 0 or 1, and k3 preferably being 1.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—C(O)—O—, $CH_2$=C($CH_3$)—C(O)—O—, $CH_2$=CF—C(O)—O—, $CH_2$=CH—O—, $(CH_2$=CH$)_2$CH—O—C(O)—, $(CH_2$=CH$)_2$CH—O—,

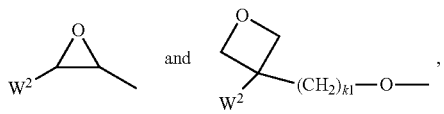

or protected derivatives thereof.

Further preferred groups P are selected from the group consisting of vinyloxy, acrylate, methacrylate, fluoroacrylate, chloracrylate, oxetan and epoxy groups, very preferably from an acrylate or methacrylate group.

Polymerisation of group P can be carried out according to methods that are known to the ordinary expert and described in the literature, for example in D. J. Broer; G. Challa; G. N. Mol, *Macromol. Chem.*, 1991, 192, 59.

The term "spacer group" is known in prior art and suitable spacer groups Sp are known to the ordinary expert (see e.g. *Pure Appl. Chem.*, 2011, 73(5), 888. The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —C(O)—, —C(O)O—, —OC(O)—, —OC(O)—O—, —S—C(O)—, —C(O)—S—, —CH=CH— or —C≡C— in such a manner that O and/or S atoms are not linked directly to one another, X' is —O—, —S—, —C(O)—, —C(O)O—, —OC(O)—, —O—C(O)O—, —C(O)—$NR^0$—, —$NR^0$—C(O)—, —$NR^0$—C(O)—$NR^{00}$—, —$OCH_2$—, —$CH_2$O—, —$SCH_2$—, —$CH_2S$—, —$CF_2$O—, —$OCF_2$—, —$CF_2S$—, —$SCF_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C—, —CH=CH—C(O)O—, —OC(O)—CH=CH— or a single bond, $R^0$ and $R^{00}$ are as defined above; and $Y^1$ and $Y^2$ are independently of each other H, F, Cl or CN.

X' is preferably —O—, —S—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —$CY^1$=$CY^2$—, —C≡C— or a single bond, in particular —O—, —S—, —C≡C—, —$CY^1$=$CY^2$— or a single bond. In another preferred embodiment X' is a group that is able to form a conjugated system, such as —C≡C— or —$CY^1$=$CY^2$—, or a single bond.

Typical groups Sp' are, for example, —$(CH_2)_p$—, —$(CH_2CH_2O)_q$—$CH_2CH_2$—, —$CH_2CH_2$—S—$CH_2CH_2$— or —$CH_2CH_2$—NH—$CH_2CH_2$— or —$(SiR^0R^{00}$—O$)_p$—, with p being an integer from 2 to 12, q being an integer from 1 to 3 and $R^0$ and $R^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Compound

The compound of the present invention comprises a divalent unit of the following formula (I)

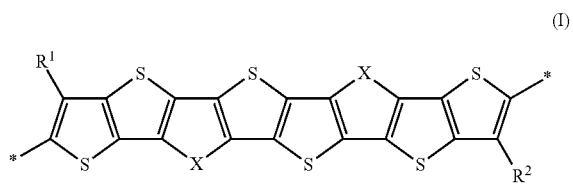

wherein $R^1$ and $R^2$ are independently of each other selected from the group consisting of H, halogen, carbyl and hydrocarbyl, and X is at each occurrence independently selected from the group consisting of $CR^3R^4$, $SiR^3R^4$, $GeR^3R^4$ and C=$CR^3R^4$.

With regards to $R^1$ and $R^2$ preferred halogen is selected from the group consisting of F, Cl, Br and I, of which F is most preferred.

With regards to $R^1$ and $R^2$ preferred carbyl and hydrocarbyl are selected from the group consisting of alkyl having from 1 to 20 carbon atoms, and more preferably form the group consisting of alkyl having from 1 to 10 carbon atoms. Examples of such alkyl having from 1 to 10 carbon atoms are methyl, ethyl, n-propyl, iso-propyl, n-butyl, iso-butyl, tert-butyl, pentyl, hexyl, heptyl, octyl, nonyl and decyl.

Preferably X is $CR^3R^4$ or $SiR^3R^4$. Most preferably X is $CR^3R^4$.

$R^3$ and $R^4$ are independently of each other selected from the group consisting of hydrogen, carbyl and hydrocarbyl.

Preferably, $R^3$ and $R^4$ are independently of each other selected from the group consisting of hydrogen, alkyl having from 1 to 20 carbon atoms, aryl having from 6 to 30 aromatic ring atoms and heteroaryl having from 5 to 30 aromatic ring atoms.

Preferably, the compound of the present invention comprises a divalent unit of the following formula (Ia)

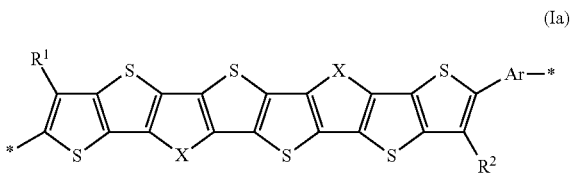

wherein Ar comprises an aromatic ring system comprising from 6 to 60 aromatic carbon atoms, or a heteroaromatic ring system comprising from 5 to 60 aromatic ring atoms, at least one of which is a heteroatom, and wherein $R^1$, $R^2$ and X are as defined above. It is particularly preferred that Ar is selected from the group consisting of formulae (D1) to (132) and (A1) to (A93).

Compounds comprising the structural unit of formulae (I) and (Ia) as defined above may preferably be selected from the group consisting of small molecules, monomers and polymers. As used herein, the term "small molecule" will be used to denote a compound comprising a structural unit of formulae (I) or (Ia) and two inert chemical groups, which are inert under use condition and thus inhibit such a small molecule from being polymerized. In contrast hereto, the term "monomer" is used to denote a compound comprising a structural unit of formulae (I) or (Ia) and at least one reactive chemical group, which allows such monomer to be reacted so as to form part of a polymer.

Without wishing to be bound by theory it is believed that the introduction of a divalent unit in accordance with the present application, for example into a homopolymer, raises the energy level of the HOMO (highest occupied molecular orbital) when compared to an indenofluorene homopolymer. This should result in improved charge-injection into the polymer when applied as an organic semiconductor in transistor devices. Additionally, the HOMO of a homopolymer of the divalent unit in accordance with the present application is believed to be inherently lower than that of P3HT (poly(3-hexylthiophene)) and other polythiophene materials, so that the resulting polymer has improved oxidative stability.

The present compounds may be synthesized from commercially available starting materials or from materials that are readily accessible by standard synthetic procedures described in the literature. Exemplary syntheses are also illustrated below.

Small Molecule and Monomer

In one aspect the present application provides for a small molecule, i.e. for a compound comprising a structural unit selected from the group consisting of formulae (I) and (Ia), and two inert chemical groups $R^a$ and $R^b$. Such a small molecule may for example be represented by formula (II-a)

$$R^a\text{-M-}R^b \qquad\qquad \text{(II-a)}$$

wherein M comprises a structural unit selected from the group consisting of formulae (I) and (Ia), and $R^a$ and $R^b$ are inert chemical groups. Such inert chemical groups $R^a$ and $R^b$ may independently of each other for example be chosen from the group consisting of hydrogen, fluorine, alkyl having from 1 to 10 carbon atoms, fluoroalkyl having from 1 to 10 carbon atoms, aromatic ring systems of from 6 to 30 carbon atoms and aromatic ring systems of from 5 to 30 carbon atoms wherein one or more hydrogen atom may independently of each other be replaced by fluorine or alkyl having from 1 to 10 carbon atoms.

An exemplary synthesis of a small molecule of general formula (II-a) is illustrated schematically in Scheme 1, wherein R* may for example be as defined for L above, R may for example be as defined for $Z^4$ herein.

Scheme 1

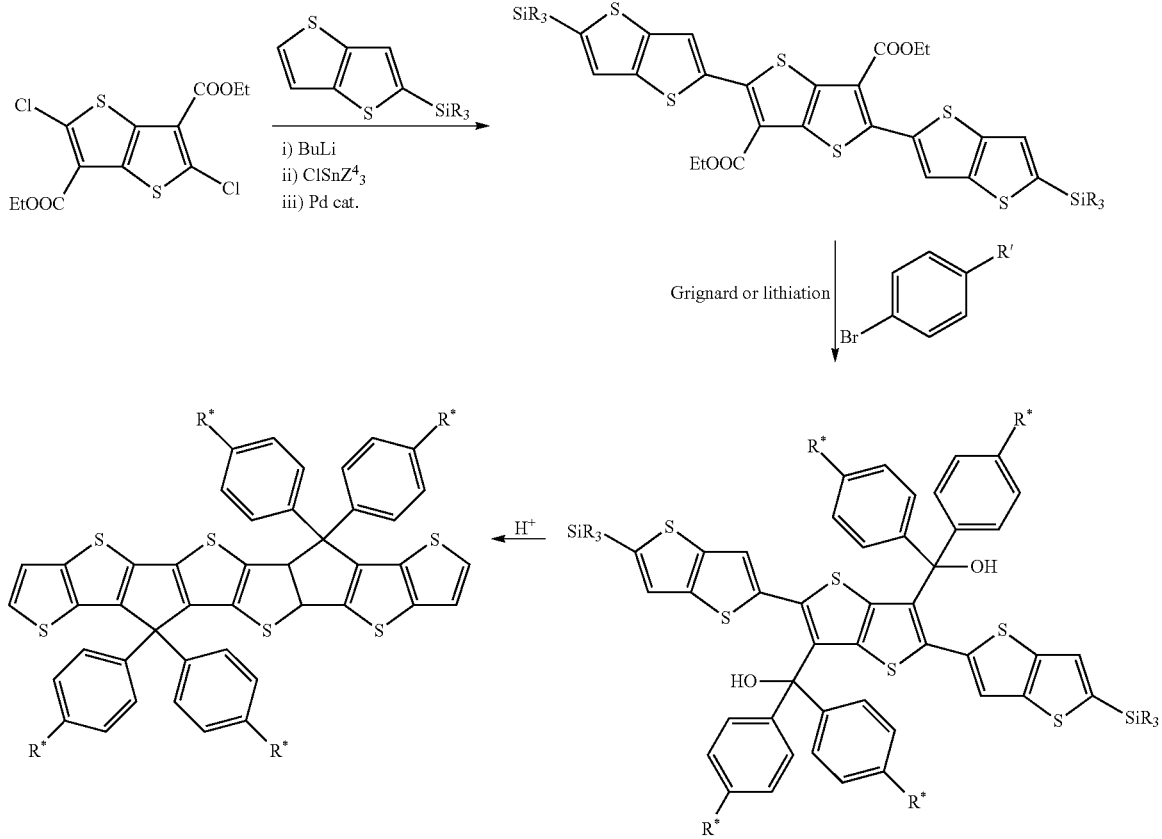

In another aspect the present application provides for a monomer, i.e. for a compound comprising a structural unit selected from the group consisting of formulae (I) and (Ia), and at least one reactive chemical group $R^c$ which may be selected from group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is as defined above, and Z$^1$, Z$^2$, Z$^3$ and Z$^4$ are selected from the group consisting of alkyl and aryl, each being optionally substituted, and two groups Z$^2$ may also together form a cyclic group. Alternatively such a monomer may comprise two reactive chemical groups and is for example represented by formula (II-b)

$$R^c\text{-M-}R^d \qquad \text{(II-b)}$$

wherein M comprises a structural unit of formulae (I) or (Ia), and $R^c$ and $R^d$ are reactive chemical groups as defined above for $R^c$.

Exemplary reactions for synthesizing a monomer of formula (II-b) starting from a small molecule of formula (II-a) are shown schematically in Scheme 2, wherein NBS denotes N-bromosuccinimide and $Z^4$ is as defined herein.

from 1 to 12 carbon atoms. Optionally, said alkyl may be partially or completely fluorinated.

Preferred small molecules and monomers are those with M selected from one of the following formulae (III-a-1) and (III-a-2)

$$*\text{—Ar}^a{}_{m2}\text{—U}^b\text{—Ar}^b{}_{m4}\text{—}* \qquad \text{(III-a-1)}$$

$$*\text{—U}^a{}_{m1}\text{—Ar}^a{}_{m2}\text{—U}^b{}_{m3}\text{—}* \qquad \text{(III-a-2)}$$

with Ar$^a$, Ar$^b$, U$^a$, U$^b$, m1, m2, m3 and m4 as defined above.

Especially preferred small molecules and monomers are those with M selected from one of the following formulae (III-b-1) to (III-b-5)

$$*\text{—Ar}^a\text{—U}^a\text{—Ar}^b\text{—}* \qquad \text{(III-b-1)}$$

$$*\text{—U}^a\text{—}* \qquad \text{(III-b-2)}$$

$$*\text{—Ar}^a\text{—U}^a\text{—}* \qquad \text{(III-b-3)}$$

$$*\text{—U}^a\text{—Ar}^b\text{—}* \qquad \text{(III-b-4)}$$

$$*\text{—U}^a\text{—Ar}^a\text{—U}^b\text{—}* \qquad \text{(III-b-5)}$$

with Ar$^a$, Ar$^b$, U$^a$ and U$^b$ as defined above.

Scheme 2

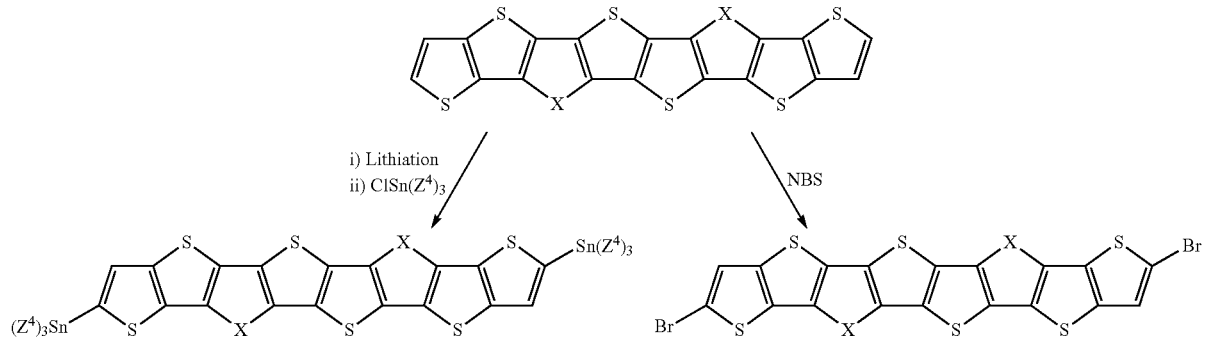

Preferably, M in formulae (II-a) and (II-b) may further comprise one or more (for example 2, 3, 4, 5, 6, 7, 8, 9 or 10) aryl or heteroaryl as defined above. Preferred examples of M comprise, preferably consist of, the following $$*\text{—U}^a{}_{m1}\text{—Ar}^a{}_{m2}\text{—U}^b{}_{m3}\text{—Ar}^b{}_{m4}\text{—Ar}^c{}_{m5}\text{—}* \qquad \text{(III)}$$

wherein

U$^a$ and U$^b$ are independently of each other selected from the divalent unit selected from the group consisting of formulae (I) and (Ia);

Ar$^a$, Ar$^b$ and Ar$^c$ are independently of each other aryl or heteroaryl different from U$^a$ and U$^b$;

m1, m2, m3 and m4 are independently of each other selected from the group consisting of 0, 1 and 2, with the provision that at least one of m1 and m3 is not 0; and m5 is 0 or an integer from 1 to 10 (for example 2, 3, 4, 5, 6, 7, 8 or 9).

Preferably Ar$^a$, Ar$^b$ and Ar$^c$ are selected from aryl having from 5 to 60 aromatic carbon atoms and heteroaryl having from 5 to 60 aromatic ring atoms, at least one of which is a heteroatom. Said aryl and heteroaryl may optionally be substituted with at least one substituent L as defined earlier. Preferred substituents L are selected from alkyl having from 1 to 20 carbon atoms, more preferably from alkyl having Particularly preferred examples of M of formulae (III), (III-a-1), (III-a-2) and (III-b-1) to (III-b-5) are those wherein one or more of Ar$^a$, Ar$^b$ and Ar$^c$ denote aryl or heteroaryl, preferably having electron donor properties or electron acceptor properties.

Suitable examples of aryl and heteroaryl with electron donor properties may be selected from the group consisting of the following formulae (D1) to (D132)

(D1)

(D2)

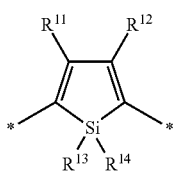
(D3)
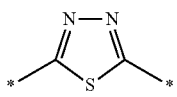
(D4)
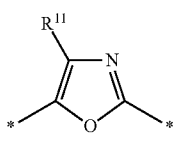
(D5)
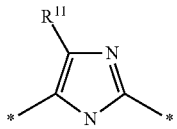
(D6)
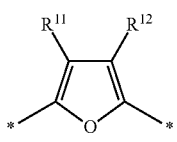
(D7)
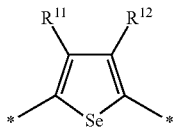
(D8)
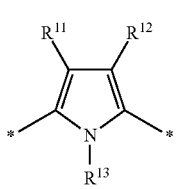
(D9)
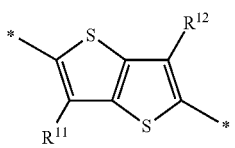
(D10)
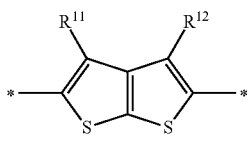
(D11)
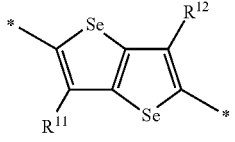
(D12)
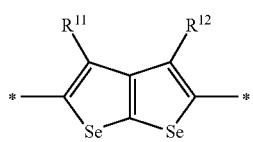
(D13)
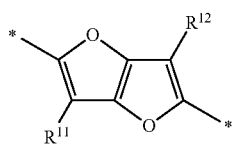
(D14)
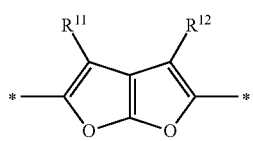
(D15)
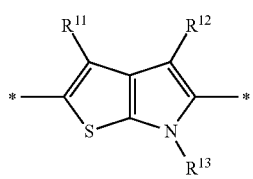
(D16)
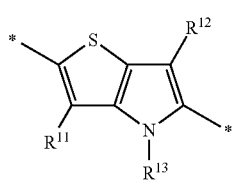
(D17)
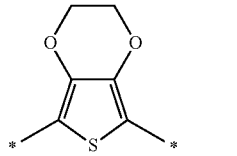
(D18)
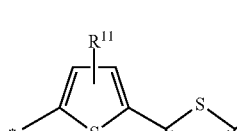
(D19)
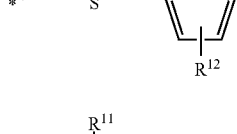
(D20)
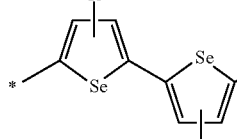
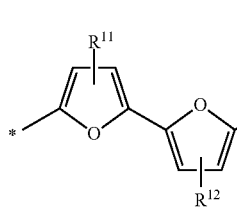
(D21)

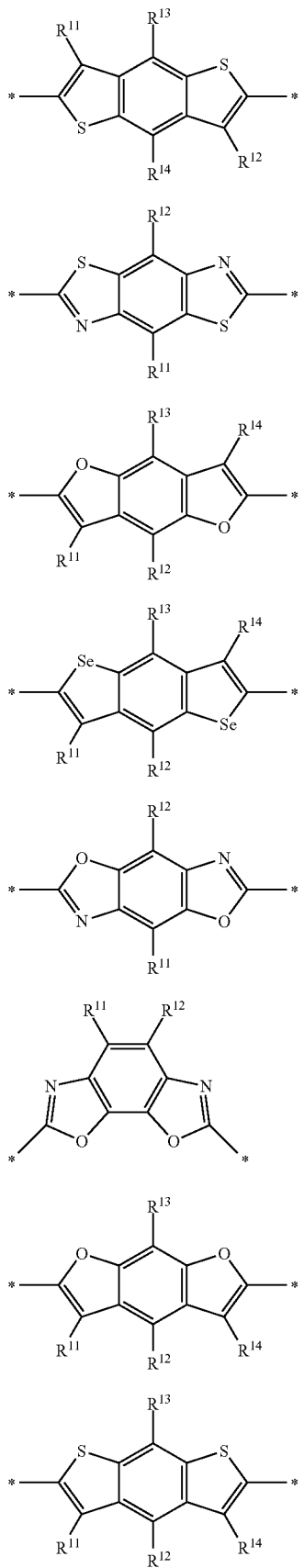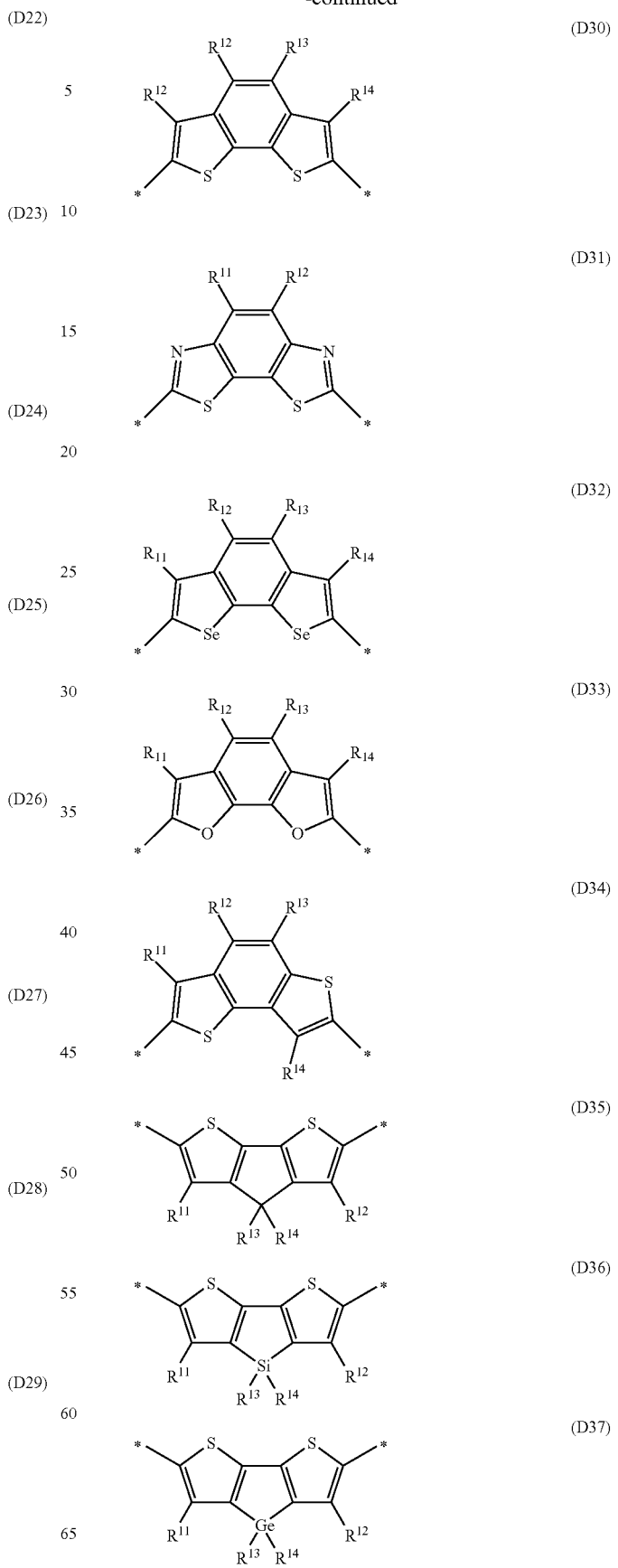

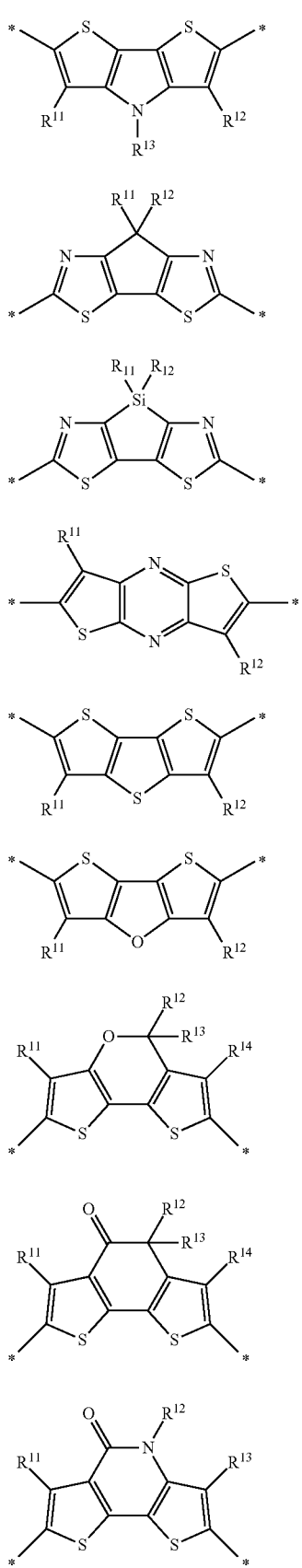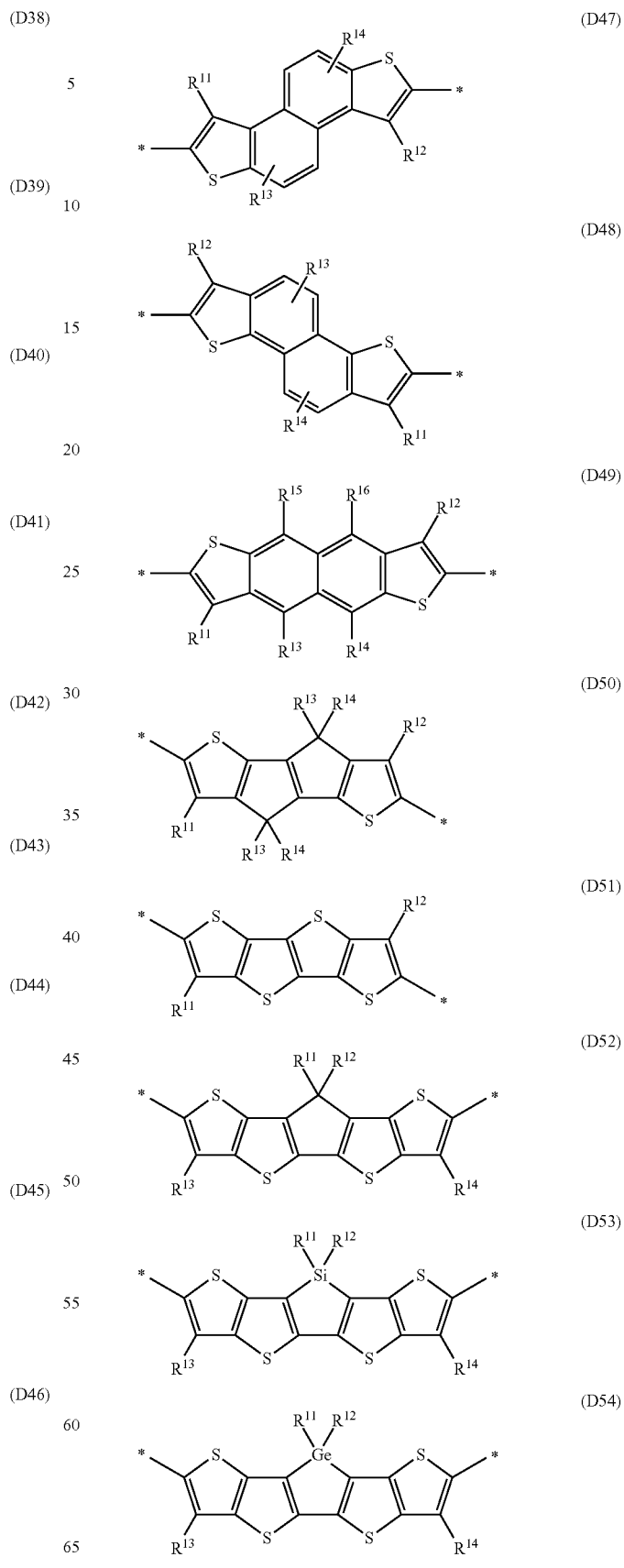

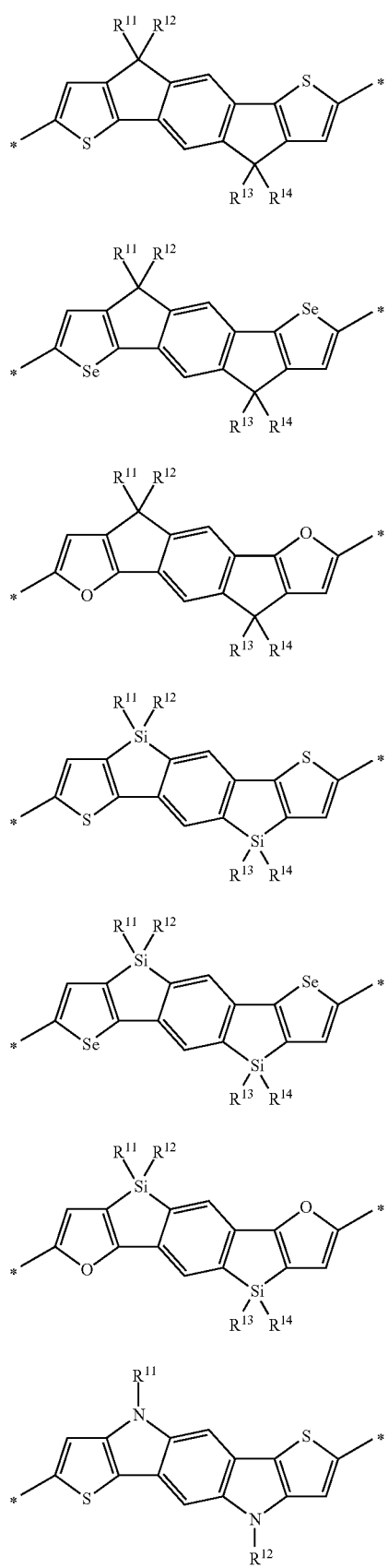
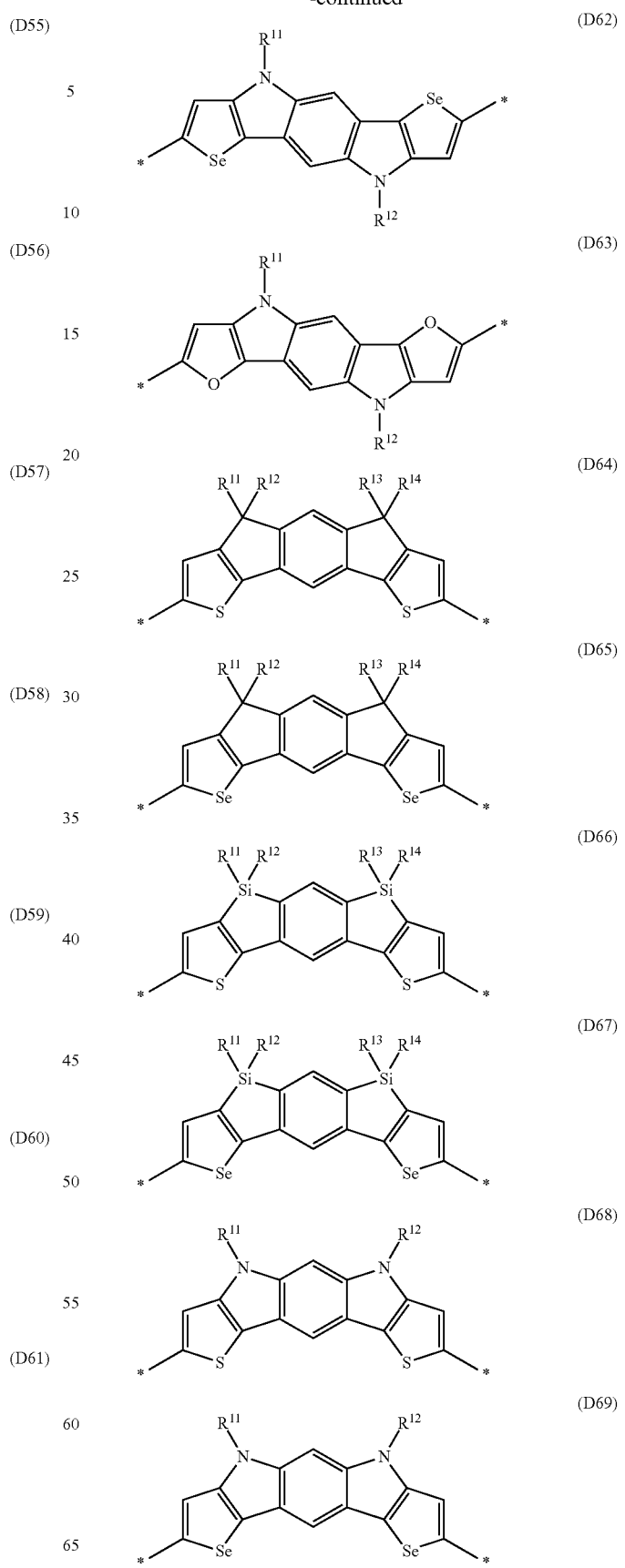

-continued
(D70)
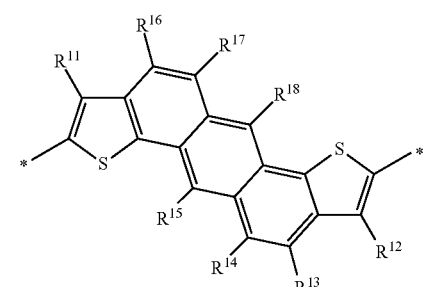
(D71)
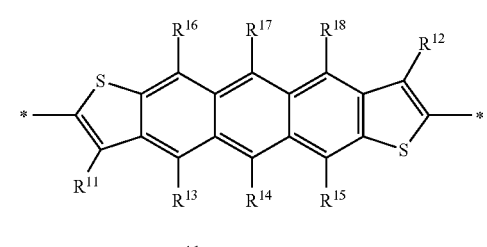
(D72)
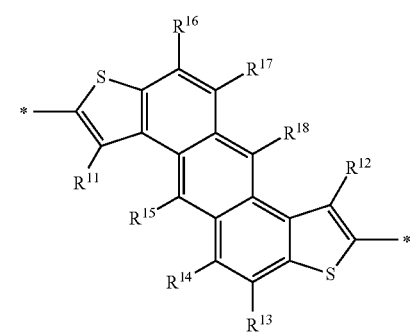
(D73)
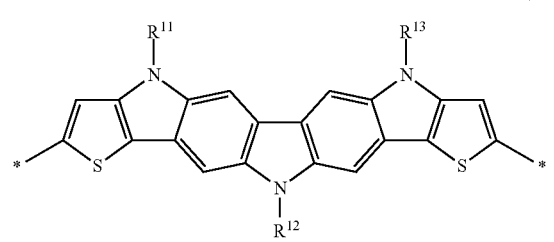
(D74)
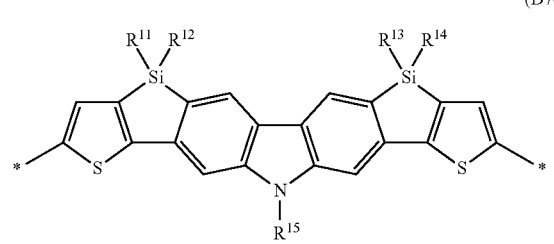
(D75)
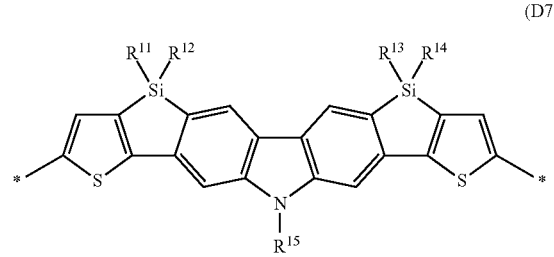
-continued
(D76)
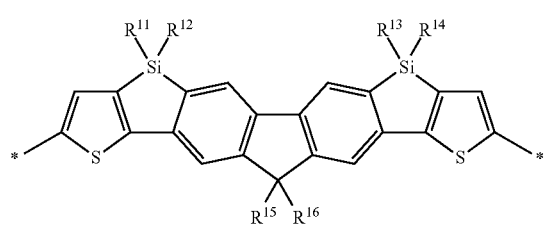
(D77)
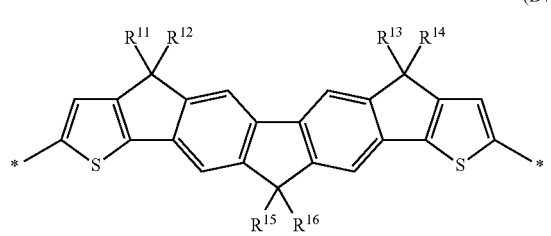
(D78)
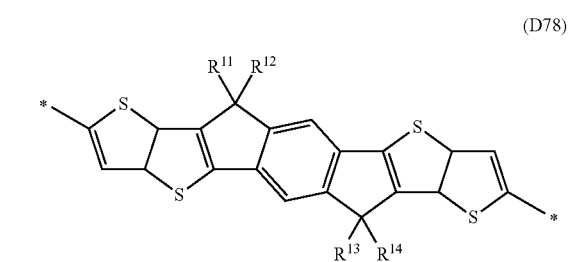
(D79)
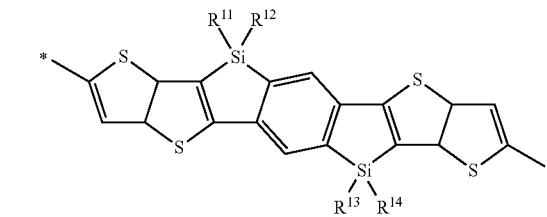
(D80)
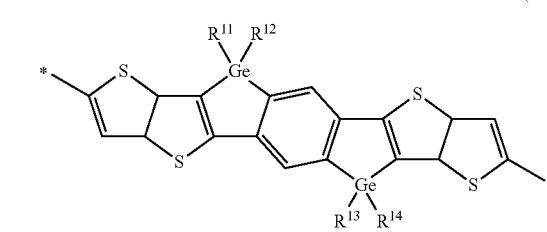
(D81)
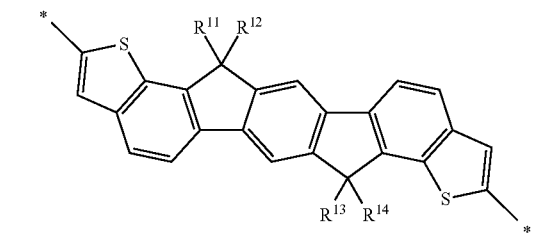

(D82) 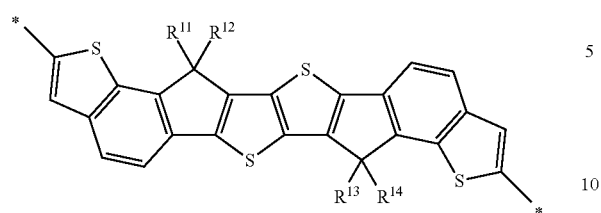
(D83) 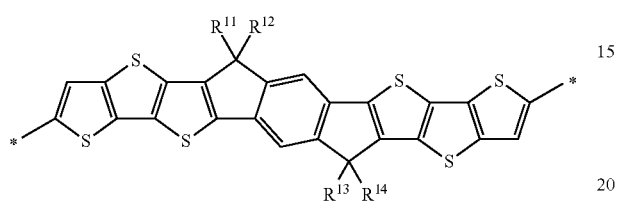
(D84) 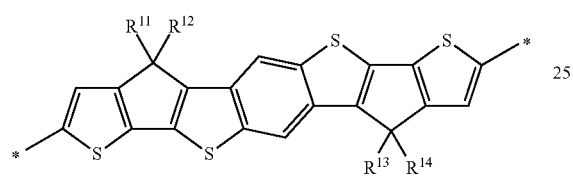
(D85) 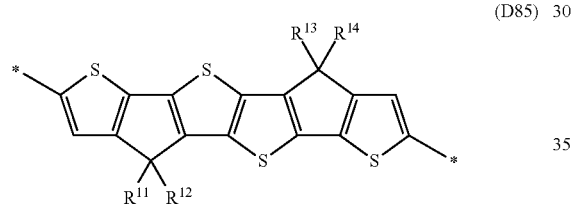
(D86) 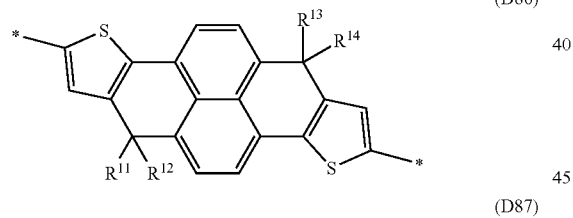
(D87) 
(D88) 
(D89) 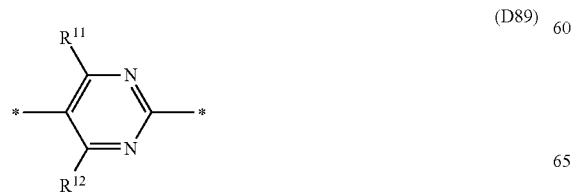
(D90) 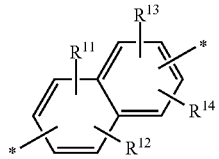
(D91) 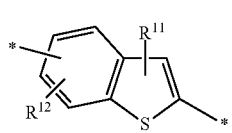
(D92) 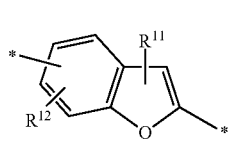
(D93) 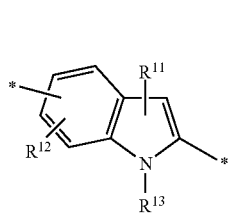
(D94) 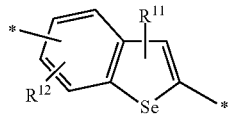
(D95) 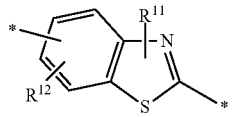
(D96) 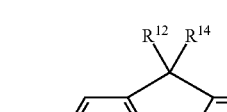
(D97) 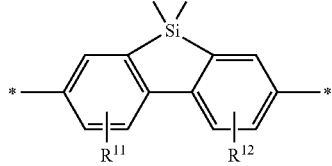
(D98) 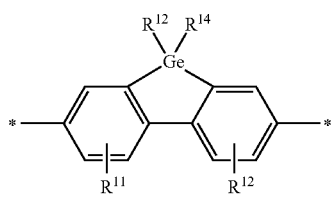

-continued
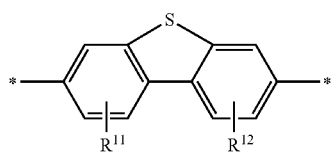
(D99)
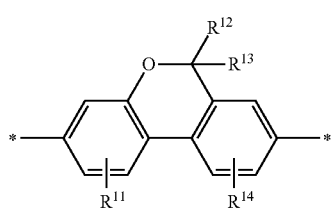
(D100)
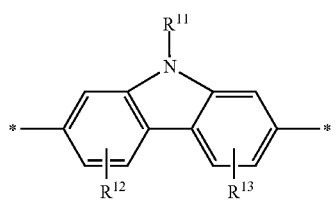
(D101)
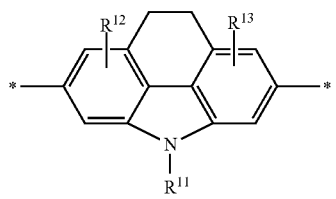
(D102)
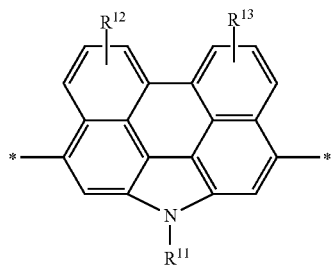
(D103)
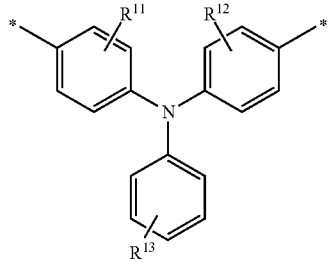
(D104)
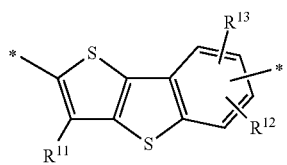
(D105)
-continued
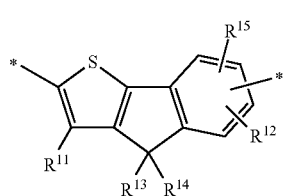
(D106)
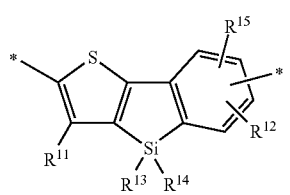
(D107)
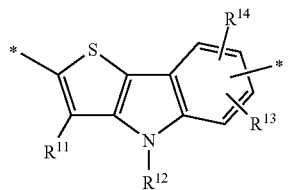
(D108)
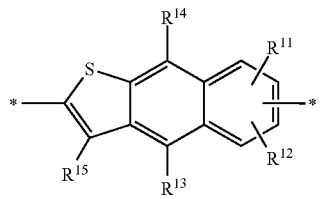
(D109)
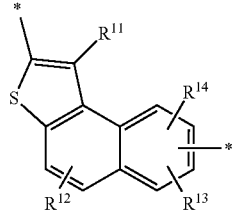
(D110)
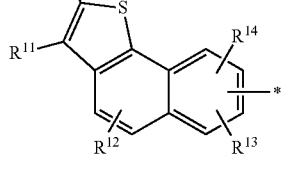
(D111)
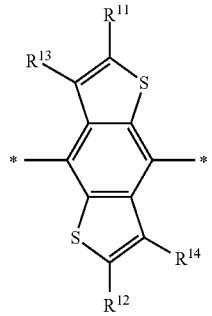
(D112)

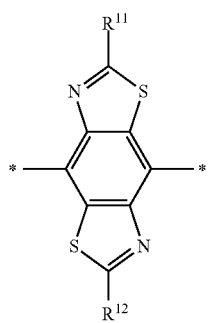
(D113)
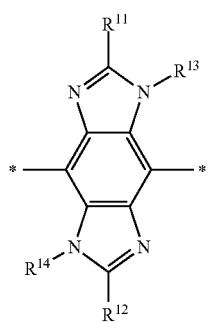
(D114)
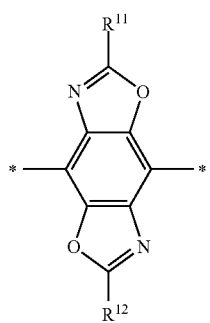
(D115)
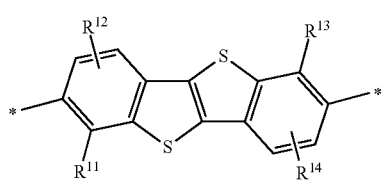
(D116)
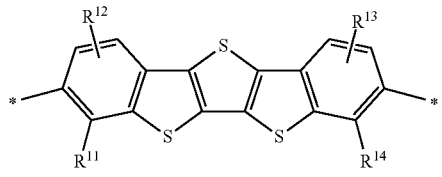
(D117)
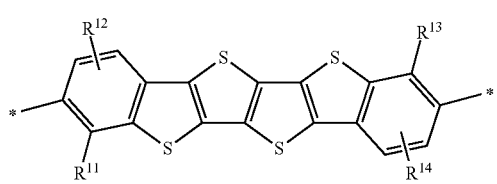
(D118)
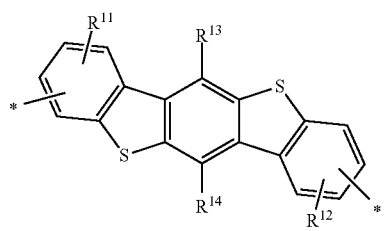
(D119)
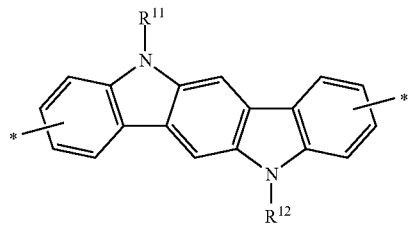
(D120)
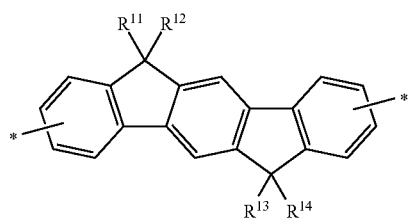
(D121)
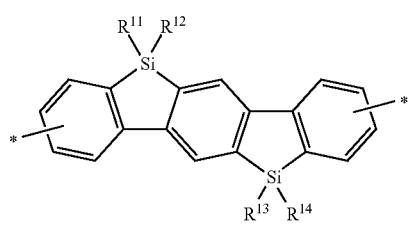
(D122)
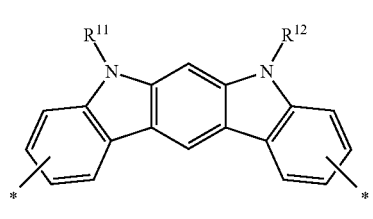
(D123)
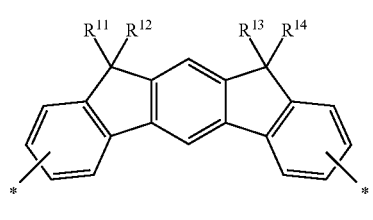
(D124)
(D125)

-continued

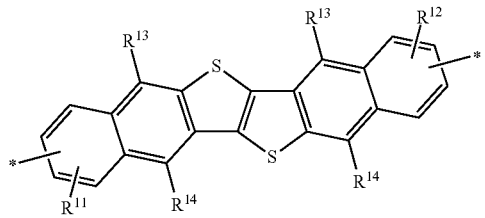
(D126)

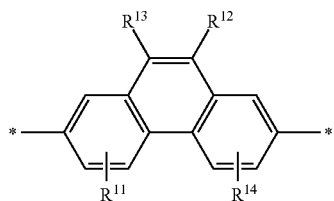
(D127)

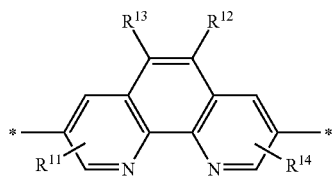
(D128)

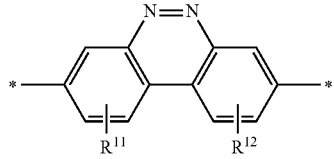
(D129)

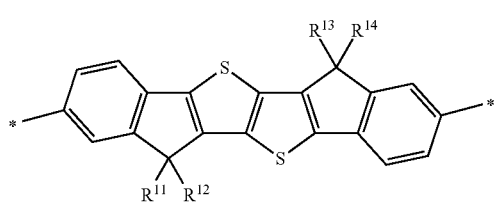
(D130)

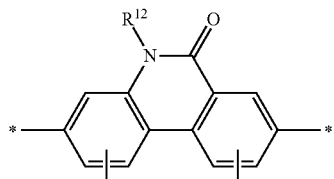
(D131)

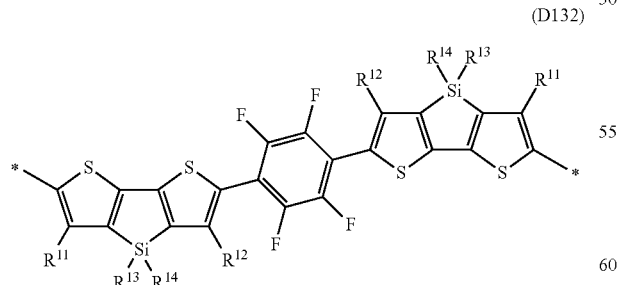
(D132)

wherein $R^{11}$, $R^{12}$, $R^{13}$, $R^{14}$, $R^{15}$, $R^{16}$, $R^{17}$ and $R^{18}$ are independently of each other selected from the group consisting of hydrogen, F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, optionally substituted silyl or hydrocarbyl with 1 to 40 C atoms that is optionally substituted and optionally comprises one or more hetero atoms, with X°, R° and R°° as defined earlier. Of these (D1), (D10), and (D19), wherein $R^{11}$ and $R^{12}$ are independently of each other hydrogen or fluorine, are preferred.

Suitable examples of aryl and heteroaryl with electron acceptor properties may be selected from the group consisting of the following formula (A1) to (A93)

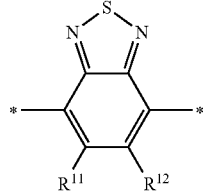
(A1)

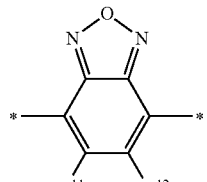
(A2)

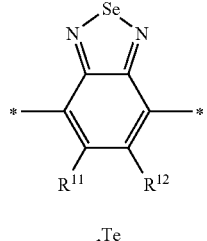
(A3)

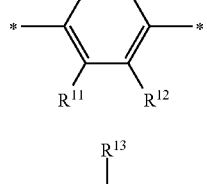
(A4)

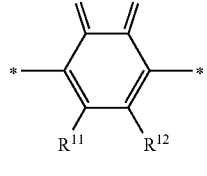
(A5)

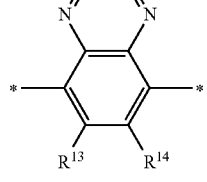
(A6)

-continued
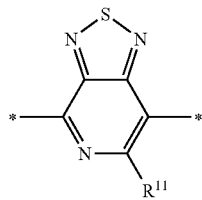 (A7)
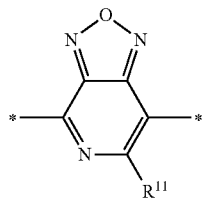 (A8)
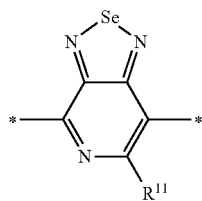 (A9)
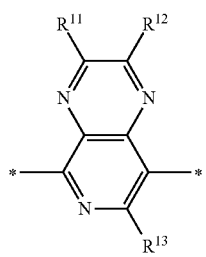 (A10)
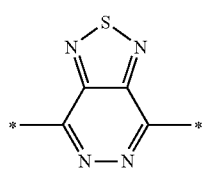 (A11)
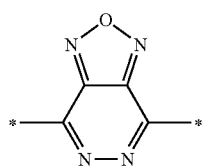 (A12)
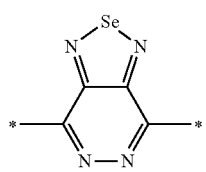 (A13)
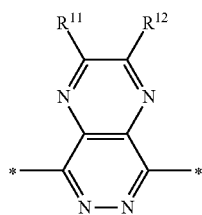 (A14)
-continued
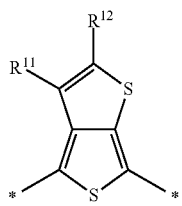 (A15)
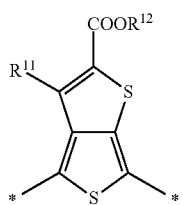 (A16)
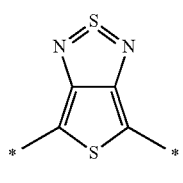 (A17)
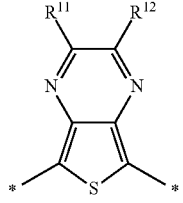 (A18)
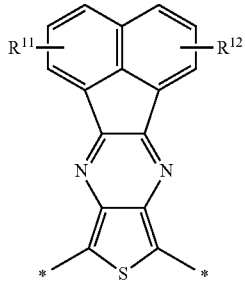 (A19)
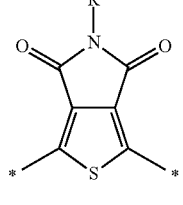 (A20)
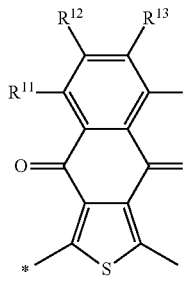 (A21)

-continued
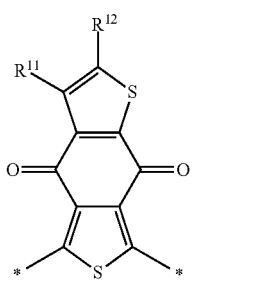
(A22)
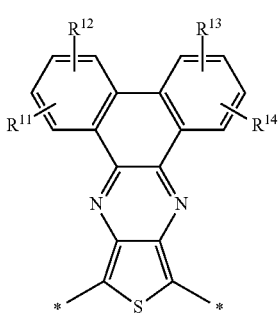
(A23)
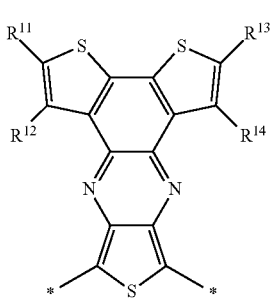
(A24)
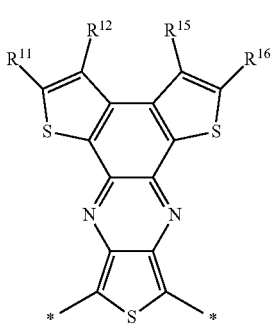
(A25)
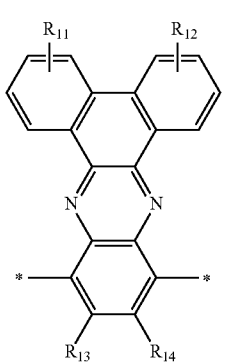
(A26)
-continued
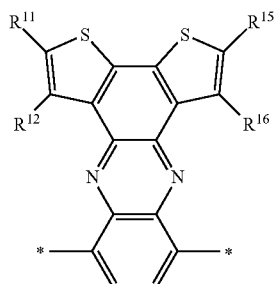
(A27)
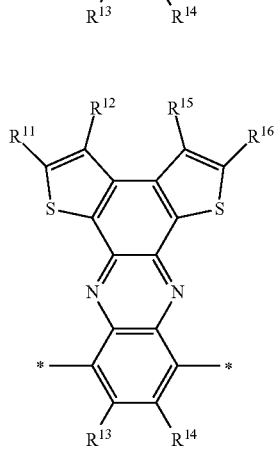
(A28)
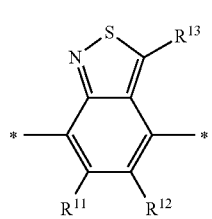
(A29)
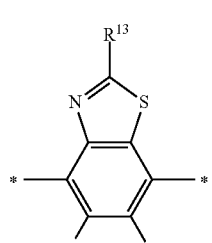
(A30)
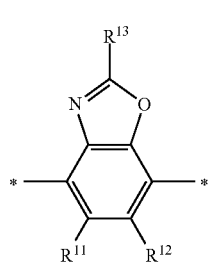
(A31)

(A32) 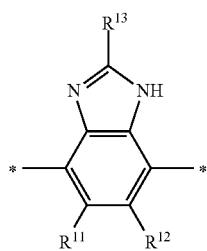
(A33) 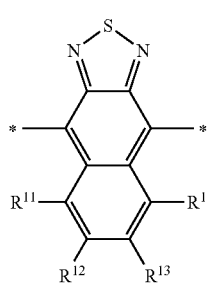
(A34) 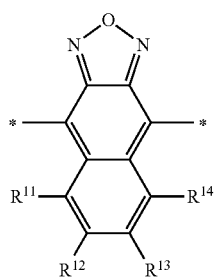
(A35) 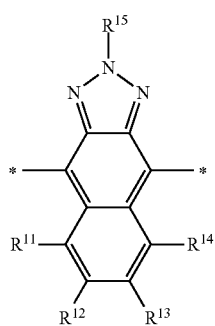
(A36) 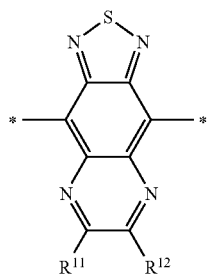
(A37) 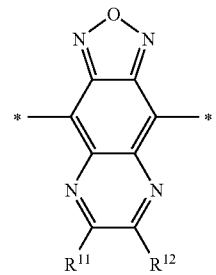
(A38) 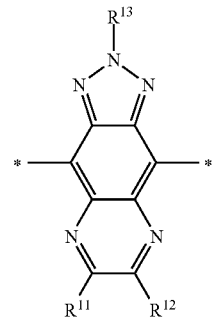
(A39) 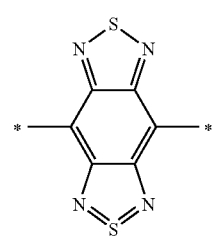
(A40) 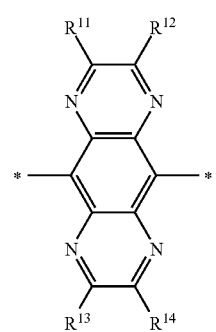
(A41) 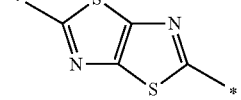
(A42) 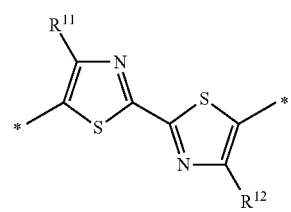
(A43) 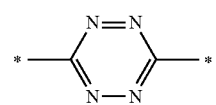

-continued
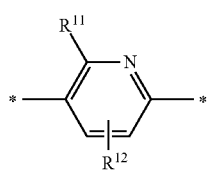
(A44)
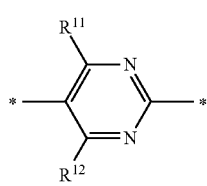
(A45)
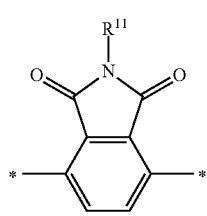
(A46)
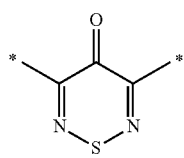
(A47)
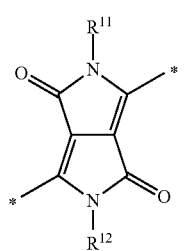
(A48)
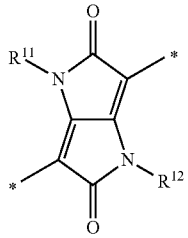
(A49)
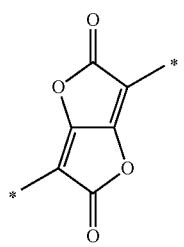
(A50)
-continued
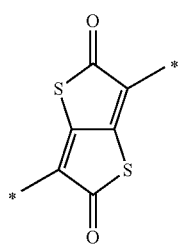
(A51)
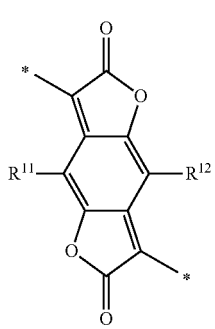
(A52)
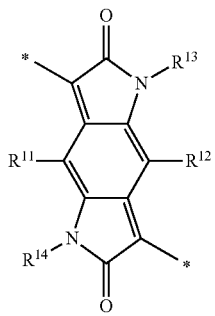
(A53)
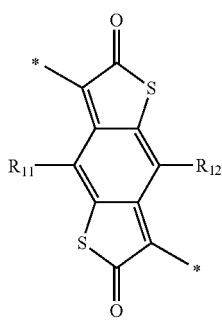
(A54)
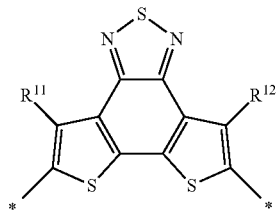
(A55)

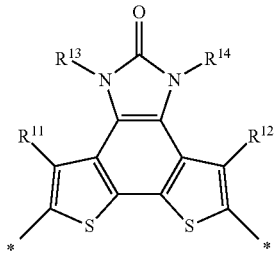
(A56)
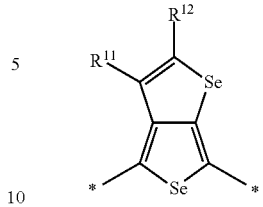
(A61)
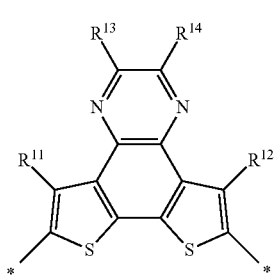
(A57)
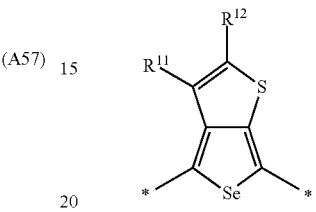
(A62)
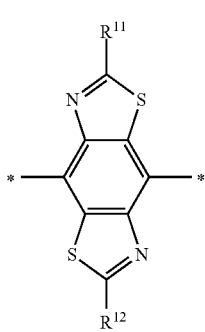
(A58)
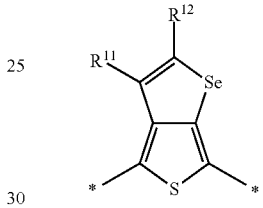
(A63)
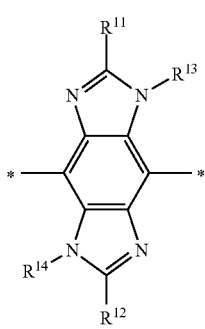
(A59)
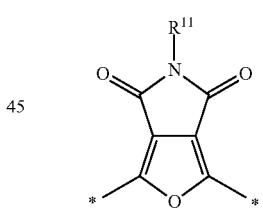
(A64)
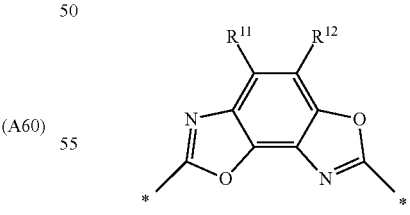
(A65)
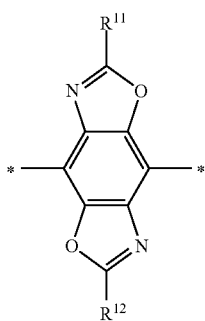
(A60)
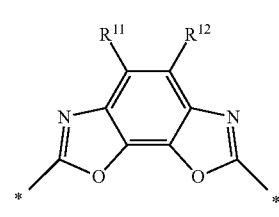
(A66)
(A67)

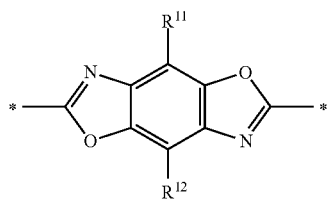
(A68)
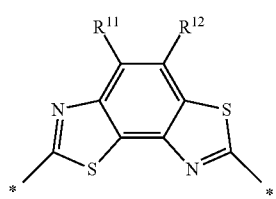
(A69)
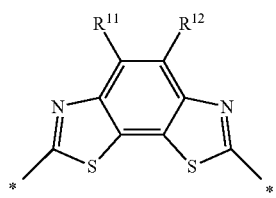
(A70)
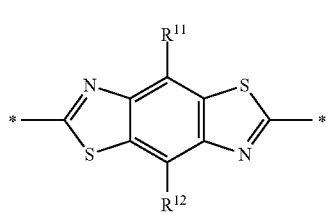
(A71)
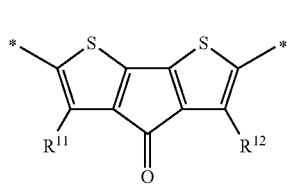
(A72)
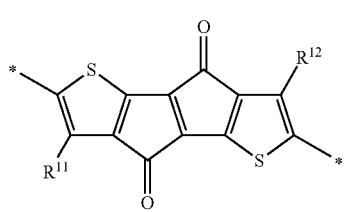
(A73)
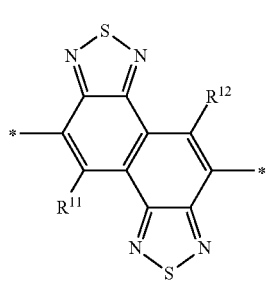
(A74)
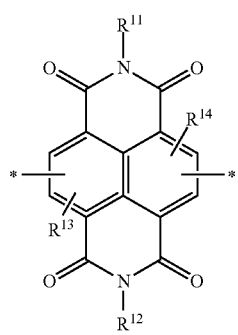
(A75)
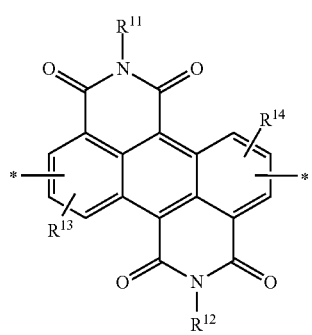
(A76)
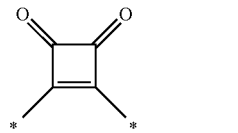
(A77)
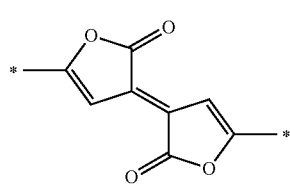
(A78)
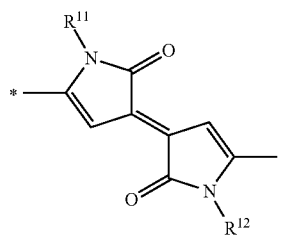
(A79)
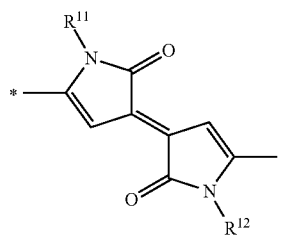
(A80)

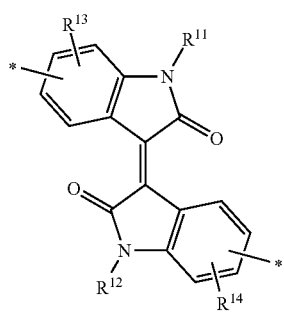
(A81)
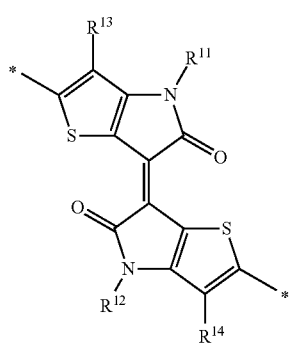
(A82)
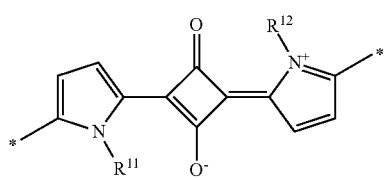
(A83)
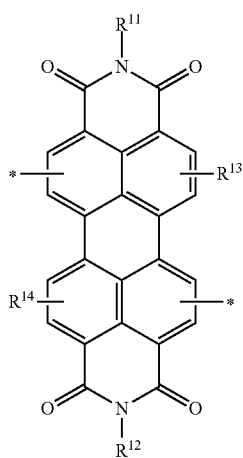
(A84)
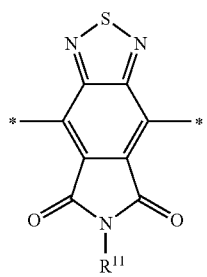
(A85)
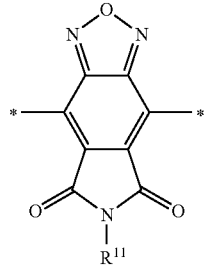
(A86)
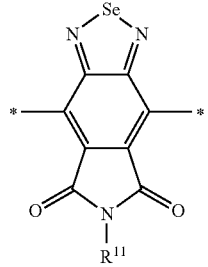
(A87)
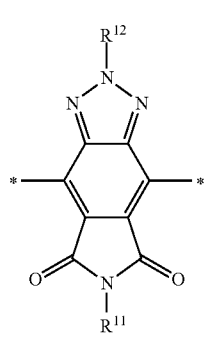
(A88)
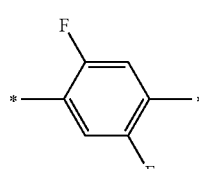
(A89)
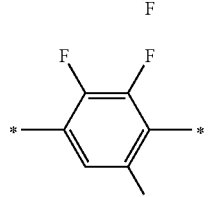
(A90)
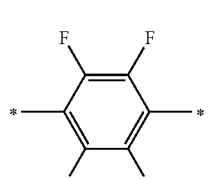
(A91)
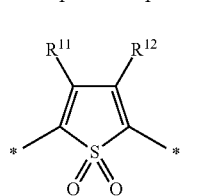
(A92)

-continued

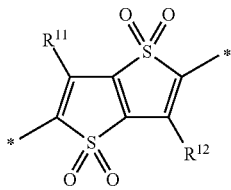

(A93)

wherein $R^{11}$, $R^{12}$, $R^{13}$, $R^{14}$, $R^{15}$ and $R^{16}$ are independently of each other selected from the group consisting of hydrogen, F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl or hydrocarbyl with 1 to 40 C atoms that is optionally substituted and optionally comprises one or more hetero atoms, with X$^0$, R$^0$ and R$^{00}$ as defined earlier. Of these (A1) and (A19), wherein $R^{11}$ and $R^{12}$ are independently of each other hydrogen or fluorine, are preferred.

Polymer

In a further aspect the present application provides for an oligomer or polymer, i.e. for a compound comprising more than one structural unit selected from the group consisting of formulae (I) and (Ia). Preferably such oligomer or polymer comprises more than one group M as defined in any one of formulae (III), (III-a-1), (III-a-2) and (III-b-1) to (III-b-5). At each occurrence M may be the same or different.

Optionally, such oligomer or polymer may further comprise a repeating unit comprising a group selected from monocyclic or polycyclic aryl or heteroaryl groups that are optionally substituted. Preferably such further repeating units are selected from one of the following

*—[—Ar$^d_{m6}$—Ar$^a_{m2}$—Ar$^e_{m7}$—Ar$^b_{m4}$—Ar$^c_{m5}$]—*  (IV)

wherein

Ar$^a$, Ar$^b$, Ar$^c$, m2, m4 and m5 are as defined above;

Ar$^d$ and Ar$^e$ are independently of each other aryl or heteroaryl with electron donor properties or electron acceptor properties, preferably independently of each other chosen from the group consisting of formulae (D1) to (D132) and (A1) to (A93); and m6 and m7 are independently of each other 0, 1 or 2, provided that at least one of m6 and m7 is not 0 (for example m6 is 0 and m7 is 1, or m6 is 1 and m7 is 0, or m6 is 1 and m7 is 1).

Preferred oligomers and polymers may for example comprise a polymer chain of formula (V)

*—[(M$^1$)$_{mx}$—(M$^2$)$_{my}$—(M$^3$)$_{mz}$]$_m$—*  (V)

wherein m is an integer >1;

M$^1$, M$^2$ and M$^3$ are independently of each other monomeric units as defined below, provided that at least one of M$^1$, M$^2$ and M$^3$ comprises a structural unit selected from the group consisting of formulae (I) and (Ia);

mx is >0 and ≤1;

my is ≥0 and <1; and mz is ≥0 and <1, with the provision that mx+my+mz=1, and preferably with the provision that for whichever of M$^1$, M$^2$ or M$^3$ comprises the structural unit M of formula (I) or (Ia) the respective mx, my or mz is >0. Thus, if M is comprised in M$^2$, the my>0, and if M is comprised in M$^3$, then mz>0.

Preferably M$^1$, M$^2$ and M$^3$ are independently of each other selected from the group consisting of M as defined in and for above formulae (III), (III-a-1), (III-a-2) and (III-b-1) to (III-b-5).

Examples of suitable polymer chains of formula (IV) may be selected from the following formulae (V-1) to (V-10)

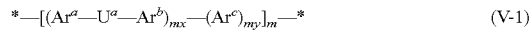 (V-1)

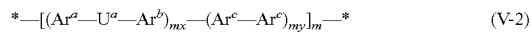 (V-2)

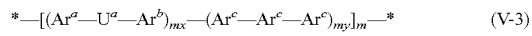 (V-3)

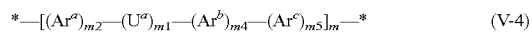 (V-4)

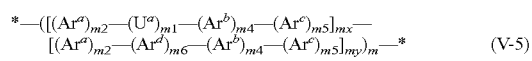 (V-5)

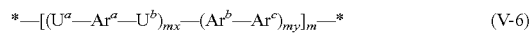 (V-6)

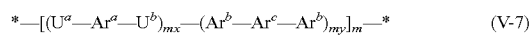 (V-7)

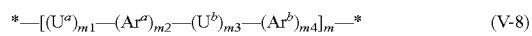 (V-8)

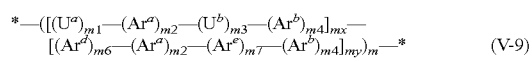 (V-9)

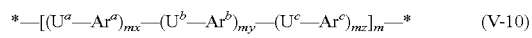 (V-10)

wherein Ar$^a$, Ar$^b$, Ar$^c$, Ar$^d$, Ar$^e$, U$^a$, U$^b$, m1, m2, m3, m4, m5, m6, m7, m, mx, my and mz are as defined above, and U$^c$ is as defined above for U$^a$ and U$^b$.

Such polymers can be alternating or random copolymers. With respect to formulae (V-4) and (V-6) it is preferred that in at least one of the repeating units [(Ar$^a$)$_{m2}$—(U$^a$)$_{m1}$—(Ar$^b$)$_{m4}$—(Ar$^c$)$_{m5}$], and—if present—in at least one of the repeating units [(Ar$^a$)$_{m2}$—(Ar$^d$)$_{m6}$—(Ar$^b$)$_{m4}$—(Ar$^c$)$_{m5}$] m1 is at least 1 and m4 is at least 1. With respect to formulae (V-8) and (V-9) it is preferred that in at least one of the repeating units [(U$^a$)$_{m1}$—(Ar$^a$)$_{m2}$—(U$^b$)$_{m3}$—(Ar$^b$)$_{m4}$], and—if present—in at least one of the repeating units [(Ar$^d$)$_{m6}$—(Ar$^a$)$_{m2}$—(Ar$^e$)$_{m7}$—(Ar$^b$)$_{m4}$] m1 is at least 1 and m6 is at least 1.

For the present oligomers and polymers the total number m of repeating units is preferably from 2 to 10000. For a polymer the total number m of repeating units is preferably at least 10 and most preferably at least 50. For a polymer the total number m of repeating units is preferably at most 2000, more preferably at most 1000 and most preferably at most 500. Any combination of these values is also possible.

The present oligomers and polymers include homopolymers and copolymers, such as for example statistical or random copolymers, alternating copolymers and block copolymers as well as any combination of these.

Particularly preferred are polymers selected from the following groups a) Group 1 consisting of homopolymers of the unit U$^a$ or (Ar$^a$—U$^a$) or (Ar$^a$—U$^a$—Ar$^b$) or (Ar$^a$—U$^a$—Ar$^c$) or (U$^a$—Ar$^b$—Ar$^c$) or (Ar$^a$—U$^a$—Ar$^b$—Ar$^c$) or (U$^a$—Ar$^a$—U$^a$), i.e. where all repeating units are identical, b) Group 2 consisting of random or alternating copolymers formed by identical units (Ar$^a$—U$^a$—Ar$^b$) or (U$^a$—Ar$^a$—U$^a$) and identical units (Ar$^c$), c) Group 3 consisting of random or alternating copolymers formed by identical units (Ar$^a$—U$^a$—Ar$^b$) or (U$^a$—Ar$^a$—U$^b$) and identical units (Ar$^a$), d) Group 4 consisting of random or alternating copolymers formed by identical units ($Ar^a$—$U^a$—$Ar^b$) or ($U^a$—$Ar^a$—$U^b$) and identical units ($Ar^a$—$Ar^d$—$Ar^b$) or ($Ar^d$—$Ar^a$—$Ar^e$), wherein in all these groups $Ar^a$, $Ar^b$, $Ar^c$, $Ar^d$, $Ar^e$, $U^a$ and $U^b$ are as defined above and below, in groups 1, 2 and 3 $Ar^a$, $Ar^b$ and $Ar^c$ are different from a single bond, and in group 4 one of $Ar^a$ and $Ar^b$ may also denote a single bond.

Preferred polymers of formulae (V) and (V-1) to (V-10) may be those of formula (VIII)

(VI)

wherein "chain" denotes a polymer chain of any one of formulae (IV) or (V-1) to (V-10), and $R^e$ and $R^f$ have independently of each other one of the meanings of $R^S$ as defined above, or denote, independently of each other, H, F, Br, Cl, I, —$CH_2Cl$, —CHO, —CR'=CR''$_2$, —SiR'R''R''', —SiR'X''X''', —SiR'R''X''', —SnR'R''R''', —BR'R'', —B(OR')(OR''), —B(OH)$_2$, —O—SO$_2$—R', —C≡CH, —C≡C—SiR'$_3$, —ZnX'' or an endcap group, X'' and X''' denote halogen, R', R'' and R''' have independently of each other one of the meanings of $R^0$ as defined earlier, and two of R', R'' and R''' may also form a ring together with the atom to which they are attached.

Preferred endcap groups $R^e$ and $R^f$ are selected from the group consisting of H, $C_{1-20}$ alkyl, optionally substituted $C_{6-12}$ aryl, and optionally substituted $C_{5-10}$ heteroaryl. Most preferred endcap groups are selected from the group consisting of H alkyl having from 1 to 10 carbon atoms, and phenyl.

In the polymer chains of formulae (IV) and (V-1) to (V-10) mx, my and mz denote the mole fraction of units $M^1$, $M^2$ and $M^3$, respectively, and m denotes the degree of polymerisation. These formulae are intended to include block copolymers, random or statistical copolymers and alternating copolymers of $M^1$, $M^2$ and $M^3$, as well as homopolymers of $M^1$ for the case when mx>0 and my=mz=0.

Further preferred are repeating units, monomers, oligomers and polymers of formulae (II-a), (II-b), (III), (III-a-1), (III-a-2), (III-b-1) to (III-b-5), (IV), (V), (V-1) to (V-10) and (VI) characterised by one or more of the following preferred or alternative aspects provided that such aspects are not mutually exclusive:

0<my<1 and mz=0;
0<my<1 and 0<mz<1;
$M_w$ is at least 5,000, preferably at least 8,000, more preferably at least 10,000;
$M_w$ is at most 300,000, preferably at most 100,000;
$R^1$ and $R^2$ are phenyl which is mono- or polysubstituted, preferably mono-substituted in the 4-position (i.e. the para-position), with substituents selected from linear or branched alkyl having from 1 to 20 carbon atoms, wherein one or more H may optionally be replaced by F;
all groups $R^s$ denote H;
at least one group $R^s$ is different from H;
$R^s$ may be selected independently at each occurrence from the group consisting of primary alkyl having from 1 to 30 carbon atoms, secondary alkyl having from 3 to 30 carbon atoms, and tertiary alkyl having from 4 to 30 carbon atoms, wherein one or more H may optionally be replaced by F;
$R^s$ may be selected independently at each occurrence from the group consisting of aryl and heteroaryl, each of which may optionally be fluorinated, alkylated or alkoxylated and has from 4 to 30 ring atoms;

$R^S$ is selected, on each occurrence identically or differently, from the group consisting of aryl and heteroaryl, each of which is optionally fluorinated, or alkylated and has 4 to 30 ring atoms,
$R^S$ is selected, on each occurrence identically or differently, from the group consisting of primary alkoxy or sulfanylalkyl with 1 to 30 C atoms, secondary alkoxy or sulfanylalkyl with 3 to 30 C atoms, and tertiary alkoxy or sulfanylalkyl with 4 to 30 C atoms, wherein in all these groups one or more H atoms are optionally replaced by F,
$R^S$ is selected, on each occurrence identically or differently, from the group consisting of aryloxy and heteroaryloxy, each of which is optionally alkylated or alkoxylated and has 4 to 30 ring atoms,
$R^S$ is selected, on each occurrence identically or differently, from the group consisting of alkylcarbonyl, alkoxycarbonyl and alkylcarbonyloxy, all of which are straight-chain or branched, are optionally fluorinated, and have from 1 to 30 C atoms,
$R^S$ denotes, on each occurrence identically or differently, F, Cl, Br, I, CN, $R^g$, —C(O)—$R^g$, —C(O)—O—$R^g$, or —O—C(O)—$R^g$, —SO$_2$—$R^g$, —SO$_3$—$R^g$, wherein $R^g$ is straight-chain, branched or cyclic alkyl with 1 to 30 C atoms, in which one or more non-adjacent C atoms are optionally replaced by —O—, —S—, —C(O)—, —C(O)—O—, —O—C(O)—, —O—C(O)—O—, —SO$_2$—, —SO$_3$—, —$CR^0$=$CR^{00}$— or —C≡C— and in which one or more H atoms are optionally replaced by F, Cl, Br, I or CN, or $R^g$ is aryl or heteroaryl having 4 to 30 ring atoms which is unsubstituted or which is substituted by one or more halogen atoms or by one or more groups $R^1$ as defined above,
$R^0$ and $R^{00}$ are selected from H or $C_1$-$C_{10}$-alkyl,
$R^e$ and $R^f$ are independently of each other selected from H, halogen, —$CH_2Cl$, —CHO, —CH=$CH_2$—SiR'R''R''', —SnR'R''R''', —BR'R'', —B(OR')(OR''), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, preferably phenyl,
$R^c$ and $R^d$ are independently of each other selected from the group consisting of Cl, Br, I, O-tosylate, O-triflate, O-mesylate, O-nonaflate, —SiMe$_2$F, —SiMeF$_2$, —O—SO$_2Z^1$, —B(O$Z^2$)$_2$, —C$Z^3$=C($Z^4$)$_2$, —C≡CH, C≡CSi($Z^1$)$_3$, —Zn$X^0$ and —Sn($Z^4$)$_3$, wherein $X^0$ is halogen, and $Z^1$, $Z^2$, $Z^3$ and $Z^4$ are selected from the group consisting of alkyl and aryl, each being optionally substituted, and two groups $Z^2$ may also form a cyclic group.

The compounds of the present invention can be synthesized according to or in analogy to methods that are known to the skilled person and are described in the literature. Other methods of preparation can be taken from the examples. For example, the polymers can be suitably prepared by aryl-aryl coupling reactions, such as Yamamoto coupling, Suzuki coupling, Stille coupling, Sonogashira coupling, Heck coupling or Buchwald coupling. Suzuki coupling, Stille coupling and Yamamoto coupling are especially preferred. The monomers which are polymerized to form the repeat units of the polymers can be prepared according to methods which are known to the person skilled in the art.

Thus, the process for preparing the present polymers comprises the step of coupling monomers, therein comprised a monomer comprising the structural unit of formula (I) or of formula (Ia), said monomers comprising at least one or alternatively two functional monovalent group selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is halogen, and Z$^1$, Z$^2$, Z$^3$ and Z$^4$ are independently of each other selected from the group consisting of alkyl and aryl, each being optionally substituted, and two groups Z$^2$ may also together form a cyclic group.

Preferably the polymers are prepared from monomers of general formula (II-b) or their preferred subformulae as described above and below.

Another aspect of the invention is a process for preparing a polymer by coupling one or more identical or different monomeric units comprising a structural unit of formula (I) or (Ia) or monomers of general formula (II-a) with each other and/or with one or more co-monomers in a polymerisation reaction, preferably in an aryl-aryl coupling reaction.

Suitable and preferred comonomers may be selected from the following formulae

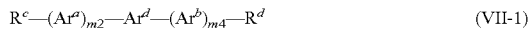  (VII-1)

  (VII-2)

  (VII-3)

wherein Ar$^a$, Ar$^b$, Ar$^d$, m2, m4, R$^c$ and R$^d$ are as defined herein. Very preferred is a process for preparing a polymer by coupling one or more monomers selected from formula (III-a-1) or (III-a-2) with one or more monomers of formula (VII-1), and optionally with one or more monomers selected from formula (VII-2) and (VII-3), in an aryl-aryl coupling reaction, wherein preferably R$^c$ and R$^d$ are selected from Cl, Br, I, —B(OZ$^2$)$_2$ and —Sn(Z$^4$)$_3$.

For example, preferred embodiments of the present invention relate to a) a process of preparing a polymer by coupling a monomer of formula (VII-1)

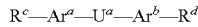

with a monomer of formula (VII-2)

  (VII-2)

in an aryl-aryl coupling reaction; or b) a process of preparing a polymer by coupling a monomer of formula

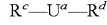

with a monomer of formula (VII-1)

  (VII-1)

in an aryl-aryl coupling reaction; or c) a process of preparing a polymer by coupling a monomer of formula

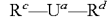

with a monomer of formula (VII-3)

  (VII-3)

in an aryl-aryl coupling reaction; or d) a process of preparing a polymer by coupling a monomer of formula

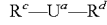

with a monomer of formula (VII-3)

  (VII-3)

and a monomer of formula (VII-2)

  (VII-2)

in an aryl-aryl coupling reaction; or e) a process of preparing a polymer by coupling a monomer of formula

with a monomer of formula (VII-2)

  (VII-2)

in an aryl-aryl coupling reaction; or f) a process of preparing a polymer by coupling a monomer of formula

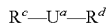

with a monomer of formula (VII-2)

  (VII-2)

and a monomer of formula (VII-3)

  (VII-3)

in an aryl-aryl coupling reaction,
wherein Ar$^a$, Ar$^b$, Ar$^d$, U$^a$, U$^b$, R$^c$ and R$^d$ are as defined herein, with R$^c$ and R$^d$ preferably selected from Cl, Br, I, —B(OZ$^2$)$_2$ and —Sn(Z$^4$)$_3$ as defined in respect to formulae (IV-a) and (II-b).

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in J. Chem. Soc., Chem. Commun., 1977, 683-684. Yamamoto coupling is described for example in T. Yamamoto et al., Prog. Polym. Sci., 1993, 17, 1153-1205, or WO 2004/022626 A1, and Stille coupling is described for example in Z. Bao et al., J. Am. Chem. Soc., 1995, 117, 12426-12435. For example, when using Yamamoto coupling, monomers having two reactive halide groups are preferably used. When using Suzuki coupling, compounds of formula (II-b) having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand, for example Pd(Ph$_3$P)$_4$. Another preferred phosphine ligand is tris(ortho-tolyl)phosphine, for example Pd(o-Tol$_3$P)$_4$. Preferred Pd(II) salts include palladium acetate, for example Pd(OAc)$_2$. Alternatively the Pd(0) complex can be prepared by mixing a Pd(0) dibenzylideneacetone complex, for example tris(dibenzyl-ideneacetone) dipalladium(0), bis(dibenzylideneacetone)-palladium(0), or Pd(II) salts e.g. palladium acetate, with a phosphine ligand, for example triphenylphosphine, tris(ortho-tolyl)phosphine or tri(tert-butyl)phosphine. Suzuki polymerisation is performed in the presence of a base, for example sodium carbonate, potassium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl)nickel(0).

Suzuki and Stille polymerisation may be used to prepare homopolymers as well as statistical, alternating and block random copolymers. Statistical or block copolymers can be prepared for example from the above monomers of formula (IV) or its subformulae, wherein one of the reactive groups is halogen and the other reactive group is a boronic acid, boronic acid derivative group or and alkylstannane. The synthesis of statistical, alternating and block copolymers is described in detail for example in WO 03/048225 A2 or WO 2005/014688 A2.

As alternatives to halogens as described above, leaving groups of formula —O—SO$_2$Z$^1$ can be used wherein Z$^1$ is as described above. Particular examples of such leaving groups are tosylate, mesylate and triflate.

Exemplary syntheses of a homopolymer comprising a divalent unit of formula (I) are shown in Scheme 3, using either a small molecule of formula (II-a) or a monomer of formula (II-b) as starting material.

addition also be as defined for $Z^{1-4}$ elsewhere in this application; and R$^c$ and R$^d$ may in addition also be as defined elsewhere in this application.

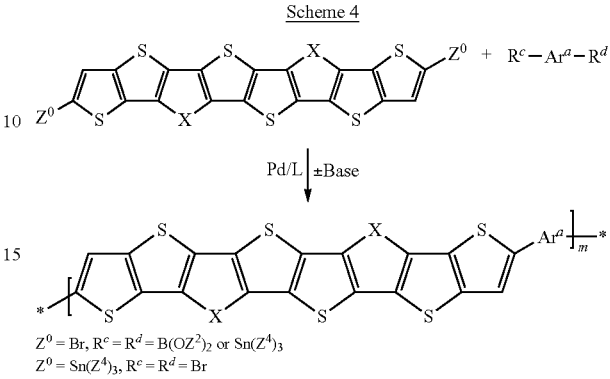

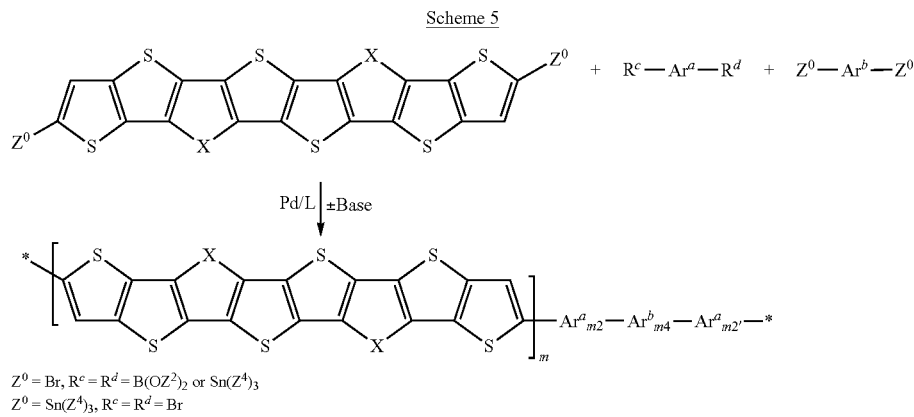

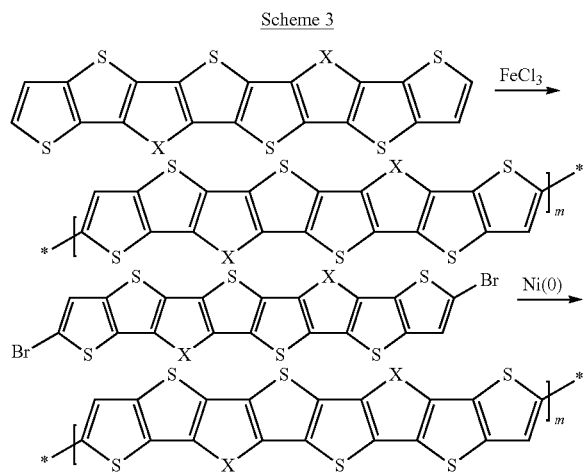

An exemplary synthesis of copolymers comprising a divalent unit of formula (I) is schematically illustrated in Schemes 4 and 5, wherein in Scheme 4 an alternating copolymer is produced and in Scheme 5 a statistical (or random) block copolymer is produced, and wherein X, m, Ar$^a$, Ar$^b$, m2 and m4 are as defined elsewhere in this application; m2' may be as defined for m2; Z$^0$ may in Blends, Formulations and Devices The compounds and polymers according to the present invention can also be used in mixtures or polymer blends, for example together with small molecules or monomeric compounds or together with other polymers having charge-transport, semiconducting, electrically conducting, photo-conducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more small molecules, polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, tetraline, decaline, indane, methyl benzoate, ethyl benzoate, mesitylene and/or mixtures thereof.

The concentration of the compounds or polymers in the solution is preferably 0.1 to 10% by weight, more preferably 0.5 to 5% by weight, with % by weight given relative to the total weight of the solution. Optionally, the solution also comprises one or more binders to adjust the rheological properties, as described for example in WO 2005/055248 A1.

After appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in J. D. Crowley et al., *Journal of Paint Technology*, 1966, 38 (496), 296. Solvent blends may also be used and can be identified as described in Solvents, W. H. Ellis, Federation of Societies for Coatings Technology, p. 9-10, 1986. Such a procedure may lead to a blend of 'non'-solvents that will dissolve both the polymers of the present invention, although it is desirable to have at least one true solvent in a blend.

The compounds and polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices need to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a compound or polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymer blends and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds and polymers to the present invention are useful as charge transport, semiconducting, electrically conducting, thermoelectric, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting compound, polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a compound, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a compound, polymer, polymer blend, formulation or organic semiconducting layer according to the present invention. Preferred devices are OFETs, TFTs, ICs, logic circuits, capacitors, RFID tags, OLEDs, OLETs, OPEDs, OPVs, OPDs, solar cells, laser diodes, photoconductors, photodetectors, thermoelectric sensors, electrophotographic devices, electrophotographic recording devices, organic memory devices, sensor devices, charge injection layers, Schottky diodes, planarising layers, antistatic films, conducting substrates and conducting patterns. Particularly preferred devices are OLEDs.

Especially preferred electronic devices are OFETs, OLEDs, OPV and OPD devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide ($ZnO_x$), zinc tin oxide (ZTO), titan oxide ($TiO_x$), molybdenum oxide ($MoO_x$), nickel oxide ($NiO_x$), or cadmium selenide (CdSe), or an organic material such as graphene or a fullerene or a substituted fullerene, for example an indene-$C_{60}$-fullerene bisaduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. Chem. Mater. 2004, 16, 4533).

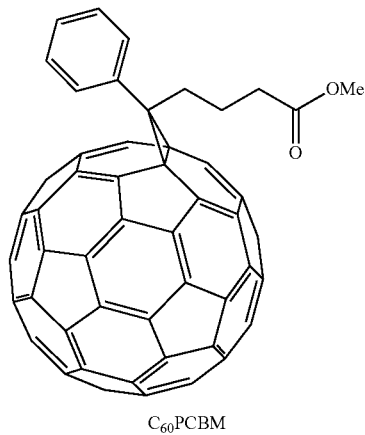 [SMILES: COC(=O)CCCC1(c2ccccc2)C23C=C4Cc5cc6cc7c8c9c(cc%10cc%11c%12c(c%13c%14c%15c(c4c5c4c6c8c(c%154)c4c9c%10c%12c%144)C%1321)C(=C3)C%11)C7]

$C_{60}$PCBM

Preferably the polymer according to the present invention is blended with an n-type semiconductor such as a fullerene or substituted fullerene, like for example PCBM-$C_{60}$, PCBM-$C_{70}$, PCBM-$C_{61}$, PCBM-$C_{71}$, bis-PCBM-$C_{61}$, bis-PCBM-$C_{71}$, ICMA-$c_{60}$ (1',4'-Dihydro-naphtho[2',3'1,2][5,6]fullerene-$C_{60}$), ICBA-$C_{60}$, oQDM-$C_{60}$ (1',4'-dihydro-naphtho[2',3'1,9][5,6]fullerene-C60-Ih), bis-oQDM-$C_{60}$, graphene, or a metal oxide, like for example, $ZnO_x$, $TiO_x$, ZTO, $MoO_x$, $NiO_x$, or quantum dots like for example CdSe or CdS, to form the active layer in an OPV or OPD device. The device preferably further comprises a first transparent or semi-transparent electrode on a transparent or semi-transparent substrate on one side of the active layer, and a second metallic or semi-transparent electrode on the other side of the active layer.

Further preferably the OPV or OPD device comprises, between the active layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly[9,9-bis(2-ethylhexyl)-fluorene]-b-poly[3-(6-trimethylammoniumhexyl)thiophene], or poly[(9,9-bis(3'-(N,N-dimethyl-amino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a blend or mixture of a polymer according to the present invention with a fullerene or modified fullerene, the ratio polymer:fullerene is preferably from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the compounds, polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a $C_{60}$ or $C_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulf oxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
optionally a substrate,
a high work function electrode, preferably comprising a metal oxide, like for example ITO, serving as anode,
an optional conducting polymer layer or hole transport layer, preferably comprising an organic poymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
optionally a layer having electron transport properties, for example comprising LiF,
a low work function electrode, preferably comprising a metal like for example aluminum, serving as cathode,
wherein at least one of the electrodes, preferably the anode, is transparent to visible light, and
wherein the p-type semiconductor is a polymer according to the present invention.

A second preferred OPV device according to the invention is an inverted OPV device and comprises the following layers (in the sequence from bottom to top):
optionally a substrate,
a high work function metal or metal oxide electrode, comprising for example ITO, serving as cathode,
a layer having hole blocking properties, preferably comprising a metal oxide like $TiO_x$ or $Zn_x$,
an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic poymer or polymer blend, for example of PEDOT:PSS or TBD or NBD,
an electrode comprising a high work function metal like for example silver, serving as anode,
wherein at least one of the electrodes, preferably the cathode, is transparent to visible light, and
wherein the p-type semiconductor is a polymer according to the present invention.

In the OPV devices of the present invention the p-type and n-type semiconductor materials are preferably selected from the materials, like the polymer/fullerene systems, as described above When the active layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater*, 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

The compounds, polymers, formulations and layers of the present invention are also suitable for use in an OFET as the semiconducting channel.

Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound, polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers, and
optionally a substrate,
wherein the semiconductor layer preferably comprises a compound, polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913 A1.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Materials comprising a divalent unit in accordance with the present application have been found to give good charge-carrier mobilities. Without wishing to be bound by theory it is believed that the good performance is at least partly due to the fact that the increased rigidity of the divalent unit of the present application, which when used in polymers also leads to an increased rigidity of the polymer backbone. Particularly, though not exclusively, for polymer it is thought that this structural rigidity leads to reduced reorganization energy and in consequence gives a high charge-carrier mobility. Additionally the structural rigidity will allow an ordered packing for example of a polymer comprising a divalent unit in accordance with the present application.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius. The values of the dielectric constant ∈ ("permittivity") refer to values taken at 20° C. and 1,000 Hz.

EXAMPLES

The following examples are to illustrate the advantages of the present invention in more detail in a non-limitative way.

Example 1 a) Synthesis of 5,5"-Bis-triisopropylsilanyl-[2,2';5',2"]ter[thieno[3,2-b]thio-phene]-3',6'-dicarboxylic acid diethyl ester (3)

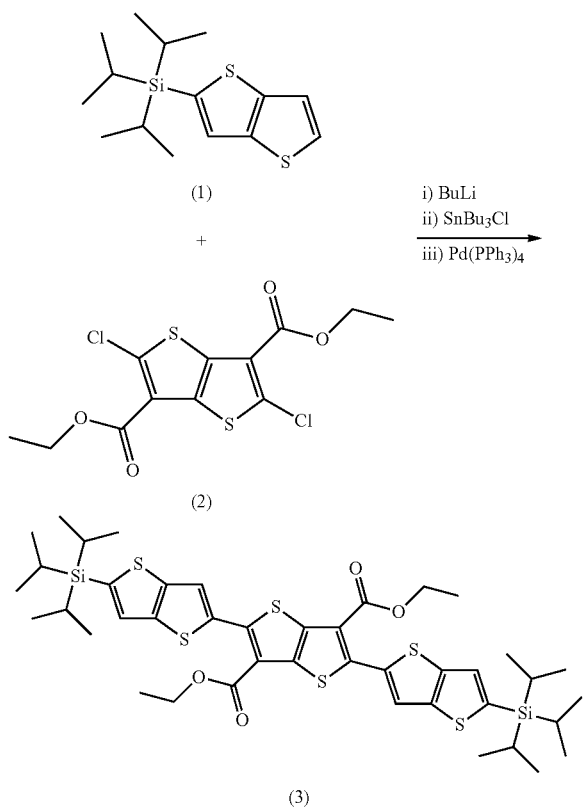

To a solution of triisopropyl-thieno[3,2-b]thiophen-2-yl-silane 1 (2.4 g, 8.0 mmol) in anhydrous tetrahydrofuran (60 cm$^3$) at −78° C. was added dropwise n-butyllithium (4.2 cm$^3$, 10 mmol, 2.5 M in hexane) over 20 minutes. The mixture was stirred at −78° C. for 1 hour and at −30° C. for 1.5 hours before cooling back to −78° C. Tributyltin chloride (3.2 cm$^3$, 11 mmol) was added all at once and the reaction mixture allowed to warm to 23° C. over 17 hours. The solvent was removed in vacuo and the residue taken up in anhydrous toluene (50 cm$^3$). 2,5-Dichloro-thieno[3,2-b]thiophene-3,6-dicarboxylic acid diethyl ester 2 (1.13 g, 3.2 mmol) and tetrakis(triphenyl-phosphine)palladium(0) (0.5 g, 0.4 mmol) were added and the reaction mixture stirred at 70° C. for 65 hours. The solvent was removed in vacuo and the residue triturated in methanol (250 cm$^3$). The solid was collected by filtration and washed with methanol (2×200 cm$^3$) and water (200 cm$^3$). The solid was further purified by silica plug (dichloromethane) and the residue triturated in acetone (200 cm$^3$). The solid was then collected by filtration to give 5,5"-bis-triisopropylsilanyl-[2,2';5',2"]ter[thieno[3,2-b]thiophene]-3',6'-dicarboxylic acid diethyl ester 3 (2.20 g, 78%) as a yellow solid.
$^1$H-NMR (300 MHz, CDCl$_3$) 1.11-1.18 (36H, m), 1.31-1.48 (12H, m), 4.43 (4H, q, J 7.2), 7.37 (2H, s), 7.82 (2H, s).

b) {6'-[Bis-(4-dodecyl-phenyl)-hydroxy-methyl]-5,5"-bis-triisopropylsilanyl-[2,2';5',2"]ter[thieno[3,2-b]thiophene]-3'-yl}-bis-(4-dodecyl-phenyl)-methanol (4)

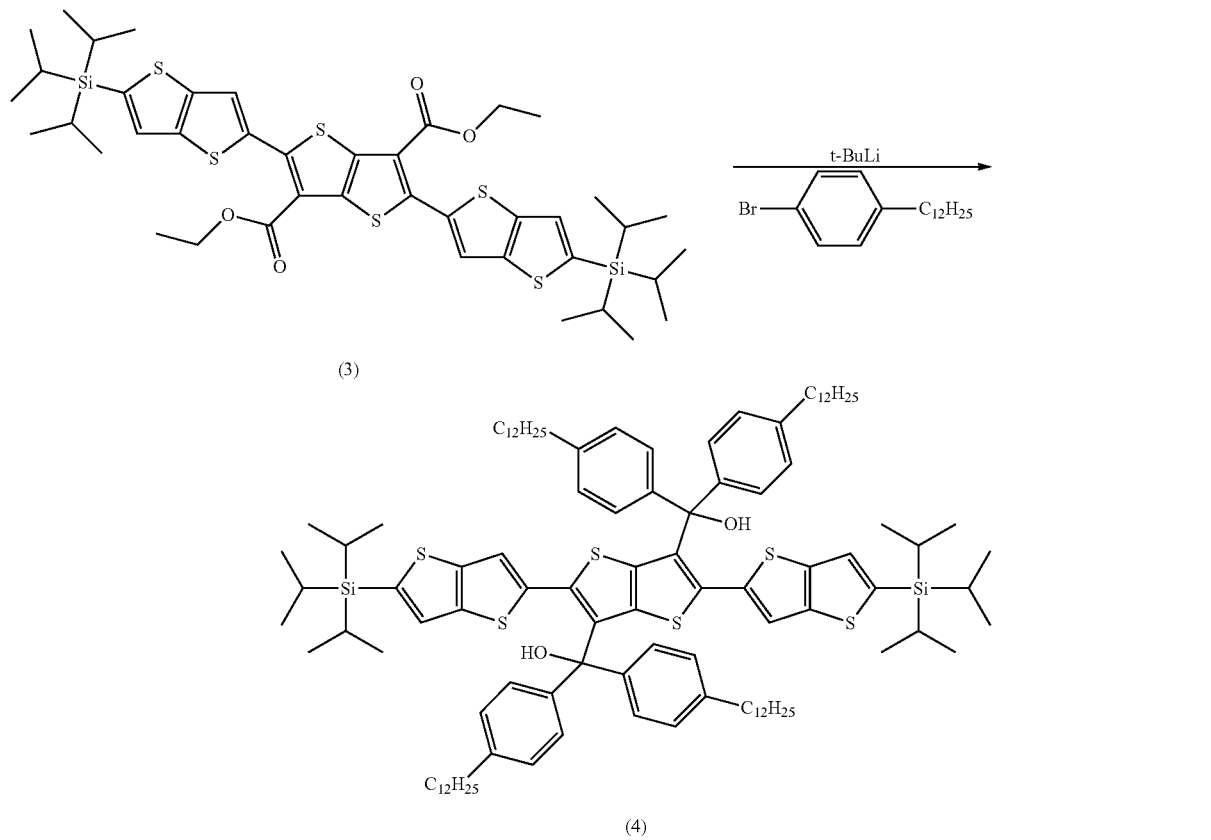

To a suspension of 1-bromo-4-dodecylbenzene (2.2 g, 6.8 mmol) in anhydrous tetrahydrofuran (50 cm$^3$) at −78° C. was added dropwise tert-butyllithium (7.2 cm$^3$, 14 mmol, 1.9 M in pentane) over 30 minutes. After addition, the reaction mixture was stirred at −78° C. for 1 hour. 5,5"-Bis-triisopropylsilanyl-[2,2';5',2"]ter[thieno[3,2-b]thiophene]-3',6'-dicarboxylic acid diethyl ester 3 (1.0 g, 1.1 mmol) was then added in one portion. The reaction mixture was then stirred at −78° C. for 2 hours and at 23° C. for 17 hours. The reaction mixture was poured into water (150 cm$^3$) and the organics extracted with diethyl ether (5×50 cm$^3$). The combined organics were washed with brine (100 cm$^3$), dried over anhydrous magnesium sulphate, filtered and the solvent removed in vacuo. The crude was purified by column chromatography (n-pentane) to give {6'[bis-(4-dodecyl-phenyl)-hydroxy-methyl]-5,5"-bis-triisopropylsilanyl-[2,2';5',2"]ter[thieno[3,2-b]thiophene]-3'-yl}-bis-(4-dodecyl-phenyl)-methanol 4 (800 mg, 40%) as a colourless oil.
$^1$H-NMR (300 MHz, CDCl$_3$) 0.84-0.92 (12H, m), 1.06-1.17 (36H, m), 1.21-1.37 (78H, m), 1.54-1.66 (8H, m), 2.53-2.63 (8H, m), 3.45 (2H, s), 6.50 (2H, s), 7.08 (8H, d, J 8.3), 7.17 (2H, s), 7.20 (8H, d, J 8.3).

C)

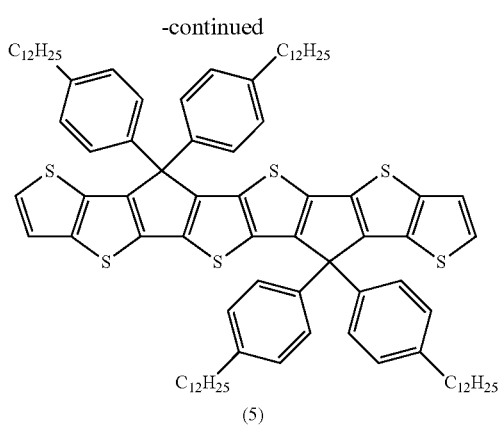

To a solution of {6'[bis-(4-dodecyl-phenyl)-hydroxymethyl]-5,5"-bis-triisopropylsilanyl-[2,2';5',2"]ter[thieno[3,2-b]thiophene]-3'-yl}-bis-(4-dodecyl-phenyl)-methanol 4

(800 mg, 0.45 mmol) in toluene (50 cm³) that had been degassed by bubbling nitrogen was added amberlyst 15 (4.0 g). The resulting suspension was degassed for a further 1 hour and then stirred at 60° C. for 4 hours. The reaction mixture was allowed to cool to 23° C. and filtered. The solid was washed with dichloromethane (2×100 cm³) and the solvent removed in vacuo. The crude was purified by column chromatography (40-60 petrol) to give compound 5 (500 mg, 78%) as a yellow solid.

¹H-NMR (300 MHz, CD₂Cl₂) 0.74-0.83 (12H, m), 1.11-1.28 (72H, m), 1.42-1.53 (8H, m), 2.42-2.51 (8H, m), 7.00-7.10 (16H, m), 7.19-7.25 (4H, m).

d)

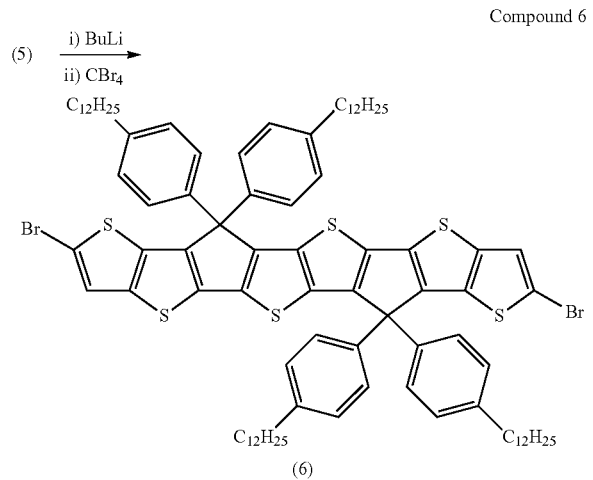

Compound 6

To a solution of compound 5 (500 mg, 0.35 mmol) in anhydrous tetrahydrofuran (30 cm³) at −78° C. was added dropwise n-butyllithium (0.54 cm³, 1.4 mmol, 2.5 M in hexane) over 20 minutes. The reaction mixture was stirred at −78° C. for 1 hour. Carbon tetrabromide (580 mg, 1.8 mmol) was added and the reaction mixture allowed to warm to 23° C. over 17 hours. The reaction mixture was poured into water (100 cm³) and the organics extracted with 40-60 petrol (5×20 cm³). The combined organic layers were dried over anhydrous magnesium sulphate, filtered and the solvent removed in vacuo. The crude was purified by column chromatography (40-60 petrol) to give an oil which was triturated in acetone (100 cm³). The solid was collected by filtration to give compound 6 (200 mg, 35%) as a yellow solid.

¹H-NMR (300 MHz, CD₂Cl₂) 0.74-0.85 (12H, m), 1.19-1.29 (72H, m), 1.41-1.54 (8H, m), 2.42-2.51 (8H, m), 6.98-7.07 (16H, m), 7.23 (2H, br s).

Example 2 a) {6'-[Bis-(4-hexadecyl-phenyl)-hydroxy-methyl]-5,5"-bis-triisopropylsilanyl-[2,2';5',2"]ter[thieno[3,2-b]thiophene]-3'-yl}-bis-(4-hexadecyl-phenyl)-methanol (7)

To a suspension of 1-bromo-4-hexadecylbenzene (10.9 g, 28.5 mmol) in anhydrous tetrahydrofuran (1000 cm³) at −78° C. was added dropwise t-butyllithium (33.5 cm³, 57.0 mmol, 1.7 M in heptane) over 1 hour. After addition, the reaction mixture was stirred at −78° C. for 1 hour and then at −45° C. for 1 hour. After cooling to −78° C. 5,5"-bis-triisopropylsilanyl-[2,2';5',2"]ter[thieno[3,2-b]thiophene]-3',6'-dicarboxylic acid diethyl ester 3 (5.00 g, 5.7 mmol) was then added in one portion. The reaction mixture was then stirred at −78° C. for 2 hours and at 23° C. for 17 hours. The reaction mixture was poured into water (500 cm³) and the organics extracted with diethyl ether (2×500 cm³). The combined organics were washed with brine (200 cm³), dried over anhydrous magnesium sulphate, filtered and the solvent removed in vacuo. The crude was triturated in methanol (250 cm³) to give {6'-[bis-(4-hexadecyl-phenyl)-hydroxy-methyl]-5,5"-bis-triisopropylsilanyl-[2,2';5',2"]ter[thieno[3,2-b]thiophene]-3'-yl}-bis-(4-hexadecyl-phenyl)-methanol 7 (3.98 g, 35%) as a brown solid.

b)

To a solution of {6'-[bis-(4-hexadecyl-phenyl)-hydroxy-methyl]-5,5"-bis-triisopropylsilanyl-[2,2';5',2"]ter[thieno[3,2-b]thiophene]-3'-yl}-bis-(4-hexadecyl-phenyl)-methanol 7 (2.0 g, 1.0 mmol) in toluene (400 cm³) that had been degassed by bubbling nitrogen was added Amberlyst 15 (29.5 g). The resulting suspension was degassed for a further 1 hour and then stirred at 60° C. for 4 hours. The reaction mixture was allowed to cool to 23° C. and filtered. The solid was washed with dichloromethane (500 cm³) and the solvent removed in vacuo. The crude was purified by column chromatography (hot 80-100 petrol) to give compound 8 (1.50 g, 91%) as a yellow solid.

¹H-NMR (300 MHz, CDCl₃) 0.80-0.98 (12H, m), 1.15-1.39 (104H, m), 1.48-1.65 (8H, m), 2.48-2.61 (8H, m), 7.06-7.19 (16H, m), 7.23 (2H, d, J 5.2), 7.26 (2H, d, J 5.2).

c)

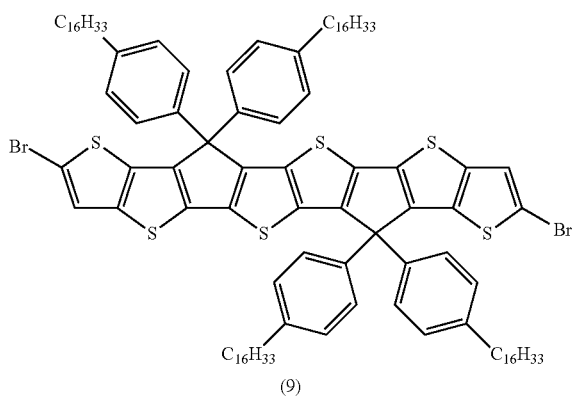

To a solution of compound 8 (1.5 g, 0.91 mmol) in tetrahydrofuran (150 cm³) was added N-bromosuccinimide (325 mg, 1.83 mmol) and the mixture was stirred for 3 hours. The reaction mixture was concentrated in vacuo and methanol (50 cm³) added. The solid was collected by filtration and washed with methanol (50 cm³) and the crude material purified by column chromatography (hot cyclohexane) to give compound 9 (1.29 g, 78%) as a yellow solid.

¹H-NMR (300 MHz, CD₂Cl₂) 0.85-0.99 (12H, m), 1.20-1.39 (104H, m), 1.49-1.64 (8H, m), 2.53-2.69 (8H, m), 7.08-7.20 (18H, m).

Example 3 a) {6'-[Bis-(4-octadecyl-phenyl)-hydroxy-methyl]-5,5''-bis-triisopropylsilanyl-[2,2';5',2'']ter[thieno[3,2-b]thiophene]-3'-yl}-bis-(4-octadecyl-phenyl)-methanol (10)

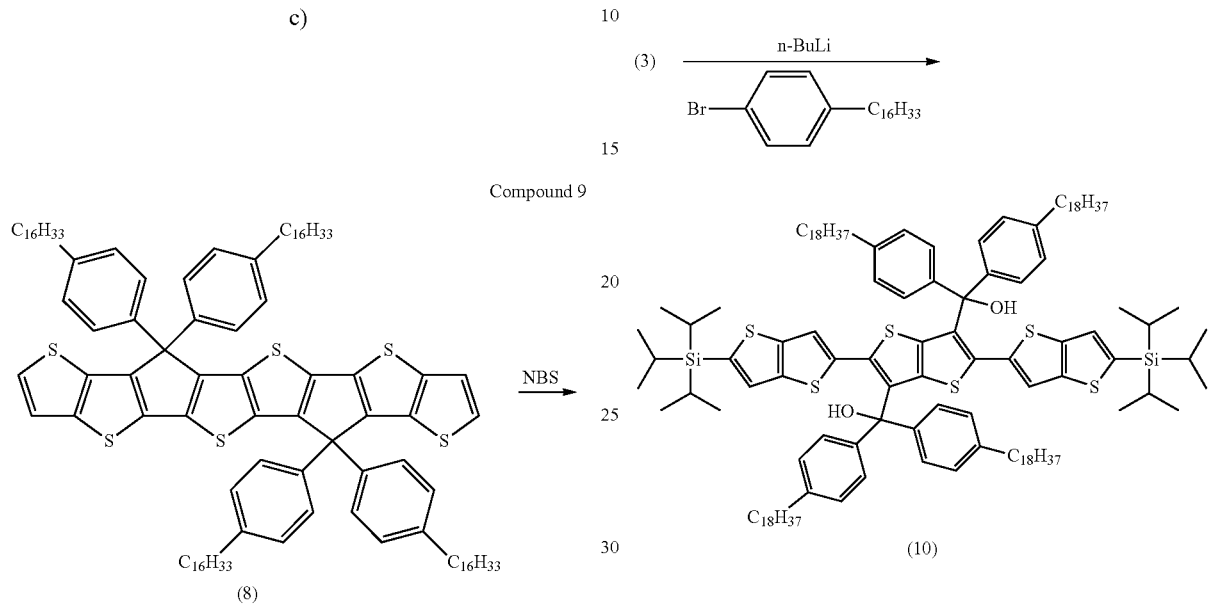

To a suspension of 1-bromo-4-octadecylbenzene (14.7 g, 35.2 mmol) in anhydrous tetrahydrofuran (400 cm³) at −78° C. was added dropwise n-butyllithium (14.1 cm³, 35.4 mmol, 2.5 M in pentane) over 30 minutes. After addition, the reaction mixture was stirred at −78° C. for 1 hour. 5,5''-Bis-triisopropylsilanyl-[2,2';5',2'']ter[thieno[3,2-b]thiophene]-3',6'-dicarboxylic acid diethyl ester 3 (4.95 g, 5.6 mmol) was then added in one portion. The reaction mixture was then stirred at −78° C. for 2 hours and at 23° C. for 65 hours. The reaction mixture was poured into water (500 cm³) and the organics extracted with diethyl ether (2×500 cm³). The combined organics were washed with brine (200 cm³), dried over anhydrous magnesium sulphate, filtered and the solvent removed in vacuo. The crude was purified by column chromatography (40-60 petrol:dichloromethane; 4:1) to give {6'-[bis-(4-octadecyl-phenyl)-hydroxy-methyl]-5,5''-bis-tri-isopropylsilanyl-[2,2';5',2'']ter[thieno[3,2-b]thiophene]-3'-yl}-bis-(4-octadecyl-phenyl)-methanol 10 (7.41 g, 62%) as a yellow oil.

¹H-NMR (300 MHz, CDCl₃) 0.78-0.94 (12H, m), 1.00-1.39 (162H, m), 1.51-1.66 (8H, m), 2.52-2.64 (8H, m), 3.44 (2H, s), 6.50 (2H, s), 7.05-7.12 (8H, m), 7.15-7.22 (10H, m).

b)

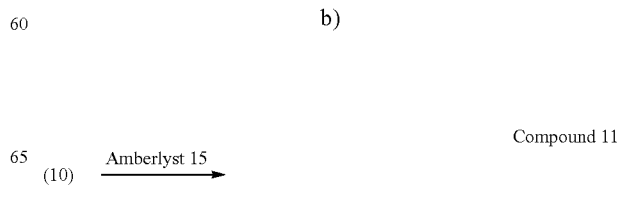

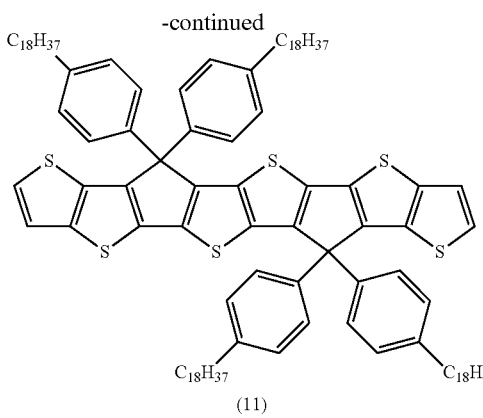

(11)

To a solution of {6'[bis-(4-octadecyl-phenyl)-hydroxymethyl]-5,5"-bis-triisopropylsilanyl-[2,2';5',2"]ter[thieno[3,2-b]thiophene]-3'-yl}-bis-(4-octadecyl-phenyl)-methanol 10 (6.80 g, 3.23 mmol) in toluene (400 cm³) that had been degassed by bubbling nitrogen was added amberlyst 15 (29.5 g). The resulting suspension was degassed for a further 1 hour and then stirred at 60° C. for 4 hours.

The reaction mixture was allowed to cool to 23° C. and filtered. The solid was washed with dichloromethane (500 cm³) and the solvent removed in vacuo. The crude was purified by column chromatography (hot 80-100 petrol) to give compound 11 (3.80 g, 67%) as a yellow solid.

$^1$H-NMR (300 MHz, CD$_2$Cl$_2$) 0.88-0.95 (12H, m), 1.24-1.39 (120H, m), 1.55-1.64 (8H, m), 2.54-2.63 (8H, m), 7.12-7.21 (16H, m), 7.30 (2H, d, J 5.2), 7.34 (2H, d, J 5.2).

c)

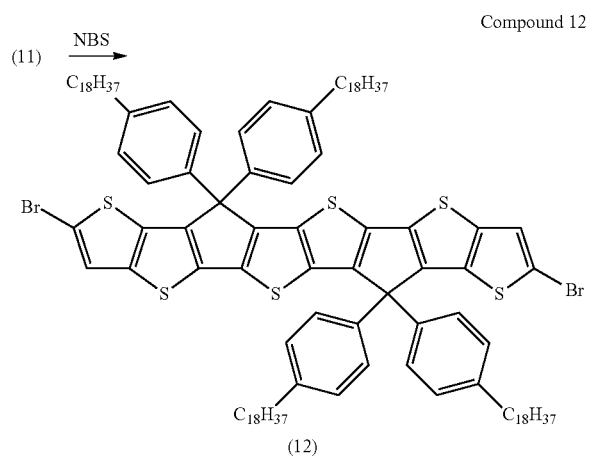

(12)

To a solution of compound 11 (300 mg, 0.17 mmol) in chloroform (15 cm³) at 40° C. was added dropwise acetic acid (2.5 cm³) and the mixture was stirred for 10 minutes. N-bromosuccinimide (95 mg, 0.53 mmol) was then added and the mixture stirred at 40° C. for 1 hour. The reaction mixture was concentrated in vacuo, and methanol (50 cm³) was added. The solid was collected by filtration and washed with methanol (50 cm³). The crude was purified by column chromatography (hot cyclohexane) to give compound 12 (280 mg, 86%) as a yellow solid.

$^1$H-NMR (300 MHz, CD$_2$Cl$_2$) 0.84-0.91 (12H, m), 1.20-1.35 (120H, m), 1.53-1.62 (8H, m), 2.49-2.59 (8H, m), 7.09-7.11 (16H, m), 7.26 (2H, s).

Example 4

Polymer 1

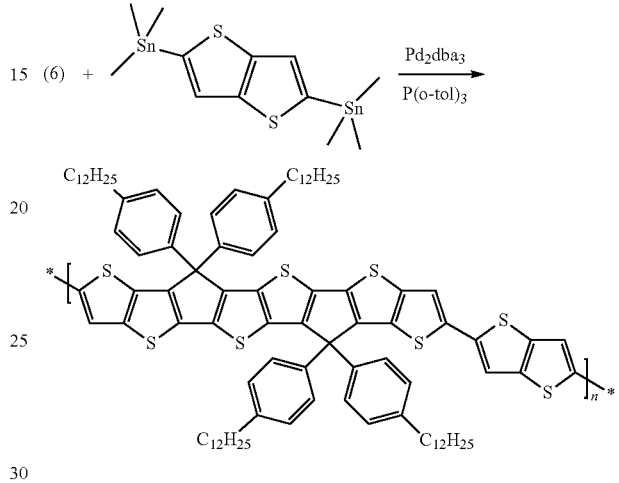

Nitrogen gas was bubbled through a mixture of compound 6 (200 mg, 0.127 mmol), 2,5-bis-trimethylstannanyl-thieno[3,2-b]thiophene (59.1 mg, 0.127 mmol), tris(dibenzylideneacetone)dipalladium(0) (1.8 mg, 0.003 mmol), tri-o-tolylphosphine (3.1 mg, 0.010 mmol) and anhydrous toluene (6 cm³) for one hour. The reaction mixture was then heated in a pre-heated oil bath at 100° C. for 2 hours. Bromobenzene (0.03 cm³) was added and the mixture heated at 100° C. for 10 minutes. Tributyl-phenyl-stannane (0.12 cm³) was then added and the mixture heated at 100° C. for 20 minutes. The mixture was allowed to cool slightly and poured into stirred methanol (100 cm³) and the polymer precipitate collected by filtration. The crude polymer was subjected to sequential Soxhlet extraction; acetone, 40-60 petrol, 80-100 petrol, cyclohexane and chloroform. The chloroform extract was poured into methanol (400 cm³) and the polymer precipitate collected by filtration to give polymer 1 (180 mg, 91%) as a red solid.

GPC (chlorobenzene, 50° C.) $M_n$=28,000 g/mol, $M_w$=62,000 g/mol.

Example 5

Polymer 2

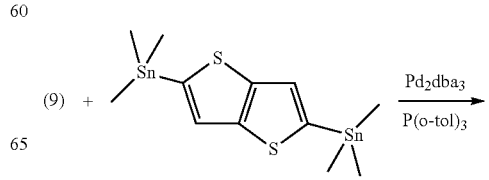

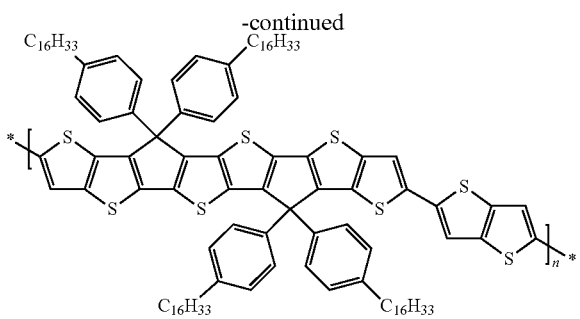

Nitrogen gas was bubbled through a mixture of compound 9 (250 mg, 0.139 mmol), 2,5-bis-trimethylstannanyl-thieno[3,2-b]thiophene (64.7 mg, 0.139 mmol), tris(dibenzylideneacetone)dipalladium(0) (4.9 mg, 0.007 mmol), tri-o-tolylphosphine (8.5 mg, 0.03 mmol), anhydrous toluene (5 cm$^3$) and anhydrous N,N-dimethylformamide for 25 minutes. The reaction mixture was then heated in a pre-heated oil bath at 100° C. for 25 minutes. Bromobenzene (0.003 cm$^3$) was added and the mixture heated at 100° C. for another 15 minutes. Tributyl-phenyl-stannane (0.01 cm$^3$) was then added and the mixture heated at 100° C. for 17 hours. The mixture was allowed to cool slightly and poured into stirred methanol (200 cm$^3$) and the polymer precipitate collected by filtration. The crude polymer was subjected to sequential Soxhlet extraction; acetone, methanol, 40-60 petrol, 80-100 petrol, cyclohexane and chloroform. The chloroform extract was poured into methanol (400 cm$^3$) and the polymer precipitate collected by filtration to give polymer 2 (230 mg, 86%) as a red solid.

GPC (chlorobenzene, 50° C.) $M_n$=59,000 g/mol, $M_w$=128,000 g/mol.

Example 6

Polymer 3

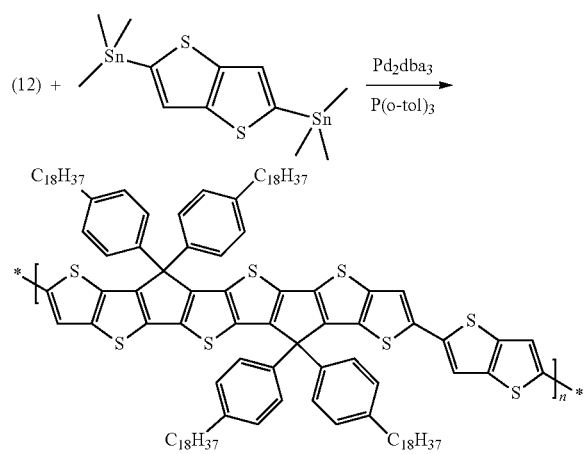

Nitrogen gas was bubbled through a mixture of compound 12 (200 mg, 0.105 mmol), 2,5-bis-trimethylstannanyl-thieno[3,2-b]thiophene (48.7 mg, 0.105 mmol), tris(dibenzylideneacetone)dipalladium(0) (1.5 mg, 0.002 mmol), tri-o-tolylphosphine (2.6 mg, 0.009 mmol) and anhydrous toluene (5 cm$^3$) for 25 minutes. The reaction mixture was then heated in a pre-heated oil bath at 110° C. for 90 minutes. Bromobenzene (0.02 cm$^3$) was added and the mixture heated at 110° C. for 20 minutes. Tributyl-phenyl-stannane (0.10 cm$^3$) was then added and the mixture heated at 110° C. for 25 minutes. The mixture was allowed to cool slightly and poured into stirred methanol (200 cm$^3$) and the polymer precipitate collected by filtration. The crude polymer was subjected to sequential Soxhlet extraction; acetone, 80-100 petrol, cyclohexane and chloroform. The chloroform extract was concentrated in vacuo and poured into methanol (350 cm$^3$) and the polymer precipitate collected by filtration to give polymer 3 (177 mg, 90%) as a red solid.

GPC (chlorobenzene, 50° C.) $M_n$=146,000 g/mol, $M_w$=640,000 g/mol.

GPC (1,2,4-trichlorobenzene, 140° C.) $M_n$=166,000 g/mol, $M_w$=520,000 g/mol.

Example 7

Polymer 4

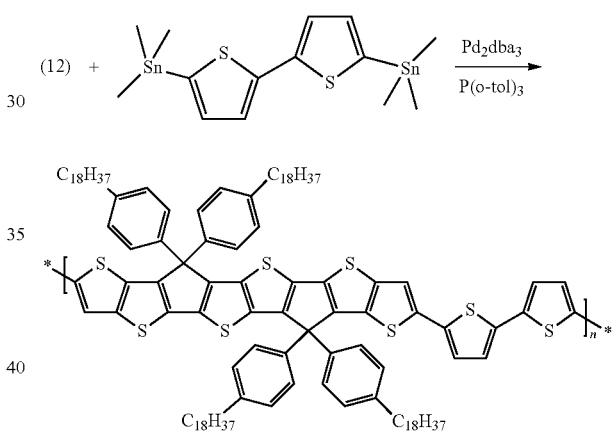

Nitrogen gas was bubbled through a mixture of compound 12 (200 mg, 0.105 mmol), 5,5'-bis(trimethylstannyl)-2,2'-bithiophene (51.4 mg, 0.105 mmol), tris(dibenzylideneacetone)dipalladium(0) (1.5 mg, 0.002 mmol), tri-o-tolylphosphine (2.6 mg, 0.009 mmol) and anhydrous toluene (5 cm$^3$) for 35 minutes. The reaction mixture was then heated in a pre-heated oil bath at 110° C. for 75 minutes. Bromobenzene (0.02 cm$^3$) was added and the mixture heated at 110° C. for 15 minutes. Tributyl-phenyl-stannane (0.10 cm$^3$) was then added and the mixture heated at 110° C. for 15 minutes. The mixture was allowed to cool slightly, poured into stirred methanol (200 cm$^3$) and the polymer precipitate collected by filtration. The crude polymer was subjected to sequential Soxhlet extraction; acetone, 40-60 petrol, 80-100 petrol, cyclohexane and chloroform. The chloroform extract was concentrated in vacuo and poured into methanol (300 cm$^3$) and the polymer precipitate collected by filtration to give polymer 4 (159 mg, 79%) as a red solid.

GPC (chlorobenzene, 50° C.) $M_n$=106,000 g/mol, $M_w$=258,000 g/mol.

Example 8

Polymer 5

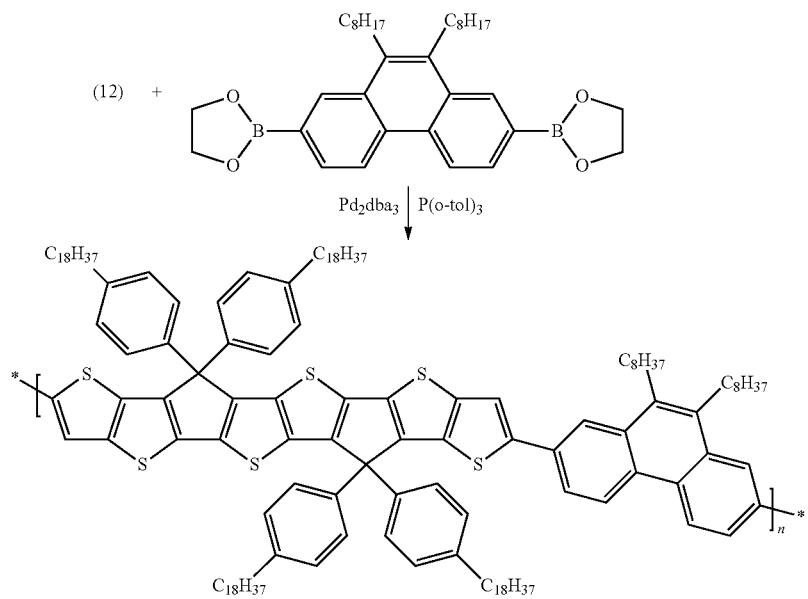

Nitrogen gas was bubbled through a mixture of compound 12 (291.7 mg, 0.153 mmol), 9,10-dioctyl-2,7-phenanthrylene-bis(1,3,2-dioxaborolane) (82.7 mg, 0.153 mmol), tri-o-tolyl-phosphine (3.7 mg, 0.012 mmol) and anhydrous toluene (10 cm$^3$) for one hour. To the mixture was added tris(dibenzylideneacetone)dipalladium(0) (2.8 mg, 0.003 mmol) followed by a degassed solution of sodium carbonate (0.23 cm$^3$, 0.46 mmol, 2 M in water). The reaction mixture was then degassed for a further 30 minutes followed by heating at 110° C. for 17 hours. The mixture was allowed to cool slightly, poured into stirred methanol (100 cm$^3$) and the polymer precipitate collected by filtration. The crude polymer was subjected to sequential Soxhlet extraction; acetone, 40-60 petrol, 80-100 petrol, cyclohexane and chloroform. The chloroform extract was poured into methanol (400 cm$^3$) and the polymer precipitate collected by filtration to give polymer 5 (120 mg, 34%) as a dark yellow solid.

GPC (chlorobenzene, 50° C.) $M_n$=16,000 g/mol, $M_w$=38,000 g/mol.

Example 9

Polymer 6

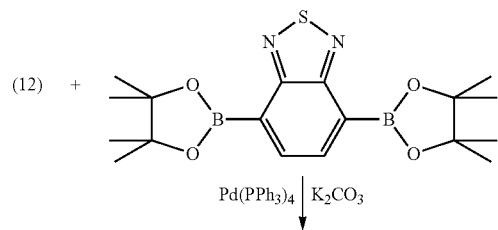

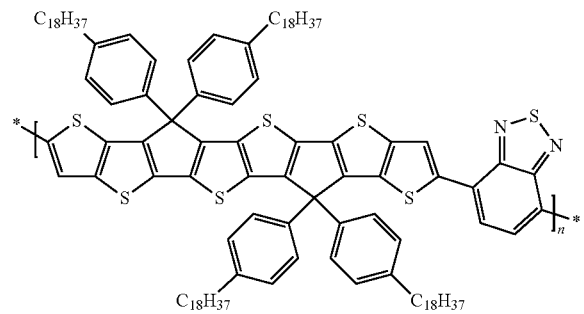

To a mixture of compound 12 (382.8 mg, 0.200 mmol), 4,7-bis-(4,4,5,5-tetramethyl-[1,3,2]dioxaborolan-2-yl)-benzo[1,2,5]thiadiazole (77.7 mg, 0.200 mmol), tetrakis(triphenylphosphine)palladium (0) (23.1 mg, 0.02 mmol), potassium carbonate (0.28 g, 0.002 mmol) was added a degassed mixture of water (1.0 cm$^3$), 1,4-dioxane (2.0 cm$^3$) and toluene (3.0 cm$^3$). The reaction mixture was then heated at 110° C. for 17 hours. The mixture was allowed to cool slightly, poured into stirred methanol/water (1:1, 200 cm$^3$) and the polymer precipitate collected by filtration. The crude polymer was subjected to sequential Soxhlet extraction; acetone, methanol, 40-60 petrol and cyclohexane. The cyclohexane extract was concentrated in vacuo and poured into methanol (350 cm$^3$) and the polymer precipitate collected by filtration to give polymer 6 (161 mg, 43%) as a red solid.

GPC (chlorobenzene, 50° C.) $M_n$=18,000 g/mol, $M_w$=37,000 g/mol.

Example 10

Polymer 7

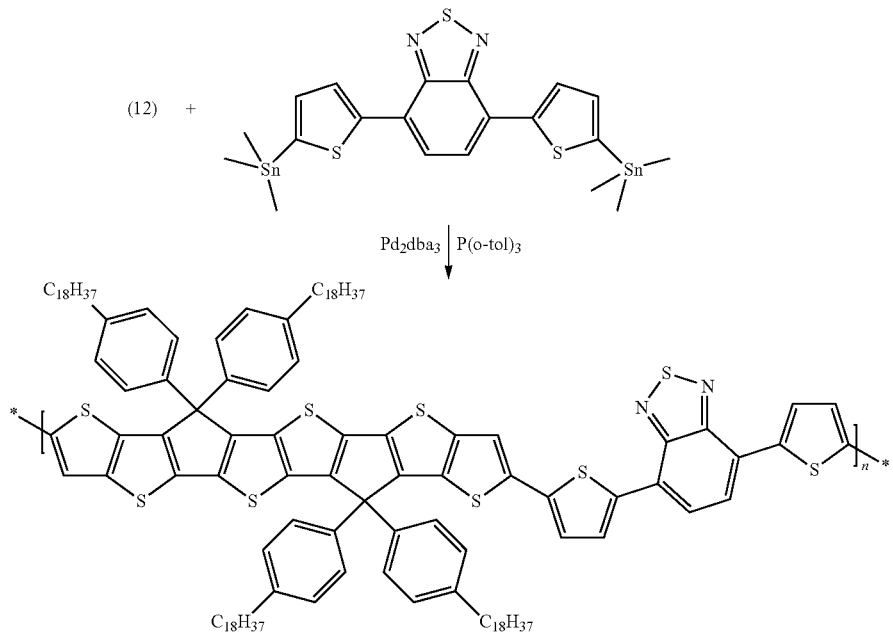

Nitrogen gas was bubbled through a mixture of compound 12 (270.0 mg, 0.141 mmol), 4,7-bis-(5-trimethylstannanyl-thiophen-2-yl)-benzo[1,2,5]thiadiazole (88.4 mg, 0.141 mmol), tris(dibenzylideneacetone)dipalladium(0) (1.5 mg, 0.002 mmol), tri-o-tolyl-phosphine (2.6 mg, 0.009 mmol) and anhydrous toluene (5 cm$^3$) for 35 minutes. The reaction mixture was then heated in a pre-heated oil bath at 110° C. for 10 minutes. Bromobenzene (0.03 cm$^3$) was added and the mixture heated at 110° C. for 15 minutes. Tributyl-phenyl-stannane (0.14 cm$^3$) was then added and the mixture heated at 110° C. for 15 minutes. The mixture was allowed to cool slightly, poured into stirred methanol (200 cm$^3$) and the polymer precipitate collected by filtration. The crude polymer was subjected to sequential Soxhlet extraction; acetone, 40-60 petrol, 80-100 petrol, cyclohexane and chloroform. The chloroform extract was concentrated in vacuo and poured into methanol (300 cm$^3$) and the polymer precipitate collected by filtration to give polymer 7 (285 mg, 98%) as a red solid.

GPC (chlorobenzene, 50° C.) $M_n$=98,000 g/mol, $M_w$=255,000 g/mol.

Example 11

Transistor Fabrication and Measurement

Top-gate thin-film organic field-effect transistors (OFETs) were fabricated on glass substrates with photolithographically defined Au source-drain electrodes. A 7 mg/cm$^3$ solution of the organic semiconductor in dichlorobenzene was spin-coated on top (an optional annealing of the film was carried out at 100° C., 150° C. or 200° C. for between 1 and 5 minutes) followed by a spin-coated fluoropolymer dielectric material (Lisicon® D139 from Merck, Germany). Finally a photolithographically defined Au gate electrode was deposited. The electrical characterization of the transistor devices was carried out in ambient air atmosphere using computer controlled Agilent 4155C Semiconductor Parameter Analyser. Charge carrier mobility in the saturation regime ($\mu_{sat}$) was calculated for the compound. Field-effect mobility was calculated in the saturation regime ($V_d$>($V_g$−$V_0$)) using equation (eq. 1):

$$\left(\frac{dI_d^{sat}}{dV_g}\right)_{V_d} = \frac{WC_i}{L}\mu^{sat}(V_g - V_0) \qquad \text{(eq. 1)}$$

where W denotes the channel width, L the channel length, $C_i$ the capacitance of insulating layer, $V_g$ the gate voltage, $V_0$ the turn-on voltage, and $\mu_{sat}$ the charge carrier mobility in the saturation regime. Turn-on voltage ($V_0$) was determined as the onset of source-drain current.

The mobilities ($\mu_{sat}$) for polymers 1, 2, 3, 4 and 7 in top-gate OFETs are summarised in Table 1.

TABLE 1

| Polymer | $\mu_{sat}$ [cm$^2$/Vs] |
| --- | --- |
| 1 | 0.06 |
| 2 | 0.15 |
| 3 | 0.40 |
| 4 | 0.08 |
| 7 | 0.07 |

Example 12

Bulk Heterojunction OPV Device for Polymer 7

Organic photovoltaic (OPV) devices were fabricated on pre-patterned ITO-glass substrates (13 Ω/sq.) purchased from LUMTEC Corporation. Substrates were cleaned using common solvents (acetone, iso-propanol, deionized-water) in an ultrasonic bath. A conducting polymer poly(ethylene dioxythiophene) doped with poly(styrene sulfonic acid) (Clevios VPAI 4083, H. C. Starck) was mixed in a 1:1 ratio with deionized-water. This solution was filtered using a 0.45 µm filter before spin-coating to achieve a thickness of 20 nm. Substrates were exposed to ozone prior to the spin-coating process to ensure good wetting properties. Films were then annealed at 140° C. for 30 minutes in a nitrogen atmosphere where they were kept for the remainder of the process. Active material solutions (i.e. polymer+C$_{60}$PCBM) were prepared and stirred overnight to fully dissolve the solutes. Thin films were either spin-coated or blade-coated in a nitrogen atmosphere to achieve active layer thicknesses between 100 and 500 nm as measured using a profilometer. A short drying period followed to ensure removal of any residual solvent.

Typically, spin-coated films were dried at 23° C. for 10 minutes and blade-coated films were dried at 70° C. for 2 minutes on a hotplate. For the last step of the device fabrication, Ca (30 nm)/Al (125 nm) cathodes were thermally evaporated through a shadow mask to define the cells. Current-voltage characteristics were measured using a Keithley 2400 SMU while the solar cells were illuminated by a Newport Solar Simulator at 100 mW·cm$^{-2}$ white light. The Solar Simulator was equipped with AM1.5G filters. The illumination intensity was calibrated using a Si photodiode. All the device preparation and characterization was done in a dry-nitrogen atmosphere.

Power conversion efficiency was calculated using the following expression $$\eta = \frac{V_{oc} \times J_{sc} \times FF}{P_{in}}$$

where FF was defined as $$FF = \frac{V_{max} \times J_{max}}{V_{oc} \times J_{sc}}$$

OPV devices were prepared wherein the photoactive layer contains a blend of polymer 7 and the fullerene PC$_{61}$BM, which was coated from an o-dichlorobenzene solution at a total solid concentration as given in Table 2 below. The OPV device characteristics are shown in Table 2.

TABLE 2

Photovoltaic cell characteristics

|  |  | Polymer 7 |
| --- | --- | --- |
| Ratio Polymer:C$_{60}$PCBM | [wt:wt] | 1:3 |
| Concentration | [mg ml$^{-1}$] | 30 |
| V$_{oc}$ | [mV] | 576 |
| J$_{SC}$ | [mA cm$^{-2}$] | -4.32 |
| FF | [%] | 45 |
| PCE | [%] | 1.13 |

The invention claimed is:

1. Compound comprising a divalent unit selected from the group consisting of units of the following formula (I)

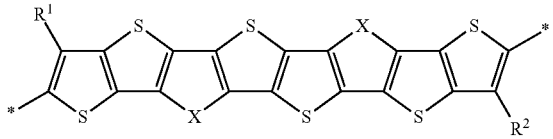

(I)

wherein R$^1$ and R$^2$ are independently of each other selected from the group consisting of H, halogen, carbyl and hydrocarbyl, and X is at each occurrence independently selected from the group consisting of CR$^3$R$^4$, SiR$^3$R$^4$, GeR$^3$R$^4$ and C=CR$^3$R$^4$, with R$^3$ and R$^4$ being independently of each other selected from the group consisting of hydrogen, carbyl and hydrocarbyl.

2. Compound according to claim 1, wherein X is CR$^3$R$^4$ or SiR$^3$R$^4$.

3. Compound according to claim 1, wherein X is CR$^3$R$^4$.

4. Compound according to claim 1 comprising a divalent unit of the following formulae (Ia)

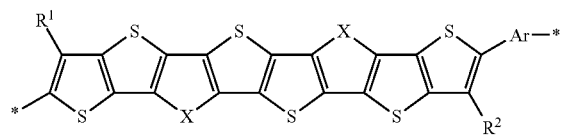

(Ia)

wherein Ar comprises an aromatic ring system comprising from 6 to 60 aromatic carbon atoms or a heteroaromatic ring system comprising from 5 to 60 aromatic ring atoms, at least one of which is a heteroatom.

5. Compound according to claim 4, wherein Ar is selected from the group consisting of formulae (D1) to (132) and (A1) to (A93):

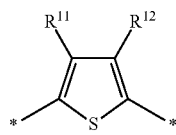

(D1)

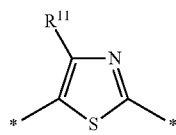

(D2)

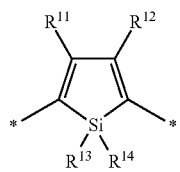

(D3)

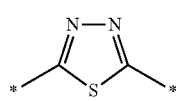

(D4)

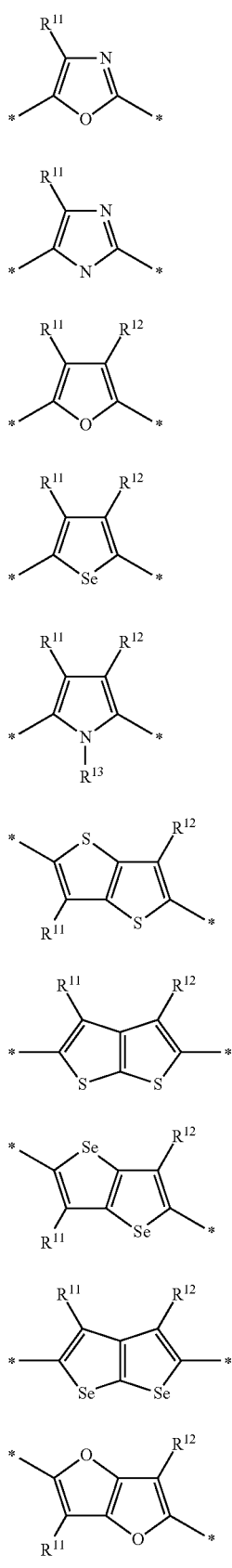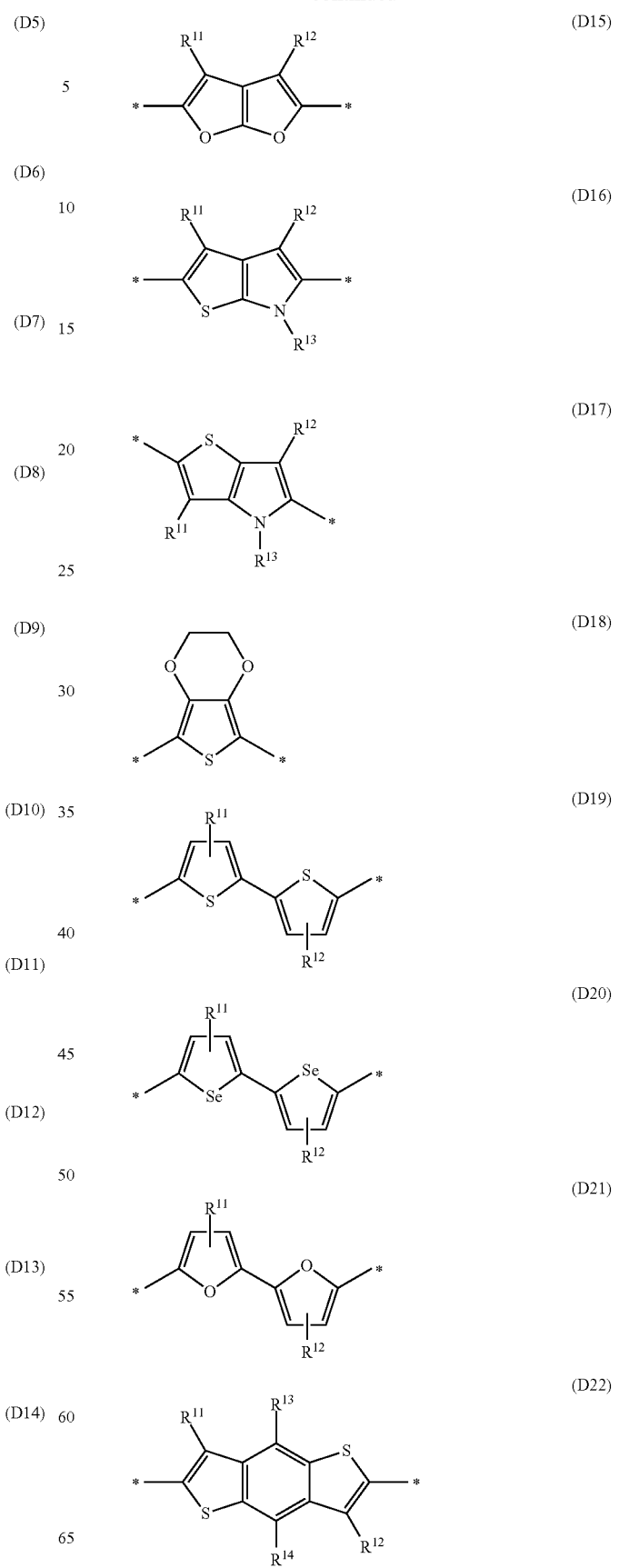

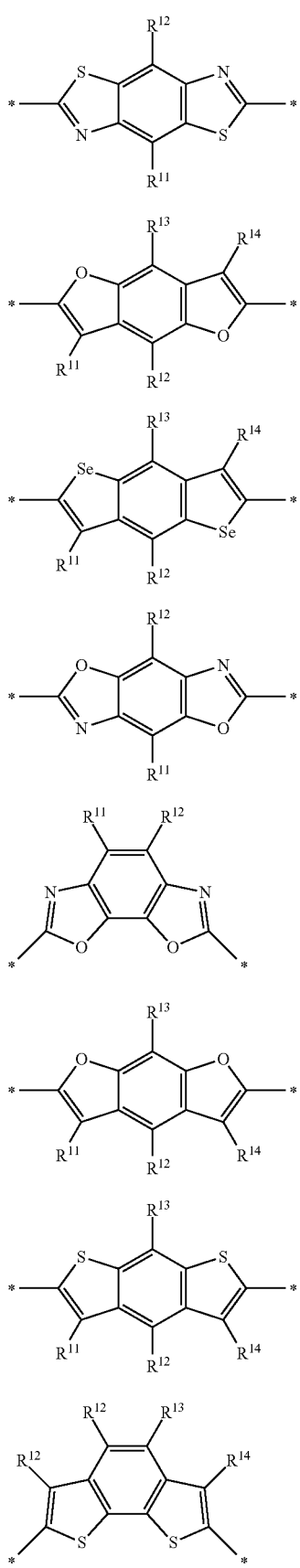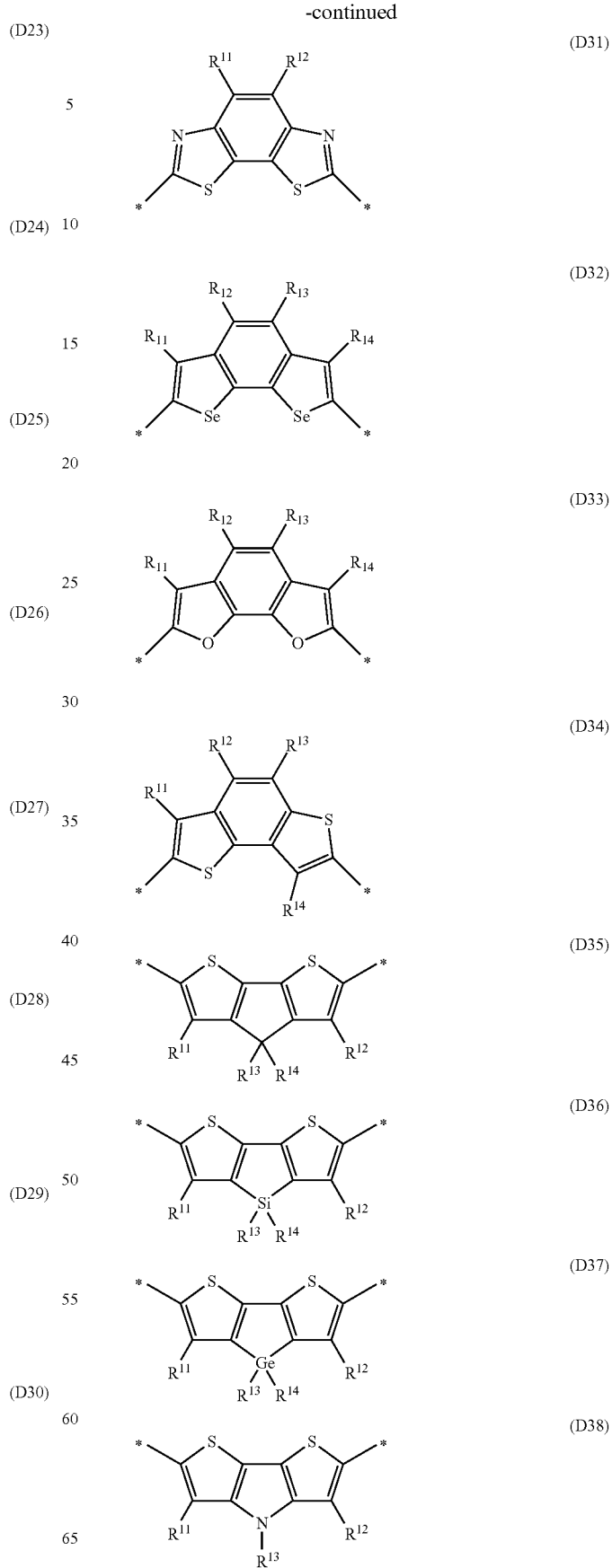

-continued
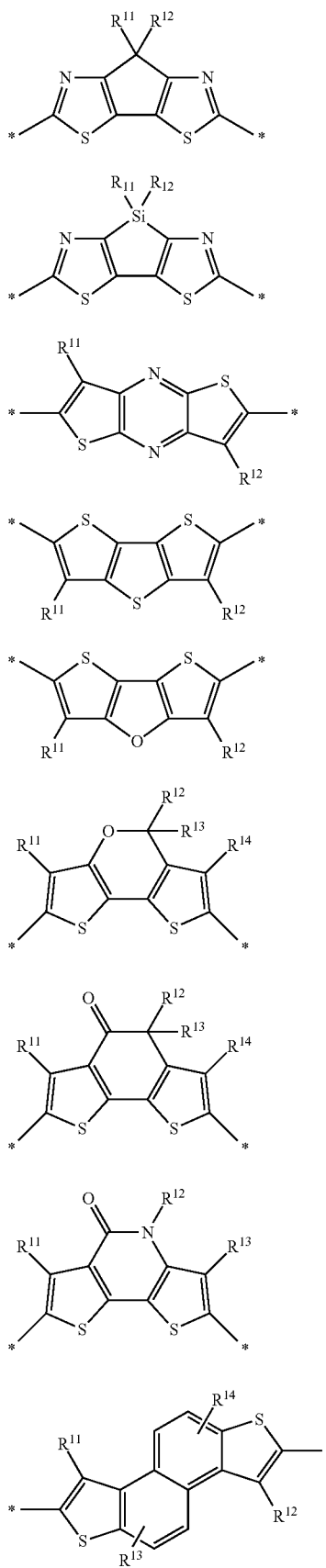
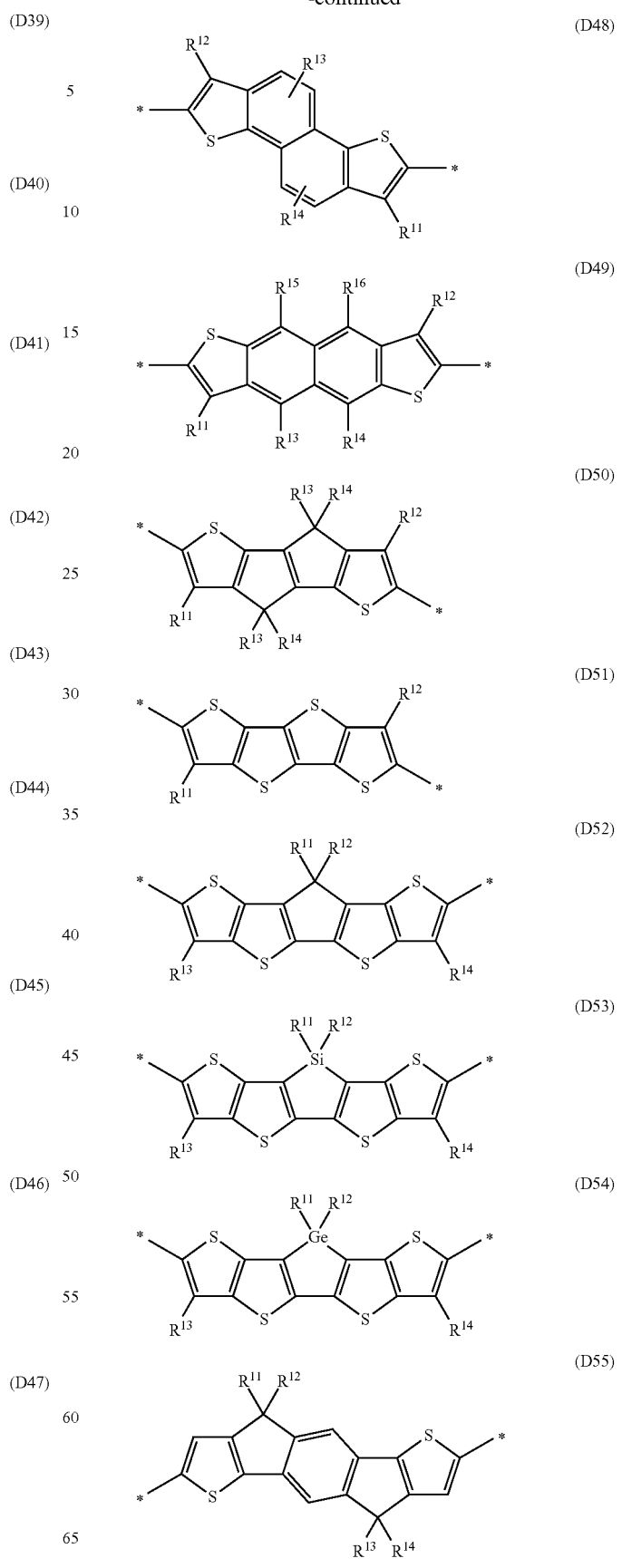

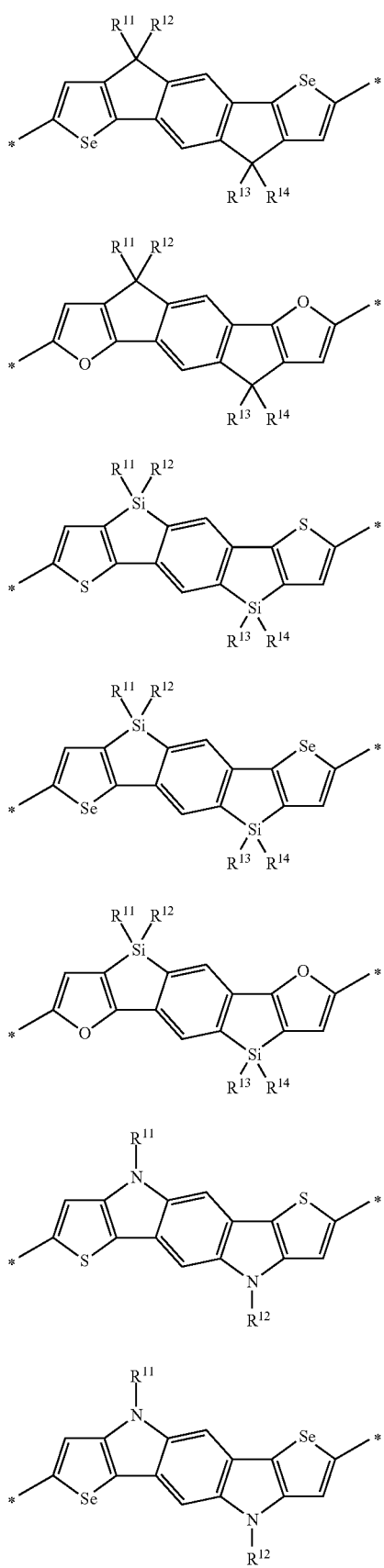

-continued
(D70)
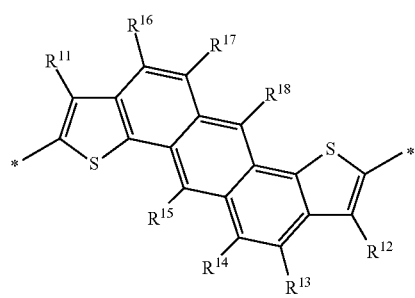
(D71)
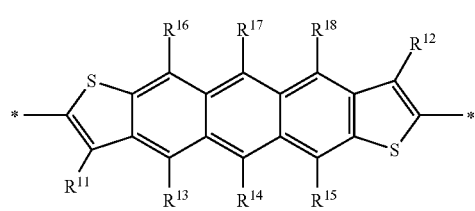
(D72)
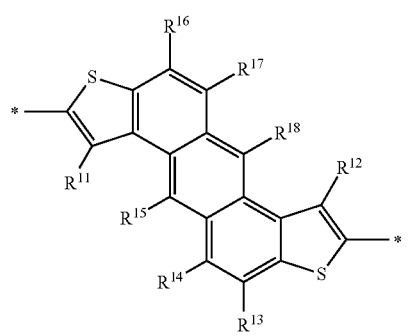
(D73)
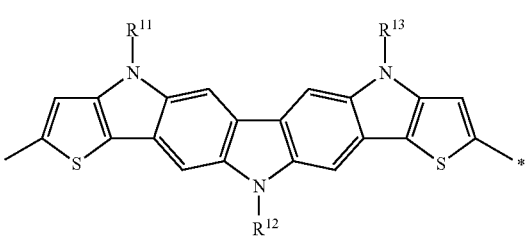
(D74)
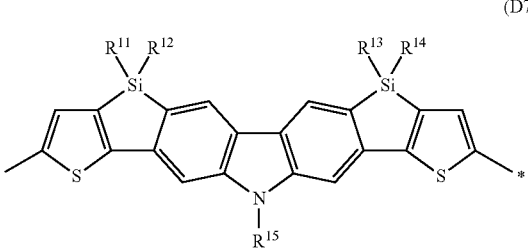
(D75)
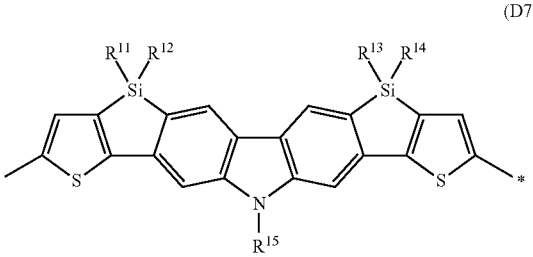
-continued
(D76)
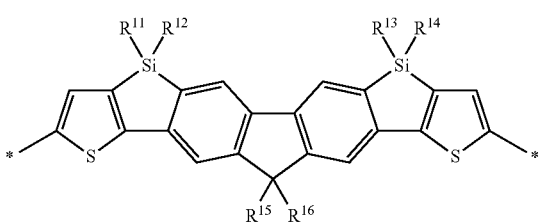
(D77)
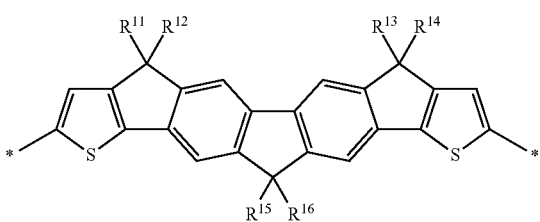
(D78)
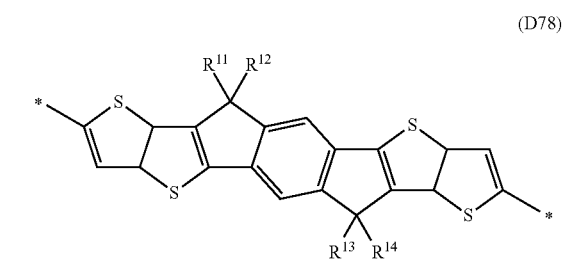
(D79)
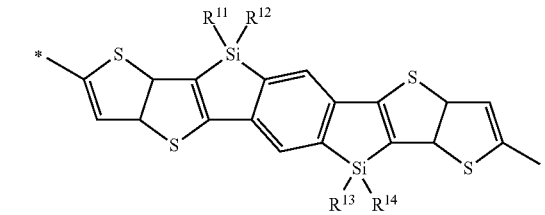
(D80)
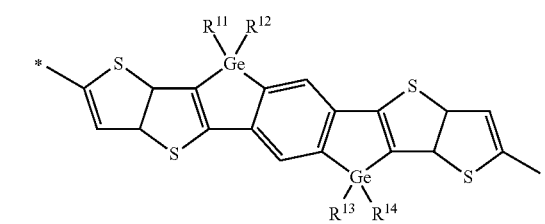
(D81)
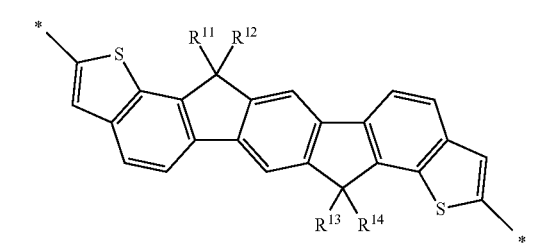

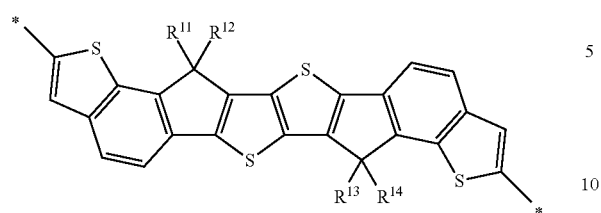
(D82)
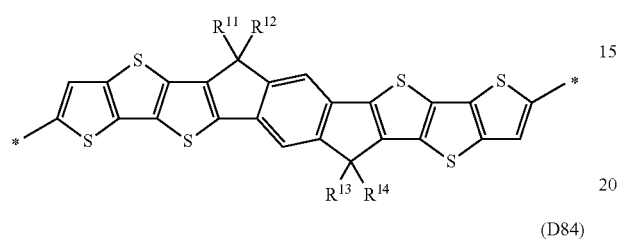
(D83)
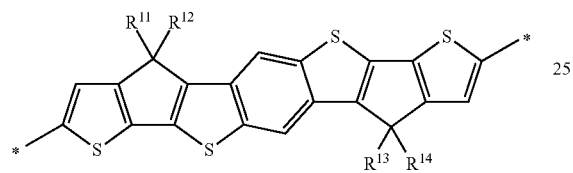
(D84)
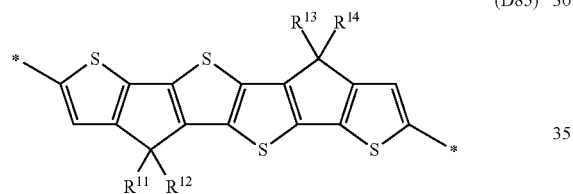
(D85)
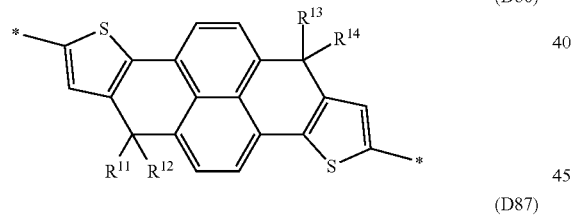
(D86)
(D87)
(D88)
(D89)
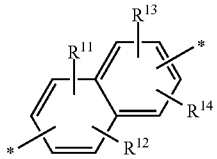
(D90)
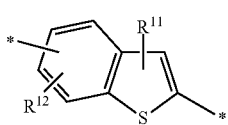
(D91)
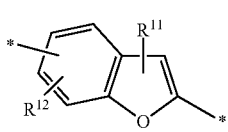
(D92)
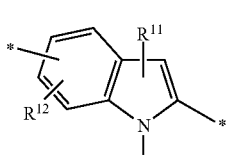
(D93)
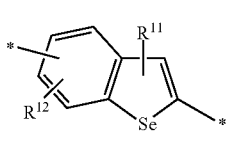
(D94)
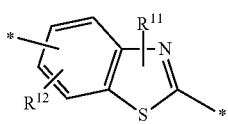
(D95)
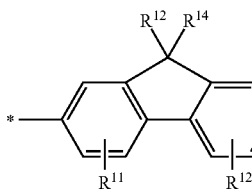
(D96)
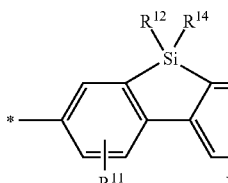
(D97)
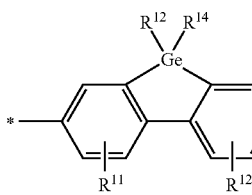
(D98)

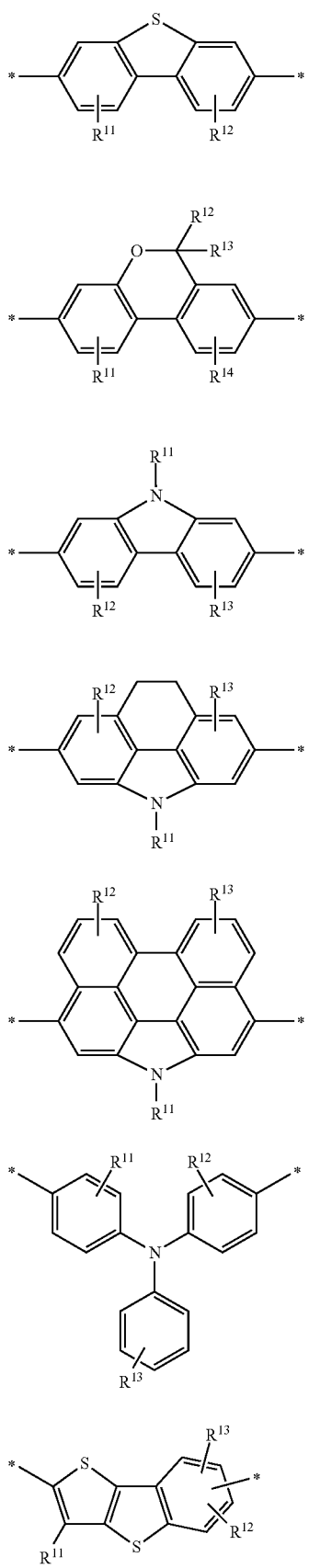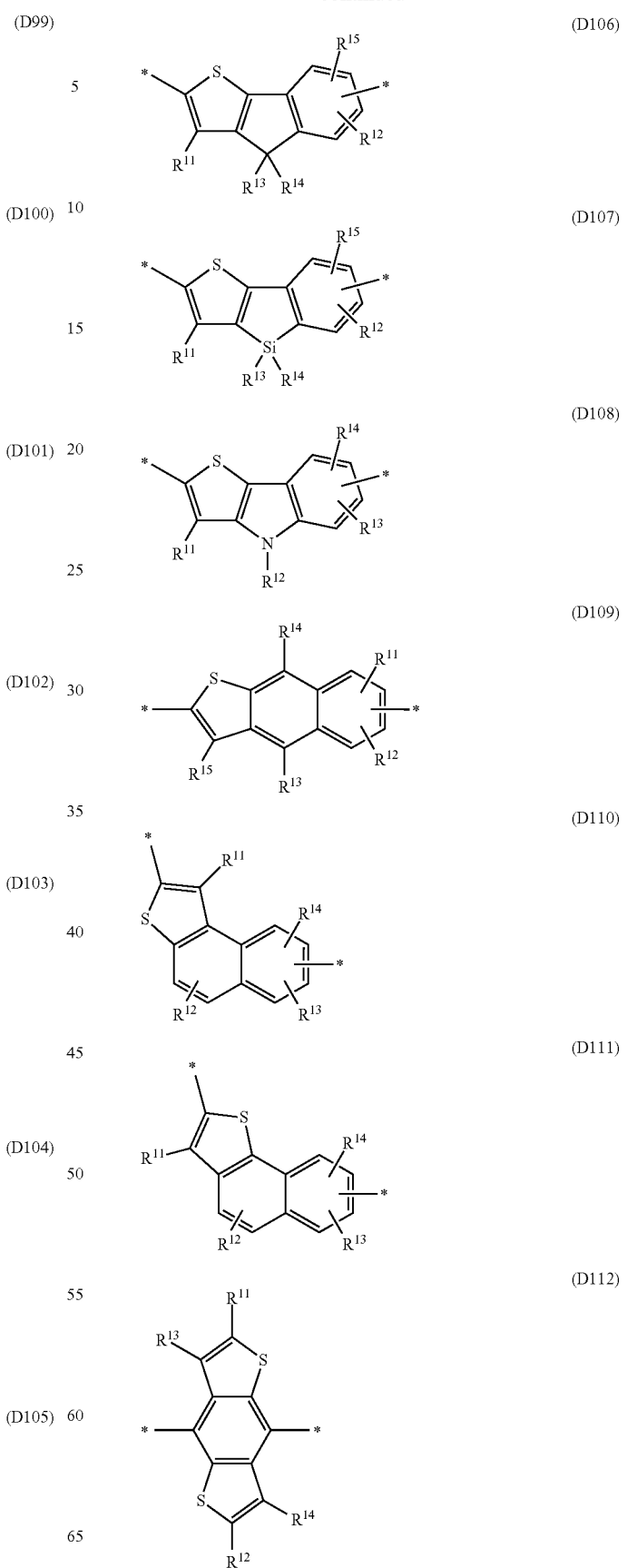

-continued
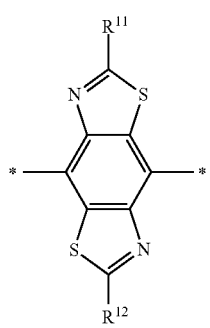
(D113)
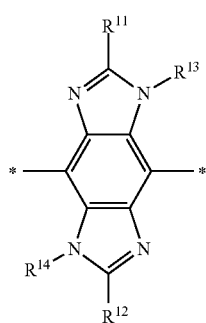
(D114)
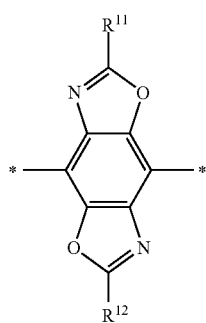
(D115)
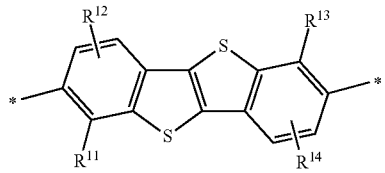
(D116)
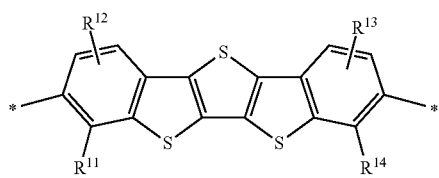
(D117)
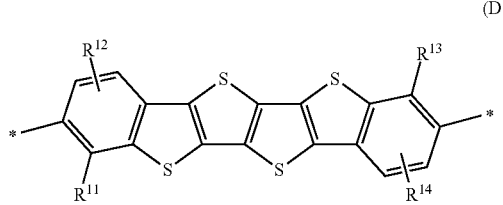
(D118)
-continued
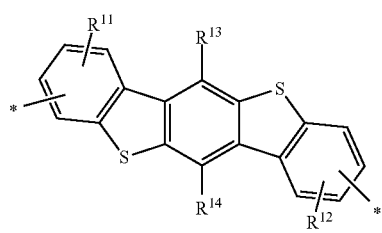
(D119)
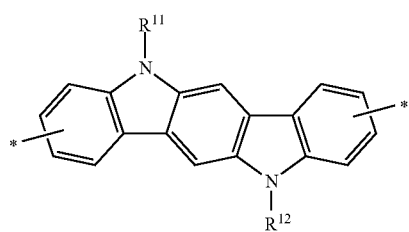
(D120)
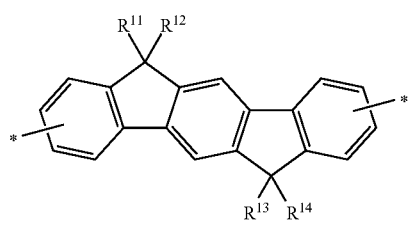
(D121)
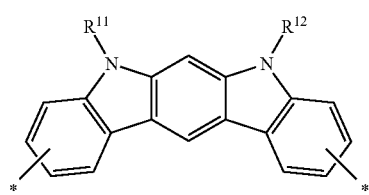
(D122)
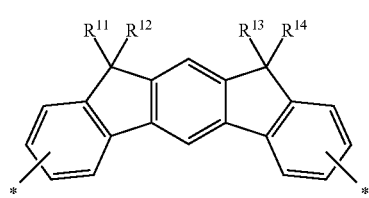
(D123)
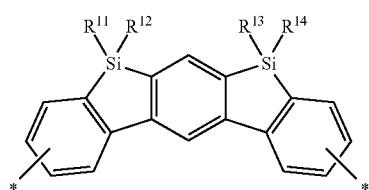
(D124)
(D125)

-continued

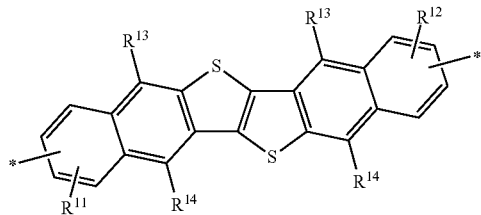
(D126)

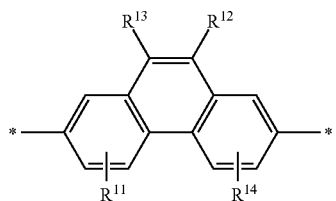
(D127)

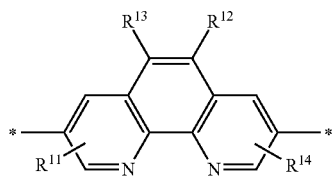
(D128)

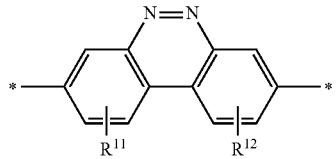
(D129)

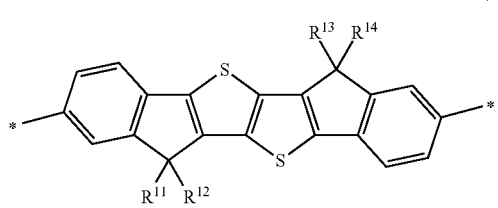
(D130)

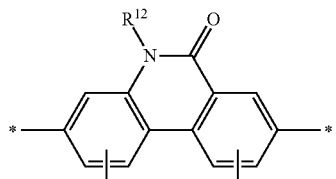
(D131)

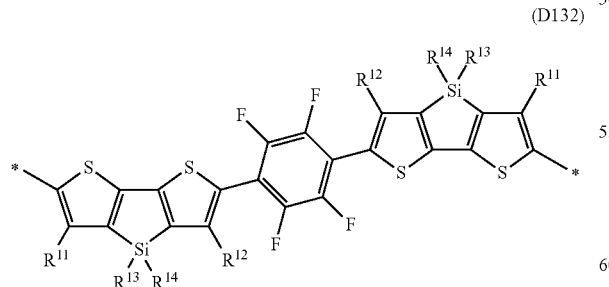
(D132)

wherein $R^{11}$, $R^{12}$, $R^{13}$, $R^{14}$, $R^{15}$, $R^{16}$, $R^{17}$ and $R^{18}$ are independently of each other selected from the group consisting of hydrogen, F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, and optionally substituted silyl or hydrocarbyl with 1 to 40 C atoms that is optionally substituted and optionally comprises one or more hetero atoms, where X$^0$ is halogen and R$^0$ and R$^{00}$ are, independently of each other, H or optionally substituted C$_{1-40}$ carbyl or hydrocarbyl.

6. Compound according to claim 5, wherein Ar is selected from the group consisting of formulae (D1), (D10), (D19), (A1) and (A19), wherein $R^{11}$ and $R^{12}$ are independently of each other hydrogen or fluorine.

7. Compound according to claim 1 comprising a group M, which comprises the following structure:

$$*-U^a_{m1}-Ar^a_{m2}-U^b_{m3}-Ar^b_{m4}-Ar^c_{m5}-*$$  (III)

wherein

U$^a$ and U$^b$ are independently of each other selected from the divalent unit selected from the group consisting of formulae (I) of claim 1;

Ar$^a$, Ar$^b$ and Ar$^c$ are independently of each other aryl or heteroaryl different from U$^a$ and U$^b$;

m1, m2, m3 and m4 are independently of each other selected from the group consisting of 0, 1 and 2, with the provision that at least one of m1 and m3 is not 0; and m5 is 0 or an integer from 1 to 10.

8. Compound according to claim 7, wherein Ar$^a$, Ar$^b$ and Ar$^c$—if present—are independently of each other selected from the group consisting of formulae (D1) to (D132) and (A1) to (A93):

(D1)

(D2)

(D3)

(D4)

(D5)

(D6)

-continued
(D7) 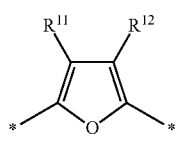
(D8) 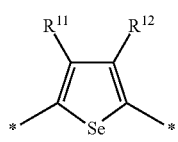
(D9) 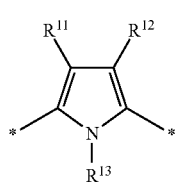
(D10) 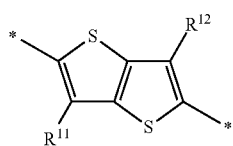
(D11) 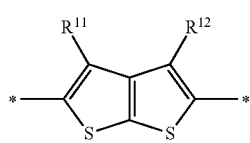
(D12) 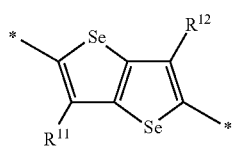
(D13) 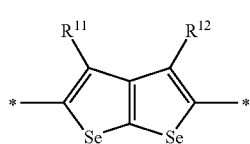
(D14) 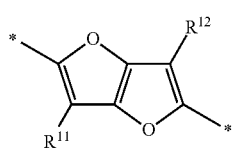
(D15) 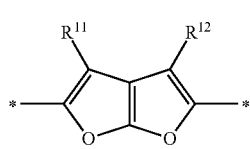
(D16) 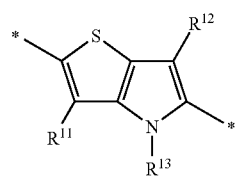
-continued
(D17) 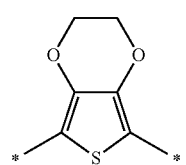
(D18) 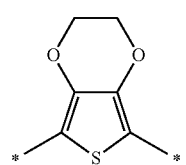
(D19) 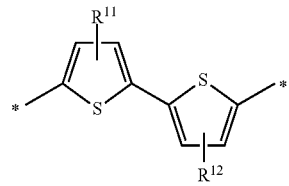
(D20) 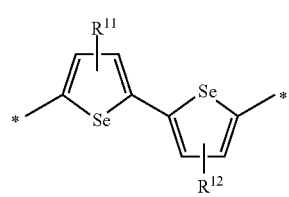
(D21) 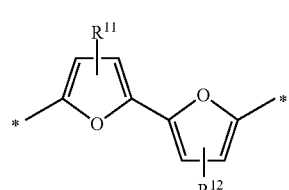
(D22) 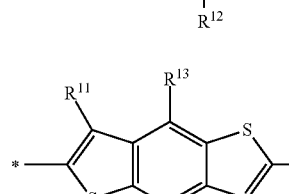
(D23) 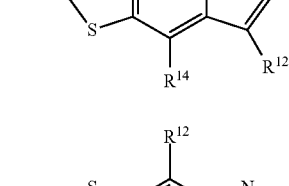
(D24) 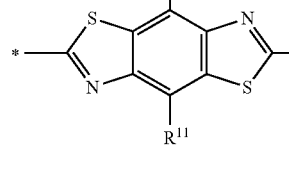
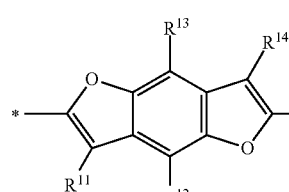

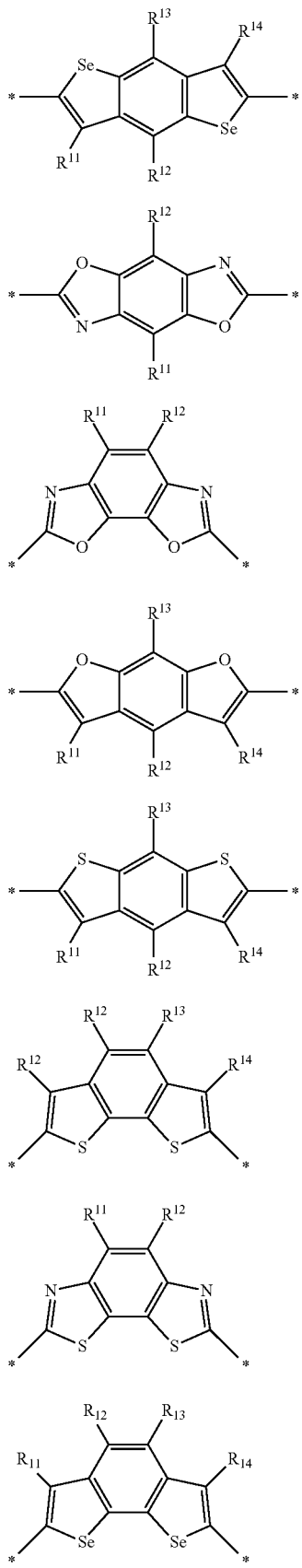
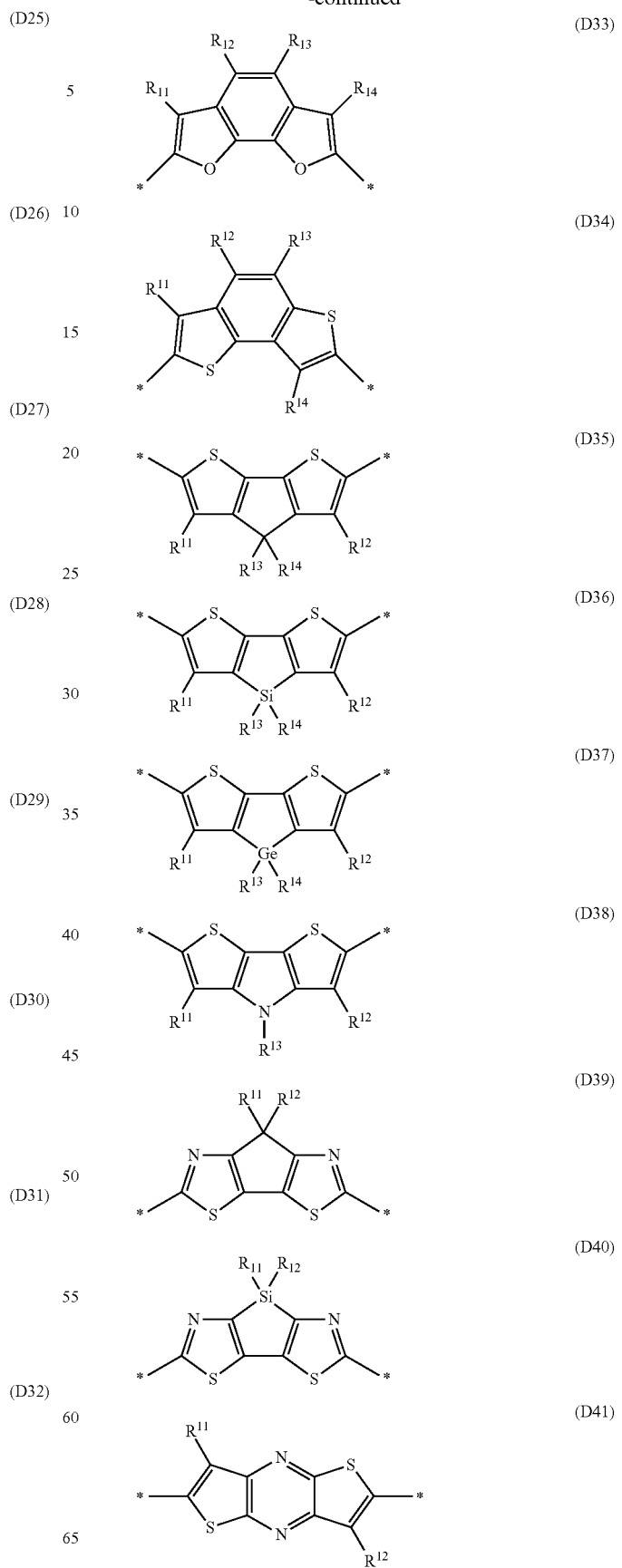

105
-continued
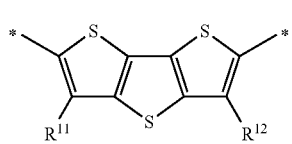
(D42)
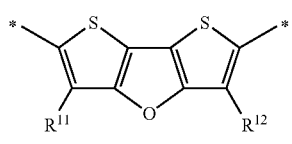
(D43)
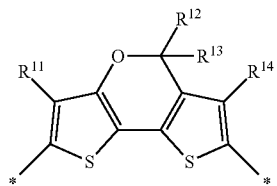
(D44)
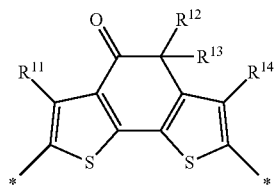
(D45)
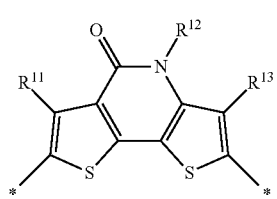
(D46)
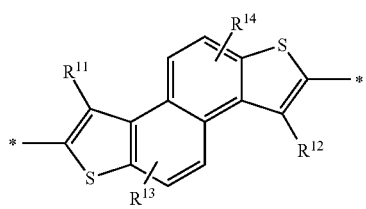
(D47)
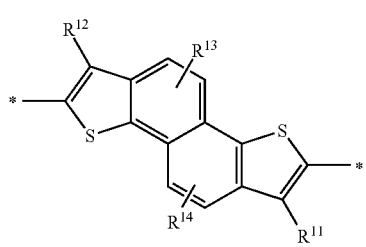
(D48)
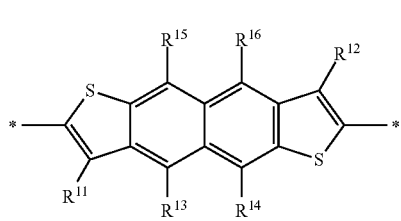
(D49)
106
-continued
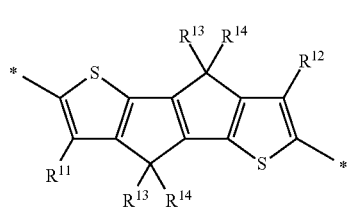
(D50)
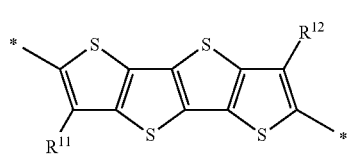
(D51)
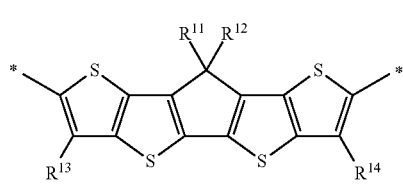
(D52)
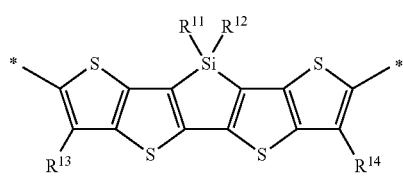
(D53)
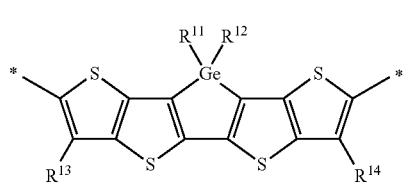
(D54)
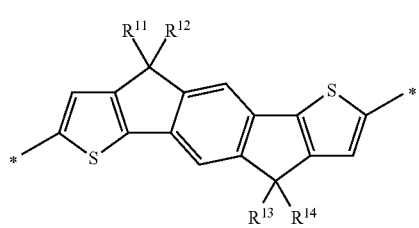
(D55)
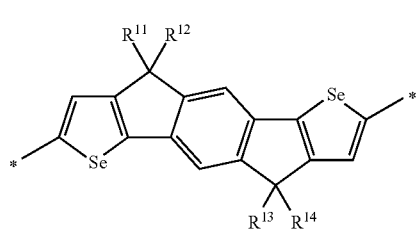
(D56)
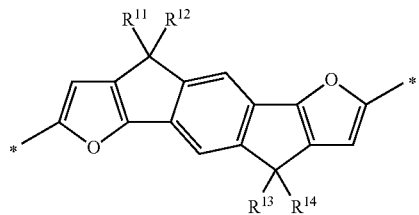
(D57)

-continued
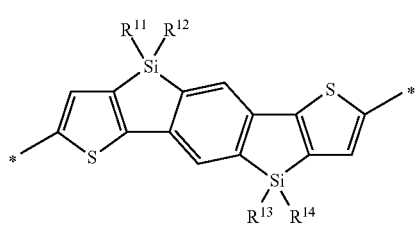
(D58)
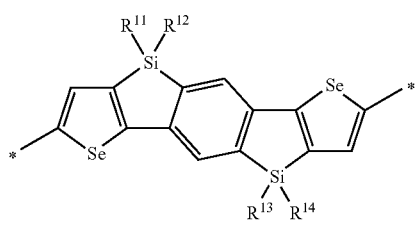
(D59)
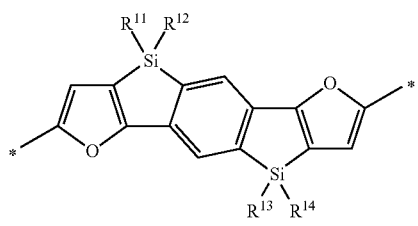
(D60)
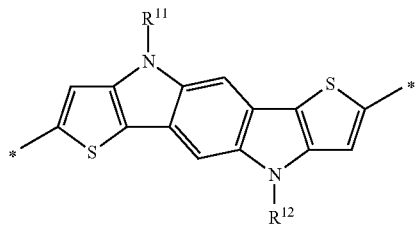
(D61)
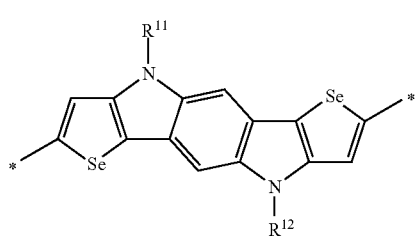
(D62)
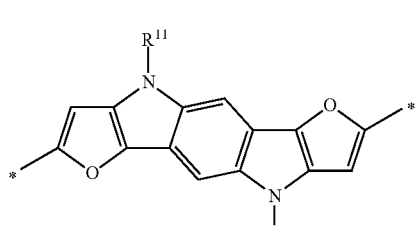
(D63)
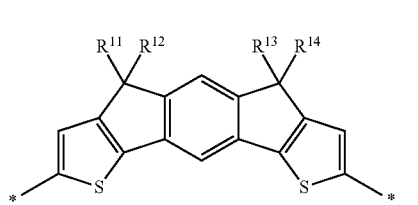
(D64)
-continued
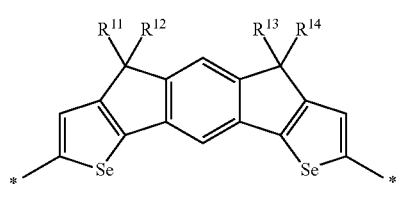
(D65)
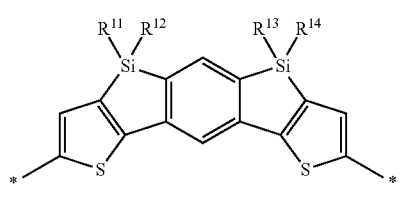
(D66)
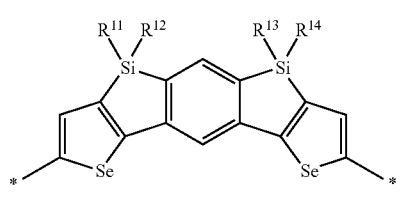
(D67)
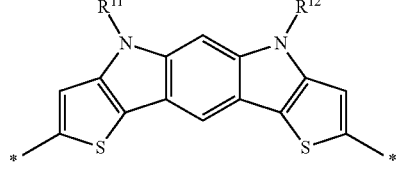
(D68)
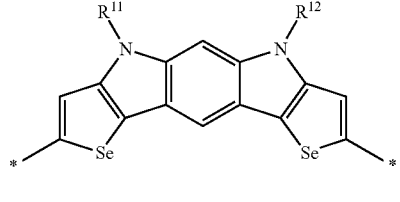
(D69)
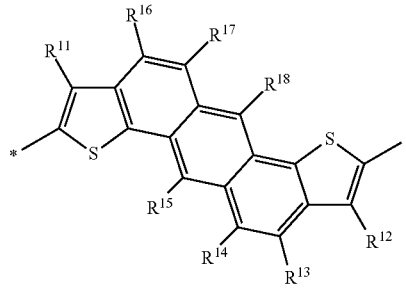
(D70)
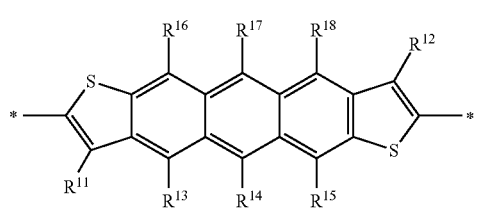
(D71)

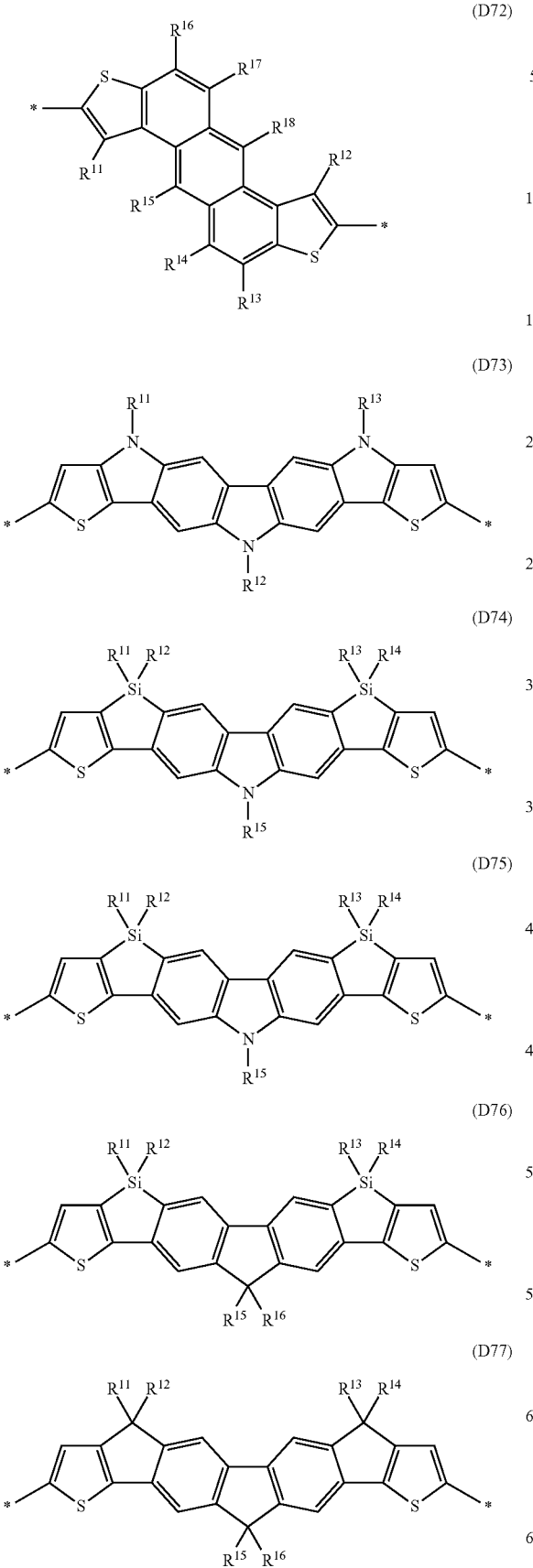
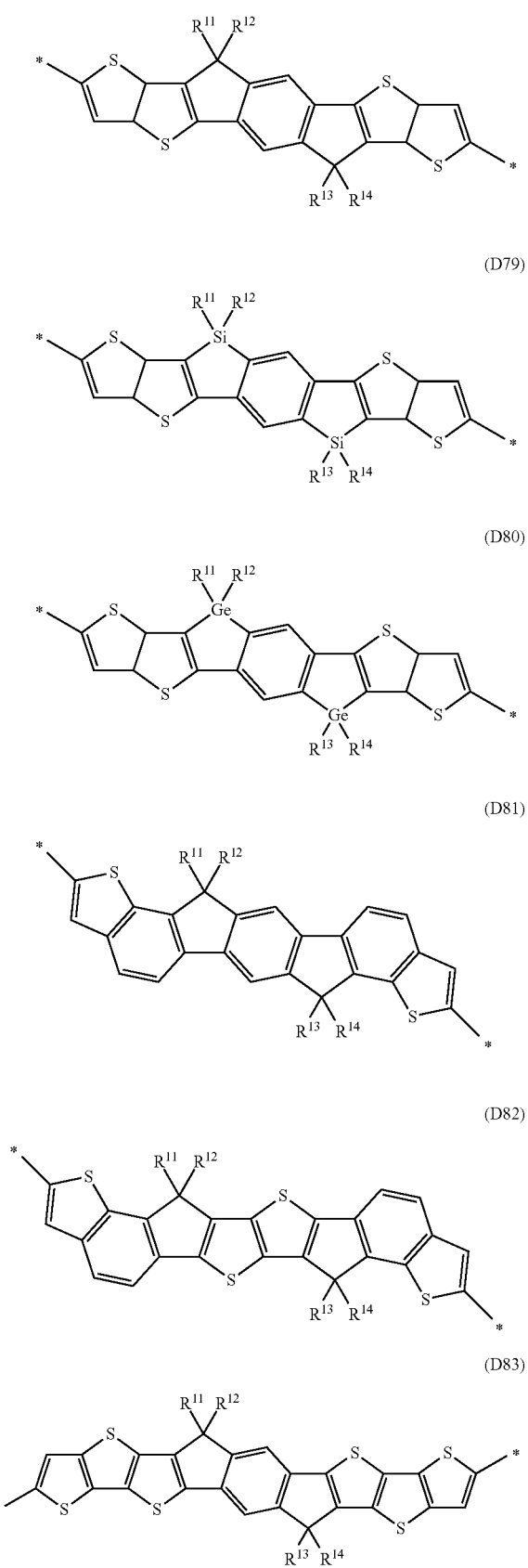

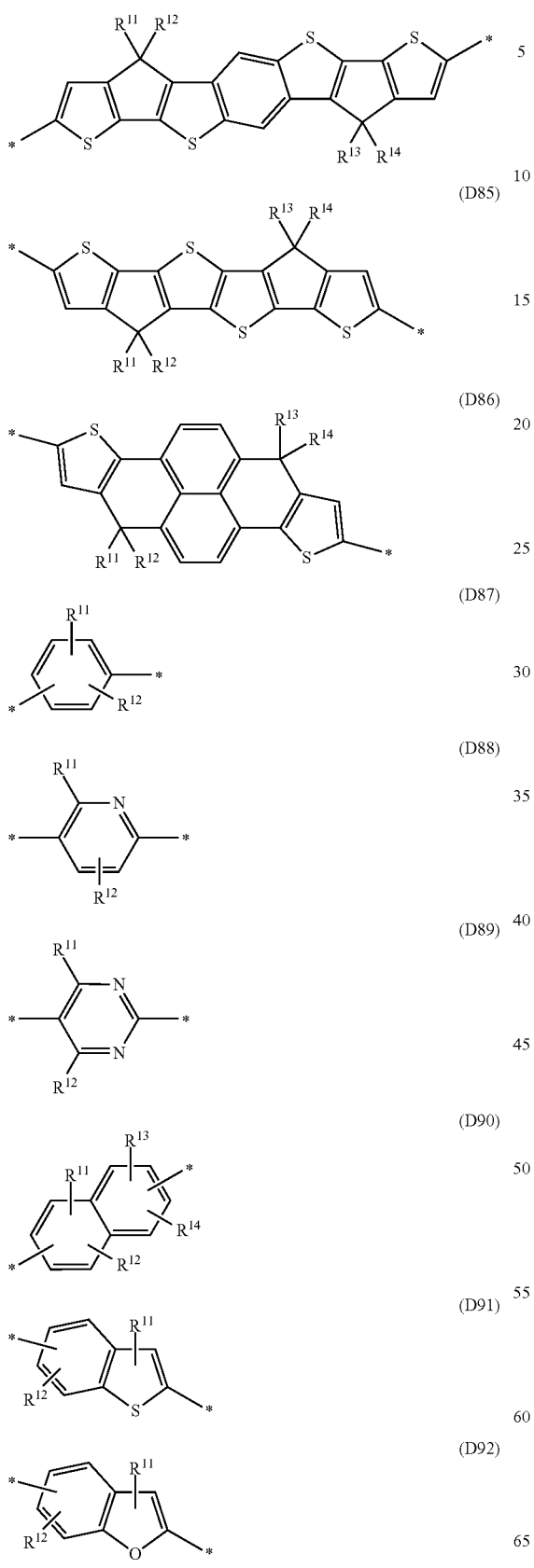
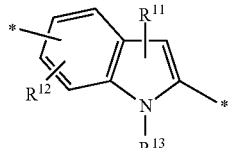
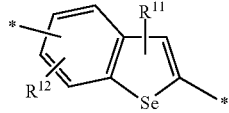
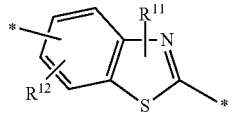
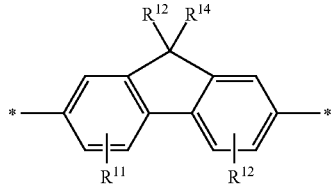
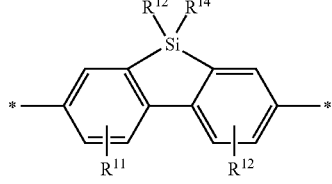
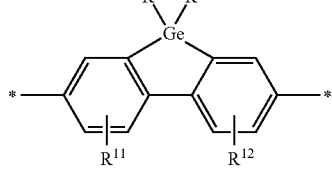
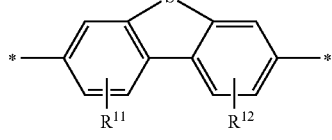
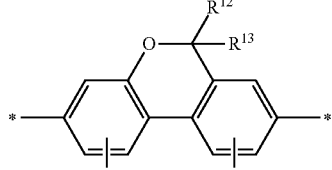
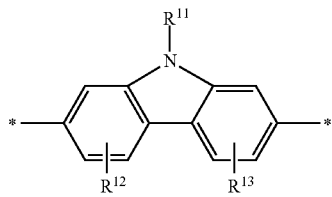

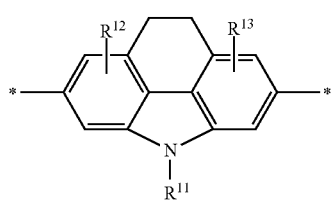
(D102)
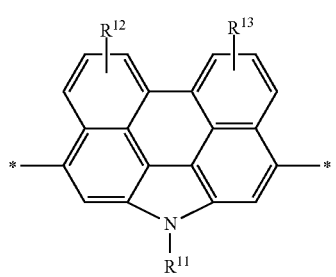
(D103)
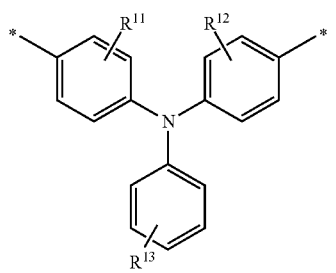
(D104)
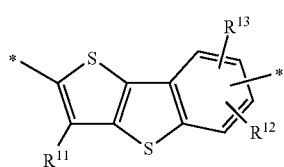
(D105)
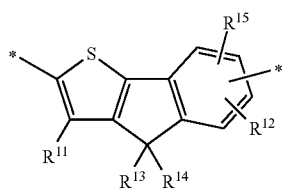
(D106)
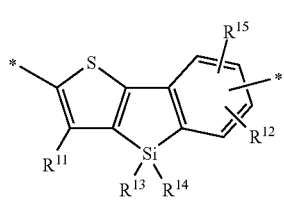
(D107)
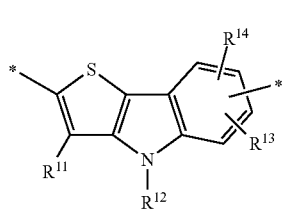
(D108)
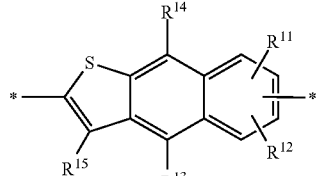
(D109)
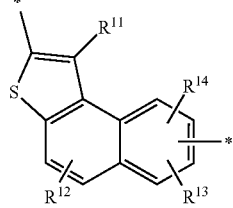
(D110)
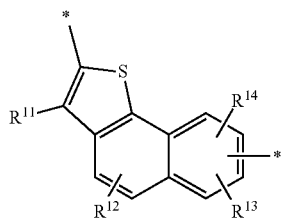
(D111)
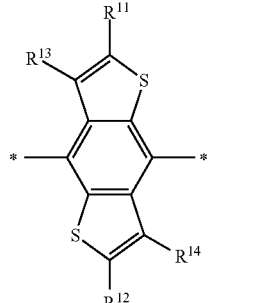
(D112)
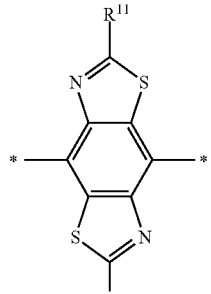
(D113)
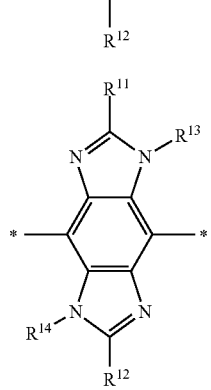
(D114)

-continued
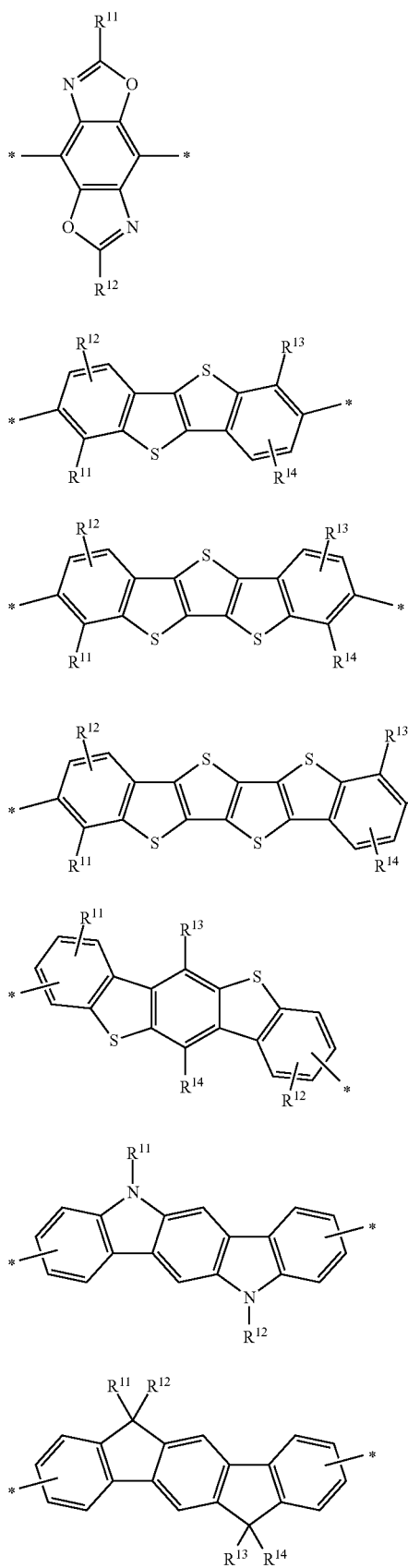
(D115)
(D116)
(D117)
(D118)
(D119)
(D120)
(D121)
-continued
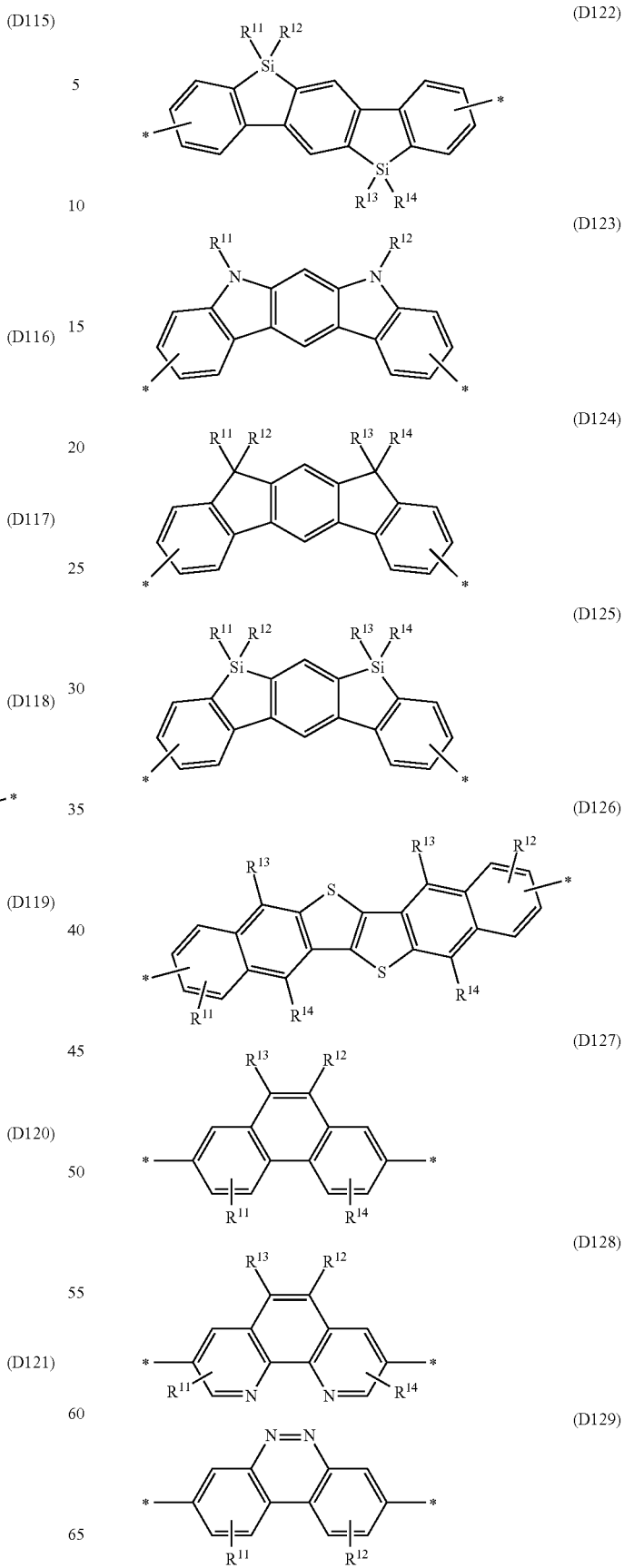
(D122)
(D123)
(D124)
(D125)
(D126)
(D127)
(D128)
(D129)

-continued

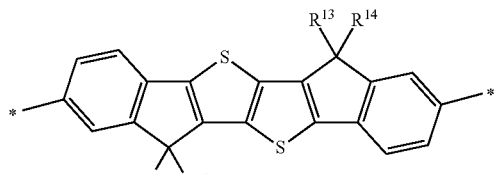
(D130)

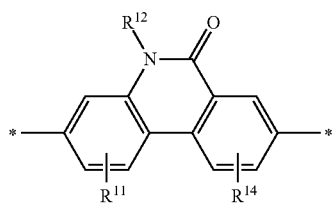
(D131)

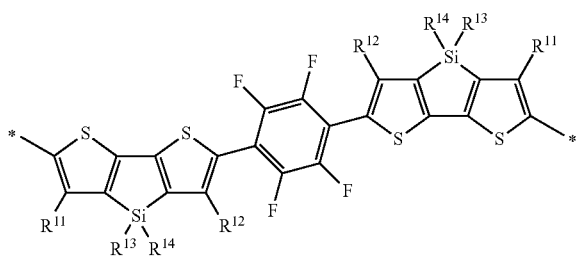
(D132)

wherein $R^{11}$, $R^{12}$, $R^{13}$, $R^{14}$, $R^{15}$, $R^{16}$, $R^{17}$ and $R^{18}$ are independently of each other selected from the group consisting of hydrogen, F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, and optionally substituted silyl or hydrocarbyl with 1 to 40 C atoms that is optionally substituted and optionally comprises one or more hetero atoms, where X$^0$ is halogen and R$^0$ and R$^{00}$ are, independently of each other, H or optionally substituted C$_{1-40}$ carbyl or hydrocarbyl.

9. Compound according to claim 8, wherein Ar$^a$, Ar$^b$ and Ar$^c$—if present—are independently of each other selected from the group consisting of formulae (D1), (D10), (D19), (A1) and (A19), wherein $R^{11}$ and $R^{12}$ are independently of each other hydrogen or fluorine.

10. Compound according to claim 1, wherein the compound is selected from the group consisting of small molecule, monomer, oligomer and polymer.

11. A mixture or a blend comprising one or more compounds of claim 1 and one or more compounds or polymers having semiconducting, charge transport, hole transport, electron transport, hole blocking, electron blocking, electrically conducting, photoconducting or light emitting properties.

12. Formulation comprising the compound of claim 1 and an organic solvent.

13. Charge transport, semiconducting, electrically conducting, photoconducting or light emitting material comprising the compound of claim 1.

14. A component or device comprising the compound of claim 1, said component or device being selected from the group consisting of organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), organic solar cells (O—SC), photodiodes, laser diodes, photoconductors, organic photodetectors (OPD), electrophotographic devices, electrophotographic recording devices, organic memory devices, sensor devices, charge injection layers, charge transport layers or interlayers in polymer light emitting diodes (PLEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

15. A component or device according to claim 14, said component or device being selected from the group consisting of organic field effect transistors (OFET), thin film transistors (TFT), integrated circuitry (IC), radio frequency identification (RFID) tags, organic light emitting devices (OLED), organic light emitting transistors (OLET) and backlights of displays.

16. Compound according to claim 4 comprising a group M, which comprises the following structure:

$$*—U^a{}_{m1}—Ar^a{}_{m2}—U^b{}_{m3}—Ar^b{}_{m4}—Ar^c{}_{m5}—* \qquad (III)$$

wherein
U$^a$ and U$^b$ are independently of each other selected from the divalent unit selected from the group consisting of formulae (Ia);
Ar$^a$, Ar$^b$ and Ar$^c$ are independently of each other aryl or heteroaryl different from U$^a$ and U$^b$;
m1, m2, m3 and m4 are independently of each other selected from the group consisting of 0, 1 and 2, with the provision that at least one of m1 and m3 is not 0; and
m5 is 0 or an integer from 1 to 10.

* * * * *